US008840890B2

(12) United States Patent
Lewis et al.

(10) Patent No.: US 8,840,890 B2
(45) Date of Patent: Sep. 23, 2014

(54) RAPID EXPRESSION CLONING OF HUMAN MONOCLONAL ANTIBODIES FROM MEMORY B CELLS

(75) Inventors: George K. Lewis, Baltimore, MD (US); Yongjun Guan, Abingdon, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 421 days.

(21) Appl. No.: 13/128,837

(22) PCT Filed: Nov. 12, 2009

(86) PCT No.: PCT/US2009/064253
§ 371 (c)(1),
(2), (4) Date: May 11, 2011

(87) PCT Pub. No.: WO2010/056898
PCT Pub. Date: May 20, 2010

(65) Prior Publication Data
US 2011/0223615 A1    Sep. 15, 2011

Related U.S. Application Data

(60) Provisional application No. 61/114,047, filed on Nov. 12, 2008.

(51) Int. Cl.
| | |
|---|---|
| *A61K 39/00* | (2006.01) |
| *A61K 39/42* | (2006.01) |
| *C12N 5/07* | (2010.01) |
| *C12N 15/01* | (2006.01) |
| *G01N 33/569* | (2006.01) |
| *C07K 16/00* | (2006.01) |
| *C07K 16/10* | (2006.01) |

(52) U.S. Cl.
CPC ............ *C07K 16/00* (2013.01); *C07K 2317/56* (2013.01); *C07K 2317/21* (2013.01); *G01N 33/56988* (2013.01); *C07K 2316/96* (2013.01); *C07K 2317/565* (2013.01); *C07K 16/1063* (2013.01); *C07K 2317/732* (2013.01)
USPC ...................... 424/142.1; 424/148.1; 435/326; 435/440

(58) Field of Classification Search
None
See application file for complete search history.

(56) References Cited

U.S. PATENT DOCUMENTS

| 2006/0040363 A1 | 2/2006 | Kucherlapati et al. |
| 2008/0193978 A1 | 8/2008 | Raum et al. |

FOREIGN PATENT DOCUMENTS

| WO | 2005116645 | 12/2005 |
| WO | 2010056898 A2 | 5/2010 |

OTHER PUBLICATIONS

Tiller, T., et al., 2008, Efficient generation of monoclonal antibodies from single human B cells by single cell RT-PCR and expression vector cloning, J. Immunol. Methods 329:112-124.*
Liu, F., et al., 2005, Human single-chain antibodies inhibit replication of human immunodeficiency virus type 1 (HIV-1), Aids Res. Human Retrovir. 21(10):876-881.*
Bailey et al, "Neutralizing Antibodies Do Not Mediate Suppression of Human Immunodeficiency Virus Type 1 in Elite Suppressors or Selection of Plasma Virus Variants in Patients on Highly Active Antiretroviral Therapy", "Journal of Virology", May 2006, pp. 4758-4770, vol. 80, No. 10.
Banatvala et al, "Lifelong Protection Against Hepatitis B: The Role of Vaccine Immunogenicity in Immunne Memory", "Vaccine", 2001, pp. 877-885, vol. 19, Publisher: Elsevier.
Bauer et al., "Hepatitis B Surface Antigent-Specific T and B Cell Memory in Individuals Who Had Lost Protective Antibodies After Hepatitis B Vaccination", "Vaccine", 2006, pp. 572-577, vol. 24, No. 5.
Burton et al., "Efficient Neutralization of Primary Isolates of HIV-1 by a Recombinant Human Monoclonal Antiboy", "Science", 1994, pp. 1024-1027, vol. 266, No. 5187.
Decker et al., "Antigenic conservation and immunogenicity of the HIV coreceptor binding site", "J Exp Medicine", May 2, 2005, pp. 1407-1419, vol. 201, No. 9.
Devico et al., "Antibodies to CD4-induced sites in HIV gp120 correlate with the control of SHIV challenge in macaques vaccinated with subunit immunogens", "PNAS", Oct. 30, 2007, pp. 17477-17482, vol. 104, No. 44, Publisher: The National Academy of Sciences of the USA.
Dhillon et al., "Dissecting the Neutralizing Antibody Specificities of Broadly Neutralizing Sera from Human Immunodefiency Virus Type 1-Infected Donors", "Journal of Virology", Jun. 2007, pp. 6548-6562, vol. 81, No. 12, Publisher: American Society for Microbiology.
Gray et al., "Neutralizing Antibody Responses in Acute Human Immunodeficiency Virus Type 1 Subtype C Infection", "Journal of Virology", Jun. 2007, pp. 6187-6196, vol. 81, No. 12, Publisher: American Society for Microbiology.
IB, "International Preliminary Report on Patentability for Corresponding International application No. PCT/US2009/064253", May 17, 2011, pp. 1-6, Publisher: WIPO.
Kwong et al., "Structure of an HIVgp120 envelope glycoprotein in complex with the CD4 receptor and a neutralizing human antibody", "Nature", Jun. 18, 1998, pp. 648-659, vol. 393, No. 6686, Publisher: Macmillan Publishers Ltd.
Lalezari et al., "Safety, Pharmacokinetics, and Antiviral Activity of HGS004, a Novel Fully Human IgG4 Monoclonal Antibody against CCR5, in HIV-1-Infected Patients", "The Journal of Infectious Diseases", Feb. 11, 2008, pp. 721-727, vol. 197, Publisher: the Infectious Diseases Society of America.
Li et al., "Broad HIV-1 neutralization mediated by CD4-binding site antibodies", "Nature Medicine", Aug. 26, 2007, pp. 1032-1034, vol. 13, No. 9

(Continued)

*Primary Examiner* — Jeffrey S. Parkin
(74) *Attorney, Agent, or Firm* — Evans & Molinelli PLLC; Judith Evans

(57) ABSTRACT

The present application provides methods for producing human monoclonal antibodies without using hybridoma technology, antibodies produced used the described methods, and methods for using the antibodies to treat or prevent disease conditions (e.g., infection by pathogens such as the Human Immunodeficiency Virus).

5 Claims, 15 Drawing Sheets

(56) References Cited

OTHER PUBLICATIONS

Moir et al., "Evidence for HIV-associated B cell exhaustion in a dysfunctional memory B cell compartment in HIV-infected viremic individuals", "J. Exp. Med.", Jul. 14, 2008, pp. 1797-1805, vol. 205, No. 8, Publisher: The Rockefeller University Press.

Pereyra et al., "Genetic and Immunologic Heterogeneity among Persons Who Control HIV Infection in the Absence of Therapy", "The Journal of Infectious Diseases", Feb. 5, 2008, pp. 563-571, vol. 197, Publisher: the Infectious Diseases Society of America.

Rizzuto et al., "A Conserved HIV gp120 Glycoprotein Structure Involved in Chemokine Receptor Binding", "Science", Jun. 19, 1998, pp. 1949-1953, vol. 280, No. 5371.

Robinson et al., "High Frequencies of Antibody Response to CD4 Induced Epitopes in HIV infected Patients Started on HAART During Acute Infection", "Human Antibodies", 2005, pp. 115-121, vol. 14, Publisher: IOS Press.

Sajadi et al., "HIV-1 natural viral suppressors: control of viral replication in the absence of therapy", "AIDS", 2007, pp. 517-519, vol. 21, No. 4, Publisher: Lippincott Williams & Wilkins.

Tatanji et al, "Loss of memory B cells impairs maintenance of long-term serologic memory during HIV-1 infection", "Blood", Sep. 1, 2006, pp. 1580-1587, vol. 108, No. 5, Publisher: the American Society of Hematology.

Traggiai et al, "An efficient method to make human monoclonal antibodies from memory B cells: potent neutralization of SARS coronavirus", "Nature Medicine", Aug. 2004, pp. 871-875, vol. 10, No. 8.

Wainwright et al., "Protection Provided by Hepatitis B Vaccine in a Yupik Eskimo Population—Results of a 10-Year Study", "The Journal of Infectious Diseases", 1997, pp. 674-677, vol. 175, No. 3, Publisher: The University of Chicago.

West et al., "Vaccine Induced Immunologic Memory for Hepatitis B Surface Antigen: Implications for Policy on Booster Vaccination", "Vaccine", 1996, pp. 1019-1027, vol. 14, No. 11, Publisher: Elsevier Science Ltd.

Wyatt et al., "The antigenic structure of theHIVgp120 envelope glycoprotein", "Nature", Jun. 18. 1998, pp. 705-711, vol. 393, No. 6686, Publisher: Macmillan Publishers Ltd.

Beerli et al., "Isolation of human monoclonal antibodies by mammalian cell display", "Procedings of the National Academy of Sciences", Sep. 23, 2008, pp. 14331-14341, vol. 105, No. 38, Publisher: National Academy of Sciences, Published in: Washington, DC.

Tiller, T. et al., "Efficient generation of monoclonal antibodies from single human B cells by single cell RT-PCR and expression vector clo", "Journal of Immunological Methods", Oct. 31, 2007, pp. 114-124, vol. 329, No. 1-2, Publisher: Elsevier, Published in: New York, NY.

Kim, "International Search Report Written Opinion", WO2010/056898, May 20, 2010.

* cited by examiner

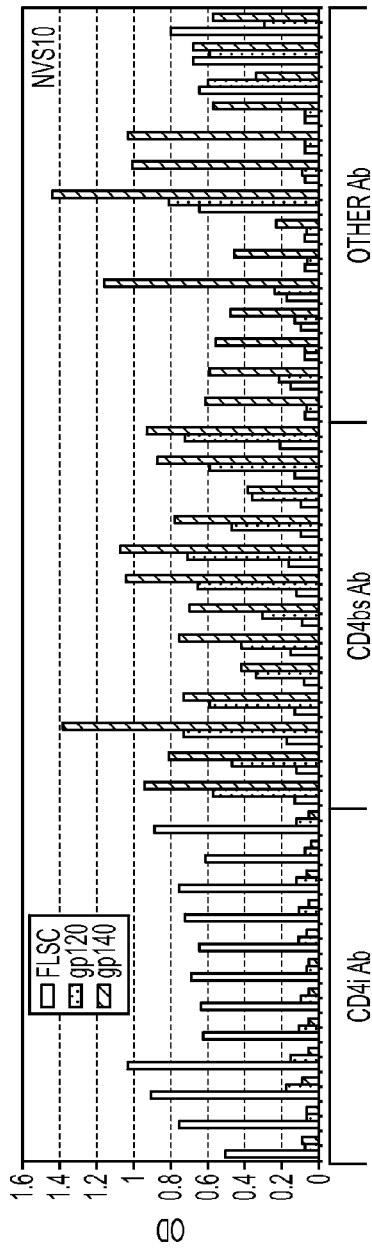
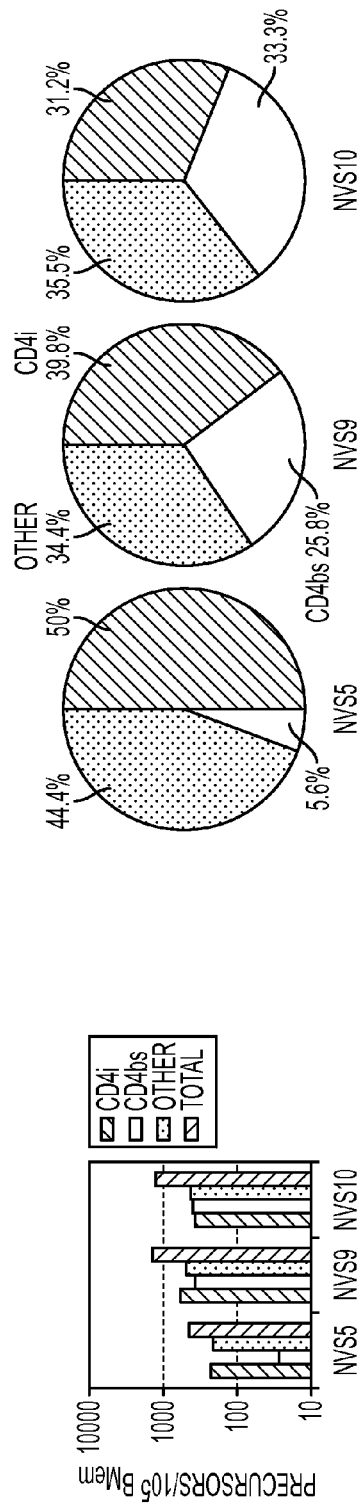
FIG. 2A
FIG. 2B
FIG. 2C

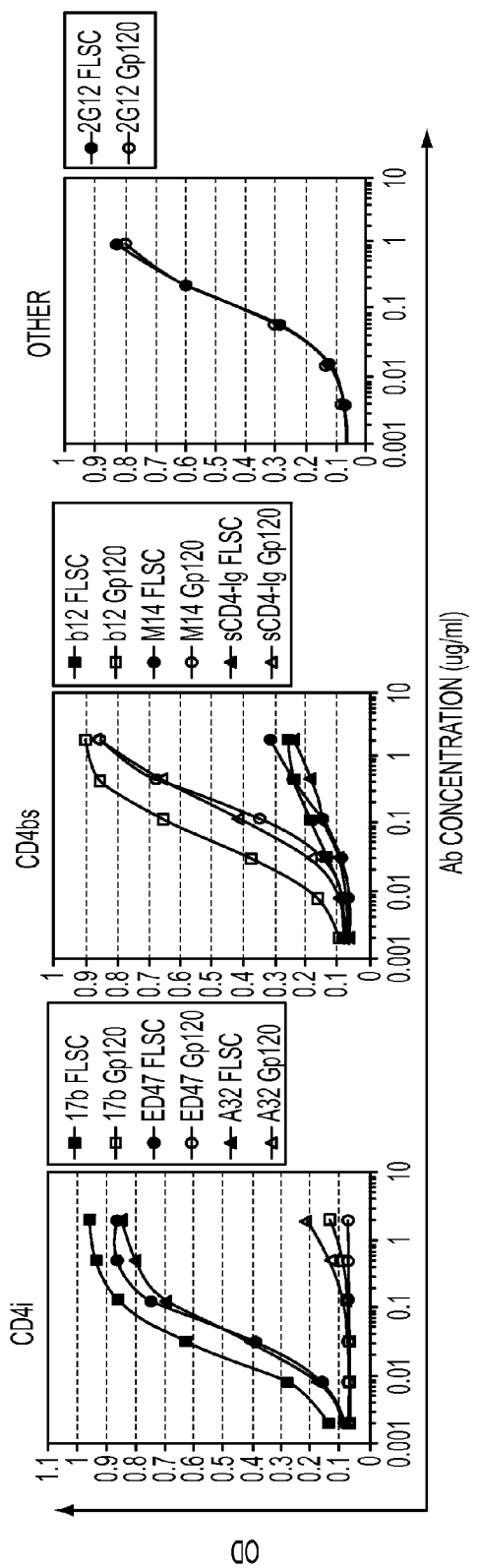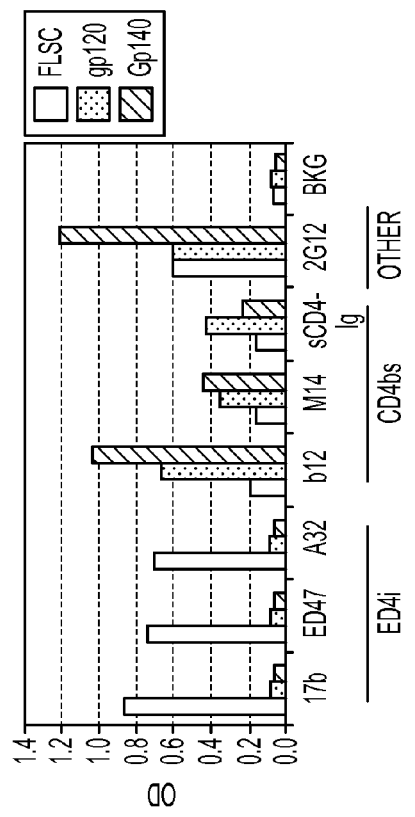
FIG. 5A
FIG. 5B

SEQUENCE LISTING

```
<160> NUMBER OF SEQ ID NOS: 164

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH1/5/7

<400> SEQUENCE: 1
gtgccaccgg tgtacattcc caggtscagc tggtgcartc                             40

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH1-24

<400> SEQUENCE: 2
gtgccaccgg tgtacattcc caggtccagc tggtacagtc                             40

<210> SEQ ID NO 3
<211> LENGTH: 40
<212> TYPE: DNA
```

```
<213> ORGANISM: Artificial Sequence
<220> FEATURE:
<223> OTHER INFORMATION: Synthetic oligonucleotide - 5'VH primer:
      5Age1 VH1-3/18

<400> SEQUENCE: 3
gtgccaccgg tgtacattcc caggtycagc tkgtgcagtc                            40

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH1-17

<400> SEQUENCE: 4
gtgccaccgg tgtacattcc caggttcagc tgttgcagcc                            40

<210> SEQ ID NO 5
<211> LENGTH: 42
<212> TYPE: DNA
<213> ORGANISM: Artificial Sequence
<220> FEATURE:
<223> OTHER INFORMATION: Synthetic oligonucleotide - 5'VH primer:
      5Age1 VH1-45/58

<400> SEQUENCE: 5
gtgccaccgg tgtacattcc caratgcagc tggtgcagtc tg                         42

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH2

<400> SEQUENCE: 6
gtgccaccgg tgtacattcc cagrtcacct tgarggagtc                            40

<210> SEQ ID NO 7
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH3
<220> FEATURE:
<221> NAME/KEY: misc_feature
<222> LOCATION: (29)..(29)
<223> OTHER INFORMATION: n is a, c, g, or t

<400> SEQUENCE: 7
gtgccaccgg tgtacattcc gaggtrcanc tggtggagtc                            40

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH3-23

<400> SEQUENCE: 8
gtgccaccgg tgtacattcc gaggtgcagc tgttggagtc                            40
```

```
<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH3-32

<400> SEQUENCE: 9
gtgccaccgg tgtacattcc gaggtggagc tgatagagtc                              40

<210> SEQ ID NO 10
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH3-33

<400> SEQUENCE: 10
gtgccaccgg tgtacattcc gaggtacagc tcgtggagtc                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH4

<400> SEQUENCE: 11
gtgccaccgg tgtacattcc cagstgcagc tgcaggagtc                              40

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotide - 5'VH primer:
      5Age1 VH4-34

<400> SEQUENCE: 12
gtgccaccgg tgtacattcc caggtgcagc tacarcagtg                              40

<210> SEQ ID NO 13
<211> LENGTH: 42
<212> TYPE: DNA
<213> ORGANISM: Artificial Sequence
<220> FEATURE:
<223> OTHER INFORMATION: Synthetic oligonucleotide - 5'VH primer:
      5Age1 VH6

<400> SEQUENCE: 13
gtgccaccgg tgtacattcc caggtacagc tgcagcagtc ag                           42

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide - 3'VH primer:
      3Sal1 JH1/2/4/5

<400> SEQUENCE: 14
tgcgaagtcg acgctgagga gacrgtgacc agg                                     33

<210> SEQ ID NO 15
```

```
<211> LENGTH: 36
<212> TYPE: DNA
<213> ORGANISM: Artificial Sequence
<220> FEATURE:
<223> OTHER INFORMATION: Synthetic oligonucleotide - 3'VH primer:
      3Sal1 JH3

<400> SEQUENCE: 15
tgcgaagtcg acgctgaaga gacggtgacc attgtc                                36

<210> SEQ ID NO 16
<211> LENGTH: 34
<212> TYPE: DNA
<213> ORGANISM: Artificial Sequence
<220> FEATURE:
<223> OTHER INFORMATION: Synthetic oligonucleotide - 3'VH primer:
      3Sal1 JH6

<400> SEQUENCE: 16
tgcgaagtcg acgctgagga gacggtgacc gtgg                                  34

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide - 3'VH primer:
      3Sal1-JH3*

<400> SEQUENCE: 17
tgcgaagtcg acgctaaaga gacggtgacc actgtc                                36

<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK1

<400> SEQUENCE: 18
ctcacaccgg tgtccactgt gmcatccagw tgacccagtc tc                         42

<210> SEQ ID NO 19
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK1-8/D-43

<400> SEQUENCE: 19
ctcacaccgg tgtccactgt gccatccgga tgacccagtc tc                         42

<210> SEQ ID NO 20
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK1D-8

<400> SEQUENCE: 20
ctcacaccgg tgtccactgt gtcatctgga tgacccagtc tc                         42

<210> SEQ ID NO 21
<211> LENGTH: 42
```

```
<212> TYPE: DNA
<213> ORGANISM: Artificial Sequence
<220> FEATURE:
<223> OTHER INFORMATION: Synthetic oligonucleotide - 5'VK primer:
      5Age1 VK1-22

<400> SEQUENCE: 21
ctcacaccgg tgtccactgt gacatccaga tgactcagyc tc                      42

<210> SEQ ID NO 22
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK2-24

<400> SEQUENCE: 22
ctcacaccgg tgtccactgt gatattgtga tgacccagac tc                      42

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK2-28/30

<400> SEQUENCE: 23
ctcacaccgg tgtccactgt gatrttgtga tgactcagtc tc                      42

<210> SEQ ID NO 24
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK3-7

<400> SEQUENCE: 24
ctcacaccgg tgtccactgt gaaattgtaa tgacacagtc tc                      42

<210> SEQ ID NO 25
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK3-11/20

<400> SEQUENCE: 25
ctcacaccgg tgtccactgt gaaattgtgt tgacrcagtc tc                      42

<210> SEQ ID NO 26
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5Age1 VK3-15

<400> SEQUENCE: 26
ctcacaccgg tgtccactgt gaaatagtga tgaygcagtc tc                      42

<210> SEQ ID NO 27
<211> LENGTH: 40
<212> TYPE: DNA
```

```
<213> ORGANISM: Artificial Sequence
<220> FEATURE:
<223> OTHER INFORMATION: Synthetic oligonucleotide - 5'VK primer:
      5AgeI VK3-34

<400> SEQUENCE: 27
ctcacaccgg tgtccactgt gaagttgtgc tgacatggtc                40

<210> SEQ ID NO 28
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5AgeI VK4-1

<400> SEQUENCE: 28
ctcacaccgg tgtccactgt gacatcgtga tgacccagtc tc             42

<210> SEQ ID NO 29
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5AgeI VK5-2

<400> SEQUENCE: 29
ctcacaccgg tgtccactgt gaaacgacac tcacgcagtc tc             42

<210> SEQ ID NO 30
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5AgeI VK6-21

<400> SEQUENCE: 30
ctcacaccgg tgtccactgt gaaattgtgc tgactcagtc tc             42

<210> SEQ ID NO 31
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5AgeI VK6D-41

<400> SEQUENCE: 31
ctcacaccgg tgtccactgt gatgttgtga tgacacagtc tc             42

<210> SEQ ID NO 32
<211> LENGTH: 42
<212> TYPE: DNA
<213> ORGANISM: Artificial Sequence
<220> FEATURE:
<223> OTHER INFORMATION: Synthetic oligonucleotide - 5'VK primer:
      5AgeI VK7-3

<400> SEQUENCE: 32
ctcacaccgg tgtccactgt gacattgtgc tgacccagtc tc             42

<210> SEQ ID NO 33
<211> LENGTH: 32
<212> TYPE: DNA
<213> ORGANISM: Artificial Sequence
```

<220> FEATURE:
<223> OTHER INFORMATION: Synthetic oligonucleotide - 3'VK primer:
      3BsiWI JK1/4

<400> SEQUENCE: 33
gccaccgtac gtttgatytc caccttggtc cc                                32

<210> SEQ ID NO 34
<211> LENGTH: 32
<212> TYPE: DNA
<213> ORGANISM: Artificial Sequence
<220> FEATURE:
<223> OTHER INFORMATION: Synthetic oligonucleotide - 3'VK primer:
      3BsiWI JK2

<400> SEQUENCE: 34
gccaccgtac gtttgatctc cagcttggtc cc                                32

<210> SEQ ID NO 35
<211> LENGTH: 32
<212> TYPE: DNA
<213> ORGANISM: Artificial Sequence
<220> FEATURE:
<223> OTHER INFORMATION: Synthetic oligonucleotide - 3'VK primer:
      3BsiWI JK3

<400> SEQUENCE: 35
gccaccgtac gtttgatatc cactttggtc cc                                32

<210> SEQ ID NO 36
<211> LENGTH: 32
<212> TYPE: DNA
<213> ORGANISM: Artificial Sequence
<220> FEATURE:
<223> OTHER INFORMATION: Synthetic oligonucleotide - 3'VK primer:
      3BsiWI JK5

<400> SEQUENCE: 36
gccaccgtac gtttaatctc cagtcgtgtc cc                                32

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5AgeI VL1a

<400> SEQUENCE: 37
gactcaccgg tgtcctctcc cagtctgtgc tgactcagcc                        40

<210> SEQ ID NO 38
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5AgeI VL1b

<400> SEQUENCE: 38
gactcaccgg tgtcctctcc cagtctgtgy tgacgcagcc                        40

<210> SEQ ID NO 39
<211> LENGTH: 40
<212> TYPE: DNA
<213> ORGANISM: Artificial Sequence
<220> FEATURE:

```
<223> OTHER INFORMATION: Synthetic oligonucleotide - 5'VL primer:
      5Age1 VL1c

<400> SEQUENCE: 39
gactcaccgg tgtcctctcc cagtctgtcg tgacgcagcc                              40

<210> SEQ ID NO 40
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL2

<400> SEQUENCE: 40
gactcaccgg tgtcctctcc cartctgccc tgactcagcc                              40

<210> SEQ ID NO 41
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL2-34

<400> SEQUENCE: 41
gactcaccgg tgtcctctcc cagtctgttc tgactcagcc                              40

<210> SEQ ID NO 42
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL2-5

<400> SEQUENCE: 42
gactcaccgg tgtcctctcc cagtctgccc tgattcagcc                              40

<210> SEQ ID NO 43
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL3a

<400> SEQUENCE: 43
gactcaccgg tgtcctctcc tcctatgwgc tgactcagcc                              40

<210> SEQ ID NO 44
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL3b

<400> SEQUENCE: 44
gactcaccgg tgtcctctcc tcctatgagc tgacacagcc                              40

<210> SEQ ID NO 45
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
```

5Age1 VL3c

<400> SEQUENCE: 45
gactcaccgg tgtcctctcc tcttctgagc tgactcagga         40

<210> SEQ ID NO 46
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL3d

<400> SEQUENCE: 46
gactcaccgg tgtcctctcc tcctatgagc tgatgcagcc         40

<210> SEQ ID NO 47
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL3e

<400> SEQUENCE: 47
gactcaccgg tgtcctctcc tcctctgggc caactcaggt         40

<210> SEQ ID NO 48
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL4

<400> SEQUENCE: 48
gactcaccgg tgtcctctcc cagcytgtgc tgactcaatc         40

<210> SEQ ID NO 49
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL5

<400> SEQUENCE: 49
gactcaccgg tgtcctctcc cagsctgtgc tgactcagcc         40

<210> SEQ ID NO 50
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL4/9

<400> SEQUENCE: 50
gactcaccgg tgtcctctcc ctgcctgtgc tgactcagcc         40

<210> SEQ ID NO 51
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL6

```
<400> SEQUENCE: 51
gactcaccgg tgtcctctcc aattttatgc tgactcagcc                    40

<210> SEQ ID NO 52
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL7

<400> SEQUENCE: 52
gactcaccgg tgtcctctcc cagrctgtgg tgactcagga                    40

<210> SEQ ID NO 53
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL8

<400> SEQUENCE: 53
gactcaccgg tgtcctctcc cagactgtgg tgacccagga                    40

<210> SEQ ID NO 54
<211> LENGTH: 41
<212> TYPE: DNA
<213> ORGANISM: Artificial Sequence
<220> FEATURE:
<223> OTHER INFORMATION: Synthetic oligonucleotide - 5'VL primer:
      5Age1 VL10

<400> SEQUENCE: 54
gactcaccgg tgtcctctcc caggcagggc tgactcagcc a                  41

<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide - 5'VL primer:
      5Age1 VL11

<400> SEQUENCE: 55
gactcaccgg tgtcctctcc cggcccgtgc tgactcagcc                    40

<210> SEQ ID NO 56
<211> LENGTH: 28
<212> TYPE: DNA
<213> ORGANISM: Artificial Sequence
<220> FEATURE:
<223> OTHER INFORMATION: Synthetic oligonucleotide - 3'VL primer:
      3'Xho1-CL

<400> SEQUENCE: 56
ctctactcga gggygggaac agagtgac                                 28

<210> SEQ ID NO 57
<211> LENGTH: 34
<212> TYPE: DNA
<213> ORGANISM: Artificial Sequence
<220> FEATURE:
<223> OTHER INFORMATION: Synthetic oligonucleotide - Alternative 3'
      primer: 3'IgG-VH-NheI
```

<400> SEQUENCE: 57
ggagggtgct agcgggaaga csgatgggcc cttg         34

<210> SEQ ID NO 58
<211> LENGTH: 37
<212> TYPE: DNA
<213> ORGANISM: Artificial Sequence
<220> FEATURE:
<223> OTHER INFORMATION: Synthetic oligonucleotide - Alternative 3'
      primer: 3'Ig-CKstop

<400> SEQUENCE: 58
gtgtgcggcc gctcaacact ctcccctgtt gaagctc      37

<210> SEQ ID NO 59
<211> LENGTH: 40
<212> TYPE: DNA
<213> ORGANISM: Artificial Sequence
<220> FEATURE:
<223> OTHER INFORMATION: Synthetic oligonucleotide - Alternative 3'
      primer: 3'Ig-CLstop1

<400> SEQUENCE: 59
gtgtgcggcc gctcatgaac attctgyagg ggccactgtc   40

<210> SEQ ID NO 60
<211> LENGTH: 40
<212> TYPE: DNA
<213> ORGANISM: Artificial Sequence
<220> FEATURE:
<223> OTHER INFORMATION: Synthetic oligonucleotide - Alternative 3'
      primer: 3'Ig-CLstop2

<400> SEQUENCE: 60
gtgtgcggcc gctcatgaac attccgtagg ggcmactgtc   40

<210> SEQ ID NO 61
<211> LENGTH: 39
<212> TYPE: DNA
<213> ORGANISM: Artificial Sequence
<220> FEATURE:
<223> OTHER INFORMATION: Synthetic oligonucleotide - Alternative 3'
      primer: 3'IgG-Cstop

<400> SEQUENCE: 61
gtgtgcggcc gctcatttac ccrgagacag ggagaggct    39

<210> SEQ ID NO 62
<211> LENGTH: 43
<212> TYPE: DNA
<213> ORGANISM: Artificial Sequence
<220> FEATURE:
<223> OTHER INFORMATION: Synthetic oligonucleotide - Alternative 3'
      primer: 3'IgA-Cstop

<400> SEQUENCE: 62
gtgtgcggcc gctcagtagc aggtgccgtc cacctccgcc atg   43

<210> SEQ ID NO 63
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 63

```
cttcccgcta gcaccctcct ccaagagcac                                         30
```

<210> SEQ ID NO 64
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 64

```
ggagggtgct agcgggaaga csgatgggcc cttg                                    34
```

<210> SEQ ID NO 65
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 65

```
gtggaagctt gcggccgctc atttacccrg agacagggac aggct                        45
```

<210> SEQ ID NO 66
<211> LENGTH: 6075
<212> TYPE: DNA
<213> ORGANISM: Artificial Sequence
<220> FEATURE:
<223> OTHER INFORMATION: Synthetic expression vector

<400> SEQUENCE: 66

```
cgaattaatt cgagctcgcc cgacattgat tattgactag ttattaatag taatcaatta        60
cggggtcatt agttcatagc ccatatatgg agttccgcgt tacataactt acggtaaatg      120
gcccgcctgg ctgaccgccc aacgaccccc gcccattgac gtcaataatg acgtatgttc      180
ccatagtaac gccaataggg actttccatt gacgtcaatg ggtggagtat ttacggtaaa      240
ctgcccactt ggcagtacat caagtgtatc atatgccaag tacgccccct attgacgtca      300
atgacggtaa atggcccgcc tggcattatg cccagtacat gaccttatgg gactttccta      360
cttggcagta catctacgta ttagtcatcg ctattaccat ggtgatgcgg ttttggcagt      420
acatcaatgg gcgtggatag cggtttgact cacggggatt tccaagtctc cacccattg       480
acgtcaatgg gagtttgttt tggcaccaaa atcaacggga ctttccaaaa tgtcgtaaca      540
actccgcccc attgacgcaa atgggcggta ggcgtgtacg gtgggaggtc tatataagca      600
gagctcgttt agtgaaccgt cagatcgcct ggagacgcca tccacgctgt tttgacctcc      660
atagaagaca ccgggaccga tccagcctcc gcggccggga acggtgcatt ggaacgcgga      720
ttccccgtgc caagagtgac gtaagtaccg cctatagagt ctataggccc acccccttgg      780
cttcgttaga acgcggctac aattaataca taaccttatg tatcatacac atacgattta      840
ggtgacacta tagaataaca tccactttgc ctttctctcc acaggtgtcc actcccaggt      900
ccaactgcac ctcggttcta tcgattgaat tccaccatgg gatggtcatg tatcatcctt      960
tttctagtag caactgccac cggtgtacat tcccaggtgc agctggtgca gtctgggcct     1020
gacatgaaga agcctgggc ctcagtgaag gtctcctgca aggtttccgg atacaccctc      1080
actgaagtaa ccatgcactg ggtgcgacag gctcctggaa aagggcttga gtggatggga     1140
ggttttgatc ttgaagatgg tgaaacaatc tacgcacaga gttccagggc agagtcacc      1200
atgaccgagg acacatccac agacacagcc tacatggagc tcagcagcct gagatctgag     1260
gacacggccg tgtattactg tgcaacaaaa cccctacgaa attttgactg gtcccggcgg     1320
```

```
ggtgactacg gtatggacgt ctggggccaa gggacaatgg tcaccgtctc ttcagcgtcg    1380
accaagggcc catcggtctt cccgctagca ccctcctcca agagcacctc tgggggcaca    1440
gcggccctgg gctgcctggt caaggactac ttccccgaac tgtgacggt ctcgtggaac     1500 tcaggcgccc tgaccagcgg cgtgcacacc ttccccggctg tcctacagtc ctcaggactc   1560
tactccctca gcagcgtggt gaccgtgccc tccagcagct gggcaccca gacctacatc     1620 tgcaacgtga atcacaagcc cagcaacacc aaggtggaca agagagttga gcccaaatct    1680
tgtgacaaaa ctcacacatg cccaccgtgc ccagcacctg aactcctggg gggaccgtca    1740
gtcttcctct tccccccaaa acccaaggac accctcatga tctcccggac ccctgaggtc    1800
acatgcgtgg tggtggacgt gagccacgaa gaccctgagg tcaagttcaa ctggtacgtg    1860
gacggcgtgg aggtgcataa tgccaagaca aagccgcggg aggagcagta caacagcacg    1920
taccgtgtgg tcagcgtcct caccgtcctg caccaggact ggctgaatgg caaggagtac    1980
aagtgcaagg tctccaacaa agccctccca gcccccatcg agaaaaccat ctccaaagcc    2040
aaagggcagc cccgagaacc acaggtgtac accctgcccc catcccggga ggagatgacc    2100
aagaaccagg tcagcctgac ctgcctggtc aaaggcttct atcccagcga catcgccgtg    2160
gagtgggaga gcaatgggca gccggagaac aactacaaga ccacgcctcc cgtgctggac    2220
tccgacggct ccttcttcct ctatagcaag ctcaccgtgg acaagagcag gtggcagcag    2280
gggaacgtct tctcatgctc cgtgatgcat gaggctctgc acaaccacta cacgcagaag    2340
agcctctccc tgtccccggg taaatgagcg gccgcaagct tggccgccat ggcccaactt    2400
gtttattgca gcttataatg gttacaaata aagcaatagc atcacaaatt tcacaaataa    2460
agcatttttt tcactgcatt ctagttgtgg tttgtccaaa ctcatcaatg tatcttatca    2520
tgtctggatc gggaattaat tcggcgcagc accatggcct gaaataacct ctgaaagagg    2580
aacttggtta ggtaccttct gaggcggaaa gaaccatctg tggaatgtgt gtcagttagg    2640
gtgtggaaag tccccaggct ccccagcagg cagaagtatg caaagcatgc atctcaatta    2700
gtcagcaacc aggtgtggaa agtccccagg ctccccagca ggcagaagta tgcaaagcat    2760
gcatctcaat tagtcagcaa ccatagtccc gcccctaact ccgcccatcc cgcccctaac    2820
tccgcccagt tccgcccatt ctccgcccca tggctgacta attttttta tttatgcaga    2880 ggccgaggcc gcctcggcct ctgagctatt ccagaagtag tgaggaggct ttttggagg    2940 cctaggcttt tgcaaaaagc tgttaacagc ttggcactgg ccgtcgtttt acaacgtcgt    3000
gactgggaaa accctggcgt tacccaactt aatcgccttg cagcacatcc cccttcgcc    3060 agttggcgta atagcgaaga ggcccgcacc gatcgccctt cccaacagtt gcgcagcctg    3120
aatggcgaat ggcgcctgat gcggtatttt ctccttacgc atctgtgcgg tatttcacac    3180
cgcatacgtc aaagcaacca tagtacgcgc cctgtagcgg cgcattaagc gcggcgggtg    3240
tggtggttac gcgcagcgtg accgctacac ttgccagcgc cctagcgccc gctcctttcg    3300
ctttcttccc ttcctttctc gccacgttcg ccggctttcc ccgtcaagct ctaaatcggg    3360
ggctcccttt agggttccga tttagtgctt tacggcacct cgaccccaaa aaacttgatt    3420
tgggtgatgg ttcacgtagt gggccatcgc cctgatagac ggttttttcgc cctttgacgt    3480 tggagtccac gttctttaat agtggactct tgttccaaac tggaacaaca ctcaacccta    3540
tctcgggcta ttcttttgat ttataaggga ttttgccgat ttcggcctat tggttaaaaa    3600
atgagctgat ttaacaaaaa tttaacgcga attttaacaa aatattaacg tttacaattt    3660
```

```
tatggtgcac tctcagtaca atctgctctg atgccgcata gttaagccag ccccgacacc      3720
cgccaacacc cgctgacgcg ccctgacggg cttgtctgct ccggcatccg cttacagaca      3780
agctgtgacc gtctccggga gctgcatgtg tcagaggttt tcaccgtcat caccgaaacg      3840
cgcgagacga aagggcctcg tgatacgcct attttatag gttaatgtca tgataataat       3900
ggtttcttag acgtcaggtg gcacttttcg gggaaatgtg cgcggaaccc ctatttgttt      3960 attttctaa atacattcaa atatgtatcc gctcatgaga caataaccct gataaatgct       4020
tcaataatat tgaaaagga agagtatgag tattcaacat ttccgtgtcg cccttattcc       4080
cttttttgcg gcatttttgcc ttcctgtttt tgctcaccca gaaacgctgg tgaaagtaaa     4140
agatgctgaa gatcagttgg gtgcacgagt gggttacatc gaactggatc tcaacagcgg      4200
taagatcctt gagagttttc gccccgaaga acgttttcca atgatgagca cttttaaagt      4260
tctgctatgt ggcgcggtat tatcccgtat tgacgccggg caagagcaac tcggtcgccg      4320
catacactat tctcagaatg acttggttga gtactcacca gtcacagaaa agcatcttac      4380
ggatggcatg acagtaagag aattatgcag tgctgccata accatgagtg ataacactgc      4440
ggccaactta cttctgacaa cgatcggagg accgaaggag ctaaccgctt ttttgcacaa      4500
catgggggat catgtaactc gccttgatcg ttgggaaccg gagctgaatg aagccatacc      4560
aaacgacgag cgtgacacca cgatgcctgt agcaatggca acaacgttgc gcaaactatt      4620
aactggcgaa ctacttactc tagcttcccg gcaacaatta atagactgga tggaggcgga      4680
taaagttgca ggaccacttc tgcgctcggc ccttccggct ggctggttta ttgctgataa      4740
atctggagcc ggtgagcgtg ggtctcgcgg tatcattgca gcactggggc cagatggtaa      4800
gccctcccgt atcgtagtta tctacacgac ggggagtcag gcaactatgg atgaacgaaa      4860
tagacagatc gctgagatag gtgcctcact gattaagcat tggtaactgt cagaccaagt      4920
ttactcatat atactttaga ttgatttaaa acttcatttt taatttaaaa ggatctaggt      4980
gaagatcctt tttgataatc tcatgaccaa atcccttaa cgtgagtttt cgttccactg        5040
agcgtcagac cccgtagaaa agatcaaagg atcttcttga gatcctttt ttctgcgcgt       5100 aatctgctgc ttgcaaacaa aaaaaccacc gctaccagcg gtggtttgtt tgccggatca      5160
agagctacca actctttttc cgaaggtaac tggcttcagc agagcgcaga taccaaatac      5220
tgttcttcta gtgtagccgt agttaggcca ccacttcaag aactctgtag caccgcctac      5280
atacctcgct ctgctaatcc tgttaccagt ggctgctgcc agtggcgata agtcgtgtct      5340
taccgggttg gactcaagac gatagttacc ggataaggcg cagcggtcgg gctgaacggg      5400
gggttcgtgc acacagccca gcttggagcg aacgacctac accgaactga gatacctaca      5460
gcgtgagcta tgagaaagcg ccacgccttc ccgaagggag aaaggcggac aggtatccgg      5520
taagcggcag ggtcggaaca ggagagcgca cgagggagct tccaggggga aacgcctggt      5580
atctttatag tcctgtcggg tttcgccacc tctgacttga gcgtcgattt ttgtgatgct      5640 cgtcagggg gcggagccta tggaaaaacg ccagcaacgc ggccttttta cggttcctgg       5700
ccttttgctg gccttttgct cacatgttct ttcctgcgtt atcccctgat tctgtggata      5760
accgtattac cgcctttgag tgagctgata ccgctcgccg cagccgaacg accgagcgca      5820
gcgagtcagt gagcgaggaa gcggaagagc gcccaatacg caaaccgcct ctccccgcgc      5880
gttggccgat tcattaatcc aactggcacg acaggtttcc cgactggaaa gcgggcagtg      5940
agcgcaacgc aattaatgtg agttagctca ctcattaggc accccaggct ttacacttta      6000
tgcttccggc tcgtatgttg tgtggaattg tgagcggata acaatttcac acaggaaaca      6060
```
gctatgacat gatta                                                        6075

<210> SEQ ID NO 67
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 67
ggadatyaaa cgtacggtgg ctgcaccatc                                          30

<210> SEQ ID NO 68
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 68
gtggaagctt gcggccgcct aacactctcc cctgttgaag                               40

<210> SEQ ID NO 69
<211> LENGTH: 5350
<212> TYPE: DNA
<213> ORGANISM: Artificial Sequence
<220> FEATURE:
<223> OTHER INFORMATION: Synthetic expression vector

<400> SEQUENCE: 69
cgaattaatt cgagctcgcc cgacattgat tattgactag ttattaatag taatcaatta         60
cggggtcatt agttcatagc ccatatatgg agttccgcgt tacataactt acggtaaatg        120
gcccgcctgg ctgaccgccc aacgaccccc gcccattgac gtcaataatg acgtatgttc        180
ccatagtaac gccaataggg actttccatt gacgtcaatg ggtggagtat ttacggtaaa        240
ctgcccactt ggcagtacat caagtgtatc atatgccaag tacgcccccct attgacgtca       300 atgacggtaa atggcccgcc tggcattatg cccagtacat gaccttatgg gactttccta       360
cttggcagta catctacgta ttagtcatcg ctattaccat ggtgatgcgg ttttggcagt        420
acatcaatgg gcgtggatag cggtttgact cacggggatt tccaagtctc caccccattg        480
acgtcaatgg gagtttgttt tggcaccaaa atcaacggga ctttccaaaa tgtcgtaaca        540
actccgcccc attgacgcaa atgggcggta ggcgtgtacg gtgggaggtc tatataagca        600
gagctcgttt agtgaaccgt cagatcgcct ggagacgcca tccacgctgt tttgacctcc        660
atagaagaca cccgggaccga tccagcctcc gcggccggga acggtgcatt ggaacgcgga       720
ttccccgtgc caagagtgac gtaagtaccg cctatagagt ctataggccc accccccttgg      780 cttcgttaga acgcggctac aattaataca taaccttatg tatcatacac atacgattta       840
ggtgacacta tagaataaca tccactttgc ctttctctcc acaggtgtcc actcccaggt       900
ccaactgcac ctcggttcta tcgattgaat tccaccatgg gatggtcatg tatcatcctt      960
tttctagtag caactgccac cggtgtacat tcagaaattg tgttgacgca gtctccaggc     1020
accctgtctt tgtctccagg ggaaagagcc actctctcct gcagggccag tcagagtgtt     1080
ggcaacaact acttaggctg gtaccagcag aaacctggcc aggctcccag gctgctcatc     1140
tttggtgcat ccaccagggc cactgacatc ccagagaggt ttagtggcag tcggtctggg     1200
acagacttca ctctcaccat cagcagactg gaacctgaag attttgcggt ttattattgt     1260

-continued

```
cagcagtatg ccaattcacc gatcaccttc ggccaaggga cacgactgga gattaaacgt   1320
acggtggctg caccatctgt cttcatcttc ccgccatctg atgagcagtt gaaatctgga   1380
actgcctctg ttgtgtgcct gctgaataac ttctatccca gagaggccaa agtacagtgg   1440
aaggtggata acgccctcca atcgggtaac tcccaggaga gtgtcacaga gcaggacagc   1500
aaggacagca cctacagcct cagcagcacc ctgacgctga gcaaagcaga ctacgagaaa   1560
cacaaagtct acgcctgcga agtcacccat cagggcctga gctcgcccgt cacaaagagc   1620
ttcaacaggg gagagtgttg aggcggccgc aagcttggcc gccatggccc aacttgttta   1680
ttgcagctta taatggttac aaataaagca atagcatcac aaatttcaca aataaagcat   1740
ttttttcact gcattctagt tgtggtttgt ccaaactcat caatgtatct tatcatgtct   1800
ggatcgggaa ttaattcggc gcagcaccat ggcctgaaat aacctctgaa agaggaactt   1860
ggttaggtac cttctgaggc ggaaagaacc atctgtggaa tgtgtgtcag ttagggtgtg   1920
gaaagtcccc aggctcccca gcaggcagaa gtatgcaaag catgcatctc aattagtcag   1980
caaccaggtg tggaaagtcc ccaggctccc cagcaggcag aagtatgcaa agcatgcatc   2040
tcaattagtc agcaaccata gtcccgcccc taactccgcc catccgccc ctaactccgc    2100 ccagttccgc ccattctccg ccccatggct gactaatttt ttttatttat gcagaggccg   2160
aggccgcctc ggcctctgag ctattccaga gtagtgagg aggcttttt ggaggcctag    2220 gcttttgcaa aaagctgtta acagcttggc actggccgtc gttttacaac gtcgtgactg   2280
ggaaaaccct ggcgttaccc aacttaatcg ccttgcagca catcccctt tcgccagttg    2340 gcgtaatagc gaagaggccc gcaccgatcg cccttcccaa cagttgcgca gcctgaatgg   2400
cgaatggcgc ctgatgcggt attttctcct tacgcatctg tgcggtattt cacaccgcat   2460
acgtcaaagc aaccatagta gcgcccctgt agcggcgcat taagcgcggc gggtgtggtg   2520
gttacgcgca gcgtgaccgc tacacttgcc agcgccctag cgcccgctcc tttcgctttc   2580
ttcccttcct ttctcgccac gttcgccggc tttccccgtc aagctctaaa tcggggctc    2640 cctttagggt tccgatttag tgctttacgg cacctcgacc ccaaaaaact tgatttgggt   2700
gatggttcac gtagtgggcc atcgccctga tagacggttt ttcgcccttt gacgttggag   2760
tccacgttct ttaatagtgg actcttgttc caaactggaa caacactcaa ccctatctcg   2820
ggctattctt ttgatttata agggattttg ccgatttcgg cctattggtt aaaaaatgag   2880
ctgatttaac aaaaatttaa cgcgaatttt aacaaaatat taacgtttac aattttatgg   2940
tgcactctca gtacaatctg ctctgatgcc gcatagttaa gccagccccg acacccgcca   3000
acacccgctg acgcgccctg acgggcttgt ctgctcccgg catccgctac agacaagctg   3060
tgaccgtctc cgggagctgc atgtgtcaga ggttttcacc gtcatcaccg aaacgcgcga   3120
gacgaaaggg cctcgtgata cgcctatttt tataggttaa tgtcatgata ataatggttt   3180
cttagacgtc aggtggcact tttcggggaa atgtgcgcgg aacccctatt tgtttatttt   3240
tctaaataca ttcaaatatg tatccgctca tgagacaata accctgataa atgcttcaat   3300
aatattgaaa aaggaagagt atgagtattc aacatttccg tgtcgccctt attccctttt   3360
ttgcggcatt ttgccttcct gtttttgctc acccagaaac gctggtgaaa gtaaaagatg   3420
ctgaagatca gttgggtgca cgagtgggtt acatcgaact ggatctcaac agcggtaaga   3480
tccttgagag ttttcgcccc gaagaacgtt ttccaatgat gagcactttt aaagttctgc   3540
tatgtggcgc ggtattatcc cgtattgacg ccgggcaaga gcaactcggt cgccgcatac   3600
actattctca gaatgacttg gttgagtact caccagtcac agaaaagcat cttacggatg   3660
```

```
gcatgacagt aagagaatta tgcagtgctg ccataaccat gagtgataac actgcggcca    3720
acttacttct gacaacgatc ggaggaccga aggagctaac cgcttttttg cacaacatgg    3780
gggatcatgt aactcgcctt gatcgttggg aaccggagct gaatgaagcc ataccaaacg    3840
acgagcgtga caccacgatg cctgtagcaa tggcaacaac gttgcgcaaa ctattaactg    3900
gcgaactact tactctagct tcccggcaac aattaataga ctggatggag gcggataaag    3960
ttgcaggacc acttctgcgc tcggcccttc cggctggctg gtttattgct gataaatctg    4020
gagccggtga gcgtgggtct cgcggtatca ttgcagcact ggggccagat ggtaagccct    4080
cccgtatcgt agttatctac acgacgggga gtcaggcaac tatggatgaa cgaaatagac    4140
agatcgctga gataggtgcc tcactgatta agcattggta actgtcagac caagtttact    4200
catatatact ttagattgat ttaaaacttc attttttaatt taaaaggatc taggtgaaga    4260
tcctttttga taatctcatg accaaaatcc cttaacgtga gttttcgttc cactgagcgt    4320
cagaccccgt agaaaagatc aaaggatctt cttgagatcc ttttttttctg cgcgtaatct    4380 gctgcttgca acaaaaaaaa ccaccgctac cagcggtggt ttgtttgccg gatcaagagc    4440
taccaactct ttttccgaag gtaactggct tcagcagagc gcagatacca atactgttc    4500 ttctagtgta gccgtagtta ggccaccact tcaagaactc tgtagcaccg cctacatacc    4560
tcgctctgct aatcctgtta ccagtggctg ctgccagtgg cgataagtcg tgtcttaccg    4620
ggttggactc aagacgatag ttaccggata aggcgcagcg gtcgggctga acggggggtt    4680
cgtgcacaca gcccagcttg gagcgaacga cctacaccga actgagatac ctacagcgtg    4740
agctatgaga aagcgccacg ccttcccgaa gggagaaagg cggacaggta tccggtaagc    4800
ggcagggtcg gaacaggaga gcgcacgagg gagcttccag ggggaaacgc ctggtatctt    4860
tatagtcctg tcgggtttcg ccacctctga cttgagcgtc gatttttgtg atgctcgtca    4920
ggggggcgga gcctatggaa aaacgccagc aacgcggcct ttttacggtt cctggccttt    4980
tgctggcctt ttgctcacat gttctttcct gcgttatccc ctgattctgt ggataaccgt    5040
attaccgcct ttgagtgagc tgataccgct cgccgcagcc gaacgaccga gcgcagcgag    5100
tcagtgagcg aggaagcgga agagcgccca atacgcaaac cgcctctccc cgcgcgttgg    5160
ccgattcatt aatccaactg gcacgacagg tttcccgact ggaaagcggg cagtgagcgc    5220
aacgcaatta atgtgagtta gctcactcat taggcacccc aggctttaca ctttatgctt    5280
ccggctcgta tgttgtgtgg aattgtgagc ggataacaat ttcacacagg aaacagctat    5340
gacatgatta                                                          5350

<210> SEQ ID NO 70
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 70
gtcactctgt tcccrccctc gagtgaggag cttcaagcc                           39

<210> SEQ ID NO 71
<211> LENGTH: 46
<212> TYPE: DNA
<213> ORGANISM: Artificial Sequence
<220> FEATURE:
<223> OTHER INFORMATION: Synthetic oligonucleotide
```

<400> SEQUENCE: 71

```
gtggaagctt gcggccgctc atgaacattc tgyaggggcc actgtc            46
```

<210> SEQ ID NO 72
<211> LENGTH: 5352
<212> TYPE: DNA
<213> ORGANISM: Artificial Sequence
<220> FEATURE:
<223> OTHER INFORMATION: Synthetic expression vector

<400> SEQUENCE: 72

```
cgaattaatt cgagctcgcc cgacattgat tattgactag ttattaatag taatcaatta    60
cggggtcatt agttcatagc ccatatatgg agttccgcgt tacataactt acggtaaatg   120
gcccgcctgg ctgaccgccc aacgacccccc gcccattgac gtcaataatg acgtatgttc   180
ccatagtaac gccaataggg actttccatt gacgtcaatg ggtggagtat ttacggtaaa   240
ctgcccactt ggcagtacat caagtgtatc atatgccaag tacgccccct attgacgtca   300
atgacggtaa atggcccgcc tggcattatg cccagtacat gaccttatgg gactttccta   360
cttggcagta catctacgta ttagtcatcg ctattaccat ggtgatgcgg ttttggcagt   420
acatcaatgg gcgtggatag cggtttgact cacggggatt tccaagtctc cacccccattg   480
acgtcaatgg gagtttgttt tggcaccaaa atcaacggga ctttccaaaa tgtcgtaaca   540
actccgcccc attgacgcaa atgggcggta ggcgtgtacg gtgggaggtc tatataagca   600
gagctcgttt agtgaaccgt cagatcgcct ggagacgcca tccacgctgt tttgacctcc   660
atagaagaca ccgggaccga tccagcctcc gcggccggga acggtgcatt ggaacgcgga   720
ttccccgtgc caagagtgac gtaagtaccg cctatagagt ctataggccc acccccttgg   780
cttcgttaga acgcggctac aattaataca taaccttatg tatcatacac atacgattta   840
ggtgacacta tagaataaca tccactttgc ctttctctcc acaggtgtcc actcccaggt   900
ccaactgcac ctcggttcta tcgattgaat tccaccatgg gatggtcatg tatcatcctt   960
tttctagtag caactgccac cggtgtcctc tcccagtctg tgttgacgca gcctccctcc  1020
gcgtccgggt ctcctggaca gtcagtcacc atctcctgca ctggaaccag cagtgacgtt  1080
ggtggttata actatgtttc ctggtaccaa caccacccag gcaaagcccc caaactcata  1140
atttctgagg tcaataaccg gccctcaggg gtccctgatc gtttctctgg ctccaagtct  1200
ggcaacacgg cctccctgac cgtctctggg ctccaggctg aggatgaggc tgaatattac  1260
tgcagctcat acacagacat ccacaatttc gtcttcggcg gagggaccaa gctgaccgtc  1320
ctaggtcagc ccaaggctgc cccctcggtc actctgttcc caccctcgag tgaggagctt  1380
caagccaaca ggccacact ggtgtgtctc ataagtgact tctacccggg agccgtgaca  1440
gtggcctgga aggcagatag cagccccgtc aaggcgggag tggagaccac cacaccctcc  1500
aaacaaagca caacaagta cgcggccagc agctacctga gcctgacgcc tgagcagtgg  1560
aagtcccaca gaagctacag ctgccaggtc acgcatgaag ggagcaccgt ggagaagaca  1620
gtggccccta cagaatgttc atgagcggcc gcaagcttgg ccgccatggc caacttgtt  1680
tattgcagct tataatggtt acaaataaag caatagcatc acaaatttca caaataaagc  1740
atttttttca ctgcattcta gttgtggttt gtccaaactc atcaatgtat cttatcatgt  1800
ctggatcggg aattaattcg gcgcagcacc atggcctgaa ataacctctg aagaggaac   1860
ttggttaggt accttctgag gcggaaagaa ccatctgtgg aatgtgtgtc agttagggtg  1920
tggaaagtcc ccaggctccc cagcaggcag aagtatgcaa agcatgcatc tcaattagtc  1980
```

-continued

```
agcaaccagg tgtggaaagt ccccaggctc cccagcaggc agaagtatgc aaagcatgca   2040
tctcaattag tcagcaacca tagtcccgcc cctaactccg cccatcccgc ccctaactcc   2100
gcccagttcc gcccattctc cgccccatgg ctgactaatt ttttttattt atgcagaggc   2160
cgaggccgcc tcggcctctg agctattcca gaagtagtga ggaggctttt ttggaggcct   2220
aggcttttgc aaaaagctgt taacagcttg gcactggccg tcgttttaca acgtcgtgac   2280
tgggaaaacc ctggcgttac ccaacttaat cgccttgcag cacatccccc tttcgccagt   2340
tggcgtaata gcgaagaggc ccgcaccgat cgcccttccc aacagttgcg cagcctgaat   2400
ggcgaatggc gcctgatgcg gtattttctc cttacgcatc tgtgcggtat ttcacaccgc   2460
atacgtcaaa gcaaccatag tacgcgccct gtagcggcgc attaagcgcg gcgggtgtgg   2520
tggttacgcg cagcgtgacc gctacacttg ccagcgccct agcgcccgct cctttcgctt   2580
tcttcccttc ctttctcgcc acgttcgccg gctttccccg tcaagctcta atcgggggc    2640 tcccttagg gttccgattt agtgctttac ggcacctcga ccccaaaaaa cttgatttgg    2700
gtgatggttc acgtagtggg ccatcgccct gatagacggt ttttcgccct tgacgttgg    2760 agtccacgtt ctttaatagt ggactcttgt tccaaactgg aacaacactc aaccctatct   2820
cgggctattc ttttgattta aagggatttt gccgatttc ggcctattgg ttaaaaaatg    2880
agctgattta acaaaaattt aacgcgaatt ttaacaaaat attaacgttt acaattttat   2940
ggtgcactct cagtacaatc tgctctgatg ccgcatagtt aagccagccc cgacacccgc   3000
caacacccgc tgacgcgccc tgacgggctt gtctgctccg gcatccgctt acagacaagc   3060
tgtgaccgtc tccgggagct gcatgtgtca gaggttttca ccgtcatcac cgaaacgcgc   3120
gagacgaaag ggcctcgtga tacgcctatt tttataggtt aatgtcatga taataatggt   3180
ttcttagacg tcaggtggca cttttcgggg aaatgtgcgc ggaaccccta tttgtttatt   3240
tttctaaata cattcaaata tgtatccgct catgagacaa taaccctgat aaatgcttca   3300
ataatattga aaaggaaga gtatgagtat tcaacatttc cgtgtcgccc ttattccctt    3360
ttttgcggca ttttgccttc ctgttttttgc tcacccagaa acgctggtga agtaaaaga   3420 tgctgaagat cagttgggtg cacgagtggg ttacatcgaa ctggatctca acagcggtaa   3480
gatccttgag agttttcgcc ccgaagaacg ttttccaatg atgagcactt ttaaagttct   3540
gctatgtggc gcggtattat cccgtattga cgccgggcaa gagcaactcg gtcgccgcat   3600
acactattct cagaatgact tggttgagta ctcaccagtc acagaaaagc atcttacgga   3660
tggcatgaca gtaagagaat tatgcagtgc tgccataacc atgagtgata cactgcggc    3720 caacttactt ctgacaacga tcggaggacc gaaggagcta accgcttttt tgcacaacat   3780
gggggatcat gtaactcgcc ttgatcgttg ggaaccggag ctgaatgaag ccataccaaa   3840
cgacgagcgt gacaccacga tgcctgtagc aatggcaaca acgttgcgca aactattaac   3900
tggcgaacta cttactctag cttcccggca acaattaata gactggatgg aggcggataa   3960
agttgcagga ccacttctgc gctcggccct tccggctggc tggtttattg ctgataaatc   4020
tggagccggt gagcgtgggt ctcgcggtat cattgcagca ctggggccag atggtaagcc   4080
ctcccgtatc gtagttatct acacgacggg gagtcaggca actatggatg aacgaaatag   4140
acagatcgct gagataggtg cctcactgat taagcattgg taactgtcag accaagttta   4200
ctcatatata ctttagattg atttaaaact catttttaa tttaaaagga tctaggtgaa    4260 gatcctttt gataatctca tgaccaaaat cccttaacgt gagttttcgt tccactgagc    4320
```

```
gtcagacccc gtagaaaaga tcaaaggatc ttcttgagat cctttttttc tgcgcgtaat    4380
ctgctgcttg caaacaaaaa aaccaccgct accagcggtg gtttgtttgc cggatcaaga    4440
gctaccaact cttttttccga aggtaactgg cttcagcaga gcgcagatac caaatactgt    4500
tcttctagtg tagccgtagt taggccacca cttcaagaac tctgtagcac cgcctacata    4560
cctcgctctg ctaatcctgt taccagtggc tgctgccagt ggcgataagt cgtgtcttac    4620 cggggttggac tcaagacgat agttaccgga taaggcgcag cggtcgggct gaacgggggg    4680
ttcgtgcaca cagcccagct tggagcgaac gacctacacc gaactgagat acctacagcg    4740
tgagctatga gaaagcgcca cgccttcccg aagggagaaa ggcggacagg tatccggtaa    4800
gcggcagggt cggaacagga gagcgcacga gggagcttcc aggggaaac gcctggtatc     4860 tttatagtcc tgtcgggttt cgccacctct gacttgagcg tcgattttg tgatgctcgt     4920 caggggggcg gagcctatgg aaaaacgcca gcaacgcggc cttttacgg ttcctggcct     4980 tttgctggcc ttttgctcac atgttctttc ctgcgttatc ccctgattct gtggataacc    5040
gtattaccgc ctttgagtga gctgataccg ctcgccgcag ccgaacgacc gagcgcagcg    5100
agtcagtgag cgaggaagcg gaagagcgcc caatacgcaa accgcctctc cccgcgcgtt    5160
ggccgattca ttaatccaac tggcacgaca ggtttcccga ctggaaagcg ggcagtgagc    5220
gcaacgcaat taatgtgagt tagctcactc attaggcacc ccaggcttta cactttatgc    5280
ttccggctcg tatgttgtgt ggaattgtga gcggataaca atttcacaca ggaaacagct    5340
atgacatgat ta                                                        5352
```

<210> SEQ ID NO 73
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: CDR3 sequence encoded by human antibody clone

<400> SEQUENCE: 73

Ala Gly Thr Val Tyr Tyr Asp Ile Leu Thr Gly Leu Tyr Thr Asn Phe
1               5                   10                  15

His Tyr

<210> SEQ ID NO 74
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: CDR3 sequence encoded by human antibody clone

<400> SEQUENCE: 74

Ala Arg Asp Ser Gly Leu Asp Tyr Phe Asp Ser Ala Gly Tyr Asn Glu
1               5                   10                  15

Pro Phe Asp Val
            20

<210> SEQ ID NO 75
<211> LENGTH: 14
<212> TYPE: PRT
<213> ORGANISM: Homo sapiens
<220> FEATURE:
<221> NAME/KEY: misc_feature
<222> LOCATION: (1)..(14)

```
<223> OTHER INFORMATION: CDR3 sequence encoded by human antibody clone

<400> SEQUENCE: 75

Ala Arg Val His Gly Asn Ser Gly Leu Asn Trp Phe Asp Pro
1               5                   10

<210> SEQ ID NO 76
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CDR3 sequence encoded by human antibody clone

<400> SEQUENCE: 76

Ala Thr Glu Gly Asp Asp Asn Thr Tyr Tyr Tyr Asp Ser Ser Gly Tyr
1               5                   10                  15

Tyr Tyr Tyr Gly Met Asp Val
            20

<210> SEQ ID NO 77
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: CDR3 sequence encoded by human antibody clone

<400> SEQUENCE: 77

Ala Ser Gly Ile Arg Gly Ala Asp Tyr Gly Asp Val Gly His Tyr
1               5                   10                  15

Tyr Tyr Gly Val Asp Val
            20

<210> SEQ ID NO 78
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: CDR3 sequence encoded by human antibody clone

<400> SEQUENCE: 78

Ala Lys Asp Leu Arg Leu Gly Gly Gly Ser Asp Tyr
1               5                   10

<210> SEQ ID NO 79
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: CDR3 sequence encoded by human antibody clone

<400> SEQUENCE: 79

Ala Arg Ala Glu Leu Glu Pro Asn Asp Tyr Gly Asp Ser Pro His Val
1               5                   10                  15

Arg Trp Tyr Phe Asp Leu
            20

<210> SEQ ID NO 80
<211> LENGTH: 23
```

```
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CDR3 sequence encoded by human antibody clone

<400> SEQUENCE: 80

Ala Ser Ala Glu Glu Asn Asp Tyr Gly Glu Ser Gly Pro Pro Tyr
1               5                   10                  15

Phe Tyr Tyr Tyr Met Asp Val
            20

<210> SEQ ID NO 81
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: CDR3 sequence encoded by human antibody clone

<400> SEQUENCE: 81

Ala Gly Thr Gly Pro Pro Asn Asp Tyr Gly Asp Asp Val Val His Glu
1               5                   10                  15

Gly Tyr Tyr Tyr Asn Tyr Leu Asp Val
            20                  25

<210> SEQ ID NO 82
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: CDR3 sequence encoded by human antibody clone

<400> SEQUENCE: 82

Ala Lys Glu Ala Asp Trp Asp Tyr Tyr Asp Thr Ser Val Tyr Pro Phe
1               5                   10                  15

Ala Tyr

<210> SEQ ID NO 83
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: CDR3 sequence encoded by human antibody clone

<400> SEQUENCE: 83

Ala Arg Asp His Pro Asp Ser Glu Gly Gly Gly Tyr
1               5                   10

<210> SEQ ID NO 84
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: CDR3 sequence encoded by human antibody clone

<400> SEQUENCE: 84

Ala Arg Ile Ala Val Ala Gly Val Gly Ala Phe Asp Ile
1               5                   10
```

```
<210> SEQ ID NO 85
<211> LENGTH: 27
<212> TYPE: PRT
<213> ORGANISM: Homo sapiens
<220> FEATURE:
<221> NAME/KEY: misc_feature
<222> LOCATION: (1)..(27)
<223> OTHER INFORMATION: CDR3 sequence encoded by human antibody clone

<400> SEQUENCE: 85

Ala Thr Val Ile Phe Gly Gly Pro Asp Tyr Tyr His Ser Gly Asp Val
1               5                   10                  15

Gly Glu Thr Gly Ala Val Tyr Tyr Phe Asp Asn
            20                  25

<210> SEQ ID NO 86
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 86

Ala Ser Gly Thr Glu Pro Asp Tyr Ala Asp Ser Ser Gly Tyr Tyr Trp
1               5                   10                  15

Phe Asp Cys

<210> SEQ ID NO 87
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CDR3 sequence encoded by human antibody clone

<400> SEQUENCE: 87

Ala Thr Asp Gly Ala Arg Asp Thr Asp Tyr Tyr Asp Ser Ser Gly Tyr
1               5                   10                  15

Leu Leu Phe Ile Ala Phe Asp Ile
            20

<210> SEQ ID NO 88
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: CDR3 sequence encoded by human antibody clone

<400> SEQUENCE: 88

Ala Gly Thr Gly Pro Pro Asn Asp Tyr Gly Asp Val Val His Glu
1               5                   10                  15

Gly Tyr Tyr Tyr Asn Tyr Leu Asp Val
            20                  25

<210> SEQ ID NO 89
<211> LENGTH: 19
<212> TYPE: PRT
<213> ORGANISM: Homo sapiens
<220> FEATURE:
<221> NAME/KEY: misc_feature
```

```
<222> LOCATION: (1)..(19)
<223> OTHER INFORMATION: CDR3 sequence encoded by human antibody clone

<400> SEQUENCE: 89

Ala Ser Trp Ala Gly Tyr Tyr Asp Ser Ser Tyr Pro Leu Ser Ala
1               5                   10                  15

Phe Asp Ile

<210> SEQ ID NO 90
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: CDR3 sequence encoded by human antibody clone

<400> SEQUENCE: 90

Ala Ser Asp Ser Arg Asp Phe Ser Tyr Tyr Glu Pro Gly Thr Ser Tyr
1               5                   10                  15

Ser His Tyr Tyr Asn Ile Met Asp Val
            20                  25

<210> SEQ ID NO 91
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 91

Ala Ser Arg Gln His His Glu Tyr Phe Gln Glu
1               5                   10

<210> SEQ ID NO 92
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CDR3 sequence encoded by human antibody clone

<400> SEQUENCE: 92

Ala Arg Ala Pro Leu Gly Arg Asn Ser Tyr Gly Pro Asp Gly Thr Gly
1               5                   10                  15

Asp Ala Phe Asp Met
            20

<210> SEQ ID NO 93
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 93

Ala Ser Trp Ala Gly Tyr Tyr Asp Ser Pro Ser Tyr Pro Leu Ser Ala
1               5                   10                  15

Phe Asp Val
```

```
<210> SEQ ID NO 94
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: CDR3 sequence encoded by human antibody clone

<400> SEQUENCE: 94

Ala Ser Gly Gly Asp Ser Asp Tyr Tyr Glu Ile Gly Arg Thr Tyr His
1               5                   10                  15

Tyr Tyr Tyr Ala Met Asp Val
            20

<210> SEQ ID NO 95
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: CDR3 sequence encoded by human antibody clone

<400> SEQUENCE: 95

Val Arg Arg Asn Leu Ser Gly Asp Arg Gly Gly Trp Phe Asp Pro
1               5                   10                  15

<210> SEQ ID NO 96
<211> LENGTH: 27
<212> TYPE: PRT
<213> ORGANISM: Homo sapiens
<220> FEATURE:
<221> NAME/KEY: misc_feature
<222> LOCATION: (1)..(27)
<223> OTHER INFORMATION: CDR3 sequence encoded by human antibody clone

<400> SEQUENCE: 96

Ala Gly Ser Pro Glu Gly Pro Asn Asp Tyr Val Trp Gly Thr Tyr Arg
1               5                   10                  15

Pro Gly Ala Phe Leu Tyr Tyr Gly Leu Asp Val
            20                  25

<210> SEQ ID NO 97
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: CDR3 sequence encoded by human antibody clone

<400> SEQUENCE: 97

Ala Ala Ile Asp Tyr Gly Asp Phe Ala Tyr Tyr Tyr Gly Met Asp Val
1               5                   10                  15

<210> SEQ ID NO 98
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: CDR3 sequence encoded by human antibody clone

<400> SEQUENCE: 98

Ala Ser Asp His Gly Ala Asp Asp Tyr Asp Ser Gly Ala Phe Leu Ser
1               5                   10                  15
```

Ala Phe Gly Phe
            20

<210> SEQ ID NO 99
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: CDR3 sequence encoded by human antibody clone

<400> SEQUENCE: 99

Ala Arg Asp Leu Glu Met Arg Asp Gly Asn Asn His Gly Ser His Leu
1               5                   10                  15

Glu Phe

<210> SEQ ID NO 100
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: CDR3 sequence encoded by human antibody clone

<400> SEQUENCE: 100

Ala Ser Asp His Gly Ala Asp Asp Tyr Asp Ser Gly Ala Phe Leu Ser
1               5                   10                  15

Ala Phe Gly Phe
            20

<210> SEQ ID NO 101
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 101

Ala Ser Trp Ala Gly Tyr Tyr Asp Ser Pro Ser Tyr Pro Leu Ser Ala
1               5                   10                  15

Phe Asp Val

<210> SEQ ID NO 102
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: CDR3 sequence encoded by human antibody clone

<400> SEQUENCE: 102

Ala Lys Asp Leu Ser Val Gly Gln Trp Pro Pro Ile Asn Ala Phe Asp
1               5                   10                  15

Val

<210> SEQ ID NO 103
<211> LENGTH: 11
<212> TYPE: PRT
<213> ORGANISM: Homo sapiens
<220> FEATURE:

```
<221> NAME/KEY: misc_feature
<222> LOCATION: (1)..(11)
<223> OTHER INFORMATION: CDR3 sequence encoded by human antibody clone

<400> SEQUENCE: 103

Val Arg Asp Arg Ser Asn Leu Ala Phe Glu Tyr
1               5                   10

<210> SEQ ID NO 104
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: CDR3 sequence encoded by human antibody clone

<400> SEQUENCE: 104

Ala Thr Ser Val Thr Tyr Glu Thr Asn Ala Tyr Tyr Cys Phe Asp Ser
1               5                   10                  15

<210> SEQ ID NO 105
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: CDR3 sequence encoded by human antibody clone

<400> SEQUENCE: 105

Ala Arg Ser Ser Gly Ser Tyr Tyr His Asn Phe Asp Tyr
1               5                   10

<210> SEQ ID NO 106
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: CDR3 sequence encoded by human antibody clone

<400> SEQUENCE: 106

Ala Arg Asn Pro Asn Asp Arg Phe Pro Phe Thr Val Val Arg Gly Val
1               5                   10                  15

Ser Phe Asp Tyr
            20

<210> SEQ ID NO 107
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CDR3 sequence encoded by human antibody clone

<400> SEQUENCE: 107

Ala Arg His Asp Ala Glu Tyr Asp Phe Trp Gly Ser Gly Arg Leu Arg
1               5                   10                  15

Gly Trp Phe Gly Pro
            20

<210> SEQ ID NO 108
<211> LENGTH: 22
<212> TYPE: PRT
```

```
<213> ORGANISM: Homo sapiens
<220> FEATURE:
<221> NAME/KEY: misc_feature
<222> LOCATION: (1)..(22)
<223> OTHER INFORMATION: CDR3 sequence encoded by human antibody clone

<400> SEQUENCE: 108

Ala Lys His Asp Ala Gln Tyr Asp Phe Val Trp Asn Ser Gly Arg Val
1               5                   10                  15

Arg Gly Trp Phe Asp Pro
            20

<210> SEQ ID NO 109
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 109

Ala Arg Thr Phe Thr Tyr Tyr Phe Asp Glu Val Asp Trp Ala Gln Ser
1               5                   10                  15

Phe Asp Ile

<210> SEQ ID NO 110
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 110

Ala Arg Thr Phe Thr Tyr Tyr Phe Asp Asp Val Asp Trp Ala Gln Ser
1               5                   10                  15

Phe Asp Val

<210> SEQ ID NO 111
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: CDR3 sequence encoded by human antibody clone

<400> SEQUENCE: 111

Ala Arg Arg Ser Tyr Asp Tyr Gly Asp Asp Val Asp Leu Val Thr
1               5                   10                  15

Asp Tyr Tyr Tyr Tyr Met Asp Val
            20

<210> SEQ ID NO 112
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: CDR3 sequence encoded by human antibody clone

<400> SEQUENCE: 112

Ala Arg Phe Asp Ala Gly Tyr Ser Glu Thr Thr Asp Ser Asn Ala Leu
```

```
1               5                   10                  15

Asp Val

<210> SEQ ID NO 113
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: CDR3 sequence encoded by human antibody clone

<400> SEQUENCE: 113

Ala Thr Gly Arg Met Gly Tyr Tyr Asp Ser Ser Gly Tyr His Tyr Val
1               5                   10                  15

Gly Leu Phe Gln Met
            20

<210> SEQ ID NO 114
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 114

Val Arg Asp Gly Asp Asp Gly Asp Tyr
1               5

<210> SEQ ID NO 115
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: CDR3 sequence encoded by human antibody clone

<400> SEQUENCE: 115

Ala Arg Glu Trp Asn Arg Asp Ser Asp Trp Ser Pro Tyr Tyr His Ala
1               5                   10                  15

Phe Asp Val

<210> SEQ ID NO 116
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 116

Gln Ala Trp Ala Ser Thr Thr Val Ile
1               5

<210> SEQ ID NO 117
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone
```

```
<400> SEQUENCE: 117

Gln Gln Tyr Ala Asn Ser Pro Ile Thr
1               5

<210> SEQ ID NO 118
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 118

Gln Ala Ala Asp Ser Thr Gly Ile Tyr Pro Thr
1               5                   10

<210> SEQ ID NO 119
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 119

Gln Gln Tyr Lys Ser Phe Pro Tyr Thr
1               5

<210> SEQ ID NO 120
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 120

Ser Ser Tyr Ala Gly Ser Thr Thr Phe Arg Val
1               5                   10

<210> SEQ ID NO 121
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 121

Leu His His Ser Asn Trp Pro Pro Ser Leu Thr
1               5                   10

<210> SEQ ID NO 122
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 122

Gln Gln Tyr Asn Ser Leu Pro Leu Thr
1               5
```

```
<210> SEQ ID NO 123
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 123

Gln Gln Tyr Asn Ser Tyr Pro Tyr Ser
1               5

<210> SEQ ID NO 124
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 124

Gln Gln Tyr Gly Ser Thr Pro Leu Thr
1               5

<210> SEQ ID NO 125
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 125

Gln Gln Tyr Asn Thr Tyr Pro Tyr Thr
1               5

<210> SEQ ID NO 126
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 126

Ala Ala Trp Asp Asp Ser Leu Asn Gly Trp Val
1               5                   10

<210> SEQ ID NO 127
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 127

Gln Gln Tyr Tyr Ser Ser Pro Leu Thr
1               5

<210> SEQ ID NO 128
<211> LENGTH: 9
```

```
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 128

Gln Gln Tyr Asn Asn Trp Pro Tyr Thr
1               5

<210> SEQ ID NO 129
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 129

Gln Gln Tyr Ser Ser Ser Pro Ile Thr
1               5

<210> SEQ ID NO 130
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 130

Gln Gln Tyr Gly Gly Ser Val Ser Ser
1               5

<210> SEQ ID NO 131
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 131

Gln Gln Tyr Ser Ser Asp Trp Val Thr
1               5

<210> SEQ ID NO 132
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 132

Gln Gln Tyr Gly Ser Ser Pro Glu Thr
1               5

<210> SEQ ID NO 133
<211> LENGTH: 9
<212> TYPE: PRT
<213> ORGANISM: Homo sapiens
<220> FEATURE:
<221> NAME/KEY: misc_feature
```

```
<222> LOCATION: (1)..(9)
<223> OTHER INFORMATION: CDR3 sequence encoded by human antibody clone

<400> SEQUENCE: 133

Gln Gln Tyr Gly Thr Ser Pro Leu Thr
1               5

<210> SEQ ID NO 134
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 134

Gln Gln Tyr Asn Ser Tyr Ser Ser Ser
1               5

<210> SEQ ID NO 135
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 135

Gln Gln Tyr Asn Ser Tyr Pro Tyr Ser
1               5

<210> SEQ ID NO 136
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 136

Gln Gln Tyr Ser Ser Asp Trp Val Thr
1               5

<210> SEQ ID NO 137
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: CDR3 sequence encoded by human antibody clone

<400> SEQUENCE: 137

Gln Gln Tyr Asn Thr Trp Thr
1               5

<210> SEQ ID NO 138
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 138
```

```
Gln Gln Tyr Asn Ser Tyr Ser Ser Ser
1               5

<210> SEQ ID NO 139
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 139

Met Gln Ser Ile Gln Pro Pro Leu Thr
1               5

<210> SEQ ID NO 140
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 140

Gln Gln Tyr Asp Thr Leu Pro Pro Thr
1               5

<210> SEQ ID NO 141
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 141

Gln Gln Tyr Asn Ser Tyr Ser Trp Thr
1               5

<210> SEQ ID NO 142
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 142

Gln Gln Tyr Ser Thr Tyr Pro Leu Thr
1               5

<210> SEQ ID NO 143
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 143

Gln Gln Tyr Ser Ser Asp Trp Val Thr
1               5
```

```
<210> SEQ ID NO 144
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 144

Gln Gln Leu Asn Thr Tyr Pro Leu Thr
1               5

<210> SEQ ID NO 145
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: CDR3 sequence encoded by human antibody clone

<400> SEQUENCE: 145

Met Gln Ala Lys Glu Ser Pro Thr
1               5

<210> SEQ ID NO 146
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: CDR3 sequence encoded by human antibody clone

<400> SEQUENCE: 146

Gln Ser Tyr Asp Tyr Arg Leu Ser Gly Ser Gly Val
1               5                   10

<210> SEQ ID NO 147
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 147

Gln His Tyr Asn Ser Tyr Ser Ile Thr
1               5

<210> SEQ ID NO 148
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 148

Gln Gln Tyr Asn Thr Tyr Ser Gln Thr
1               5

<210> SEQ ID NO 149
<211> LENGTH: 9
<212> TYPE: PRT
```

```
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 149

Gln Gln Tyr Asn Ser Leu Pro Tyr Ser
1               5

<210> SEQ ID NO 150
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: CDR3 sequence encoded by human antibody clone

<400> SEQUENCE: 150

Gln Tyr Tyr Gly Arg Ser Pro Pro Tyr Thr
1               5                   10

<210> SEQ ID NO 151
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 151

Gln Gln Leu Asn Ser Tyr Pro Pro Thr
1               5

<210> SEQ ID NO 152
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: CDR3 sequence encoded by human antibody clone

<400> SEQUENCE: 152

Gln Gln Arg Thr Asn Trp Pro Pro Tyr Met Tyr Thr
1               5                   10

<210> SEQ ID NO 153
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 153

Gln Gln Ser Tyr Thr Thr Pro Pro Thr
1               5

<210> SEQ ID NO 154
<211> LENGTH: 9
<212> TYPE: PRT
<213> ORGANISM: Homo sapiens
<220> FEATURE:
<221> NAME/KEY: misc_feature
<222> LOCATION: (1)..(9)
```

```
<223> OTHER INFORMATION: CDR3 sequence encoded by human antibody clone

<400> SEQUENCE: 154

Gln Gln Tyr Tyr Val Tyr Pro Phe Thr
1               5

<210> SEQ ID NO 155
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 155

Gln Gln Tyr Ala His Ser Pro Leu Thr
1               5

<210> SEQ ID NO 156
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 156

Gln Gln Tyr Gly Ser Ser Pro Leu Thr
1               5

<210> SEQ ID NO 157
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: CDR3 sequence encoded by human antibody clone

<400> SEQUENCE: 157

Gln Gln Tyr Gly Ser Ser Leu Pro Leu Thr
1               5                   10

<210> SEQ ID NO 158
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: CDR3 sequence encoded by human antibody clone

<400> SEQUENCE: 158

Gln Leu Tyr Asp Ser Ser Pro Leu Phe Thr
1               5                   10

<210> SEQ ID NO 159
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: CDR3 sequence encoded by human antibody clone

<400> SEQUENCE: 159
```

```
Gln His Tyr Asn Asn Trp Pro Pro Trp Thr
1               5                   10
```

<210> SEQ ID NO 160
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: CDR3 sequence encoded by human antibody clone

<400> SEQUENCE: 160

```
Ala Thr Trp Asp Asp Thr Leu Ser Gly Pro Leu
1               5                   10
```

<210> SEQ ID NO 161
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 161

```
Gln Gln Tyr Asp Thr Tyr Pro Trp Thr
1               5
```

<210> SEQ ID NO 162
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: CDR3 sequence encoded by human antibody clone

<400> SEQUENCE: 162

```
Asn Ser Tyr Thr Thr Ser Asn Thr Leu Val
1               5                   10
```

<210> SEQ ID NO 163
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: CDR3 sequence encoded by human antibody clone

<400> SEQUENCE: 163

```
Gln Gln Tyr Tyr Ser Thr Pro Tyr Thr
1               5
```

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 164

```
gtccaactgc acctcggttc                                              20
```

RAPID EXPRESSION CLONING OF HUMAN MONOCLONAL ANTIBODIES FROM MEMORY B CELLS

CROSS-REFERENCE TO RELATED APPLICATIONS

This application claims priority to U.S. Provisional Application No. 61/114,047, filed Nov. 12, 2008, which is herein incorporated by reference in its entirety.

FIELD

The present application generally relates to methods for producing human monoclonal antibodies without using hybridoma technology and methods for using the antibodies to treat or prevent disease conditions (e.g., infection by pathogens such as the Human Immunodeficiency Virus).

BACKGROUND

Although an HIV-1 vaccine continues to be elusive after over twenty years of effort, it remains the single best hope to stop the epidemic (1, 2). The recent failure of an Ad5-vectored 'CTL' vaccine and the earlier failure of a gp120 subunit vaccine are sobering testaments to the difficulty of this task (2). Because of these failures, there is renewed focus on the identification and characterization of protective humoral responses in groups of HIV-1 infected individuals who spontaneously control their infections. These groups include long-term non-progressors (LTNP) who maintain stable CD4 counts without disease over many years (3) and elite controllers (EC) (4) or, in our clinic, natural viral suppressors (NVS) (5), who control viral replication to undetectable levels without antiretroviral therapy. Several recent studies have attempted to characterize the anti-envelope antibodies (Abs) found in the plasma or sera of rare HIV-infected humans that exhibit broadly neutralizing activity (6, 7). However, the specificities of circulating Abs are likely to change and/or decline significantly over time given the high mutability of the HIV envelope (8), particularly under conditions where antigenemia is limiting. Thus, circulating Ab specificities in chronically HIV-1-infected persons are unlikely to represent the full spectrum of Abs elicited by the virus from the time of early acute infection. Further, potentially important Ab responses that occur during the critical period of acute infection might not be detected by serological analyses of samples taken after viral loads have declined to setpoint. For example, it is known that EC have lower titers of HIV-1 specific Abs than chronic progressors (9, 10). Therefore there is a need for a new approach to evaluate the present and past immune responses in HIV-infected individuals to identify new and therapeutically useful antibodies. This same issue is important in individuals that have been infected with other pathogens or who have autoimmune diseases.

Once such antibodies are identified, there is a need for a reliable method for making them, preferably as fully human antibodies for human use. Five general methods are used to isolate human monoclonal antibodies (mAbs). Each method suffers from technical limitations that render it difficult to use in comparison with the original Kohler-Milstein hybridoma method used to isolate murine mAbs. These methods include hybridomas (40), B cell transformation with Epstein-Barr virus (EBV) (41), phage display (42), yeast display (43), and 'humanization' of murine mAbs (44). Due to the lack of a generic cell fusion partner, it has proven difficult to reproducibly isolate human mAbs by conventional hybridoma methods, although this method has proven successful (c.f, for an interesting recent example (45)). EBV transformation has proven equally difficult but for different reasons. EBV transformed B cell lines are often genetically unstable and the consequent high rate of clone loss makes this method very cumbersome.

Recently, a modified EBV method was described that uses EBV to transform enriched memory B cells ($B_{Mem}$) from immunized $B_{Mem}$ (26). This method works well for many immunogens but it requires normal $B_{Mem}$, which are often lacking during chronic infections such as HIV-1 (18). Phage and yeast display overcome these problems but these methods rely on either Fab fragments or single-chain Fv (scFv) fragments in the screening obviating the uses of these methods for screening by functional analyses such as viral neutralization. Phage display also suffers from the problem that it imposes unidentified structural restrictions on antibody specificities that can be stably expressed as recombinant phage (46). Finally, it is possible to 'humanize' murine mAbs by grafting the gene segments that encode antigen binding onto human variable region genes. This is a highly labor intensive endeavor and beyond the reach of most research laboratories. Therefore there is a need for a new method to rapidly clone full-length human mAbs that obviates these problems.

SUMMARY

Provided herein are methods that can be used to rapidly clone full-length human monoclonal antibodies that can be used to treat diseases and conditions, such as infections by pathogens, cancer, and autoimmune disease.

In a first aspect, provided herein is a method for producing a monoclonal antibody that specifically binds to a particular known antigen. The method includes the steps of: (a) obtaining a blood sample from an animal that has been exposed to the particular known antigen; (b) isolating a plurality of memory B cells from the blood sample; (c) culturing the plurality of the isolated memory B cells under conditions and for a sufficient time to permit the memory B cells to differentiate into plasma cells that stably produce monoclonal antibodies; (d) determining whether the plasma cells produce the monoclonal antibody that specifically binds to the particular known antigen; (e) if the plasma cells produce the monoclonal antibody that specifically binds to the particular known antigen, then isolating total RNA from the plasma cells, and if the plasma cells do not produce the monoclonal antibody, then repeating steps (b) through (d) until a plurality of isolated memory B cells is identified that differentiates into plasma cells that stably produce the monoclonal antibody; (f) using the isolated total RNA of step (e) to produce cDNA encoding variable-heavy (VH) antibody chains and cDNA encoding variable-light (VL) antibody chains encoded by mRNA molecules within the total RNA; (g) cloning VH chain cDNA into a eukaryotic expression vector and cloning VL chain cDNA into a eukaryotic expression vector, (h) selecting expression vectors comprising VH chain cDNA to produce a VH chain mini-library and selecting expression vectors comprising VL chain cDNA to make a VL chain mini-library; (i) co-transfecting an appropriate host cell with a mixture comprising VH chain cDNA expression vectors from the VH chain mini-library and with a mixture comprising VL chain cDNA expression vectors from the VL chain mini-library, and growing the co-transfected cells under conditions and for a sufficient time to permit the cells to stably produce antibodies; (j) determining that the co-transfected cells produce the monoclonal antibody that specifically binds to the particular known antigen; (k) identifying the VH chain cDNA that encodes the VH chain of the monoclonal antibody of step (j), comprising the steps of: (i) co-transfecting an appropriate host cell with a particular VH chain cDNA expression vector obtained from the VH chain cDNA mini-library and with a mixture comprising VL chain cDNA expression vectors from the VL chain mini-library, and growing co-transfected cells under conditions and for a sufficient time to permit the co-transfected cells to form a clone that stably produces an antibody; (ii) determining whether the clone produces the monoclonal antibody that specifically binds to the particular known antigen; (iii) if the co-transfected cells produce the monoclonal antibody that specifically binds to the particular known antigen, then proceeding to step (k)(iv), and if the co-transfected cells do not produce the monoclonal antibody, then repeating steps (k)(i) and (k)(ii) using a different particular VH chain cDNA expression vector until a particular VH chain cDNA expression vector is identified that produces the monoclonal antibody; (iv) identifying the VH chain cDNA that produced the monoclonal antibody, and selecting the VH chain cDNA expression vector that was used to make the clone that produces the monoclonal antibody that specifically binds to the particular known antigen; (l) identifying the VL chain cDNA that encodes the VL chain of the monoclonal antibody of step (k), comprising the steps of: (i) co-transfecting an appropriate host cell with the VH chain cDNA expression vector identified in step (k)(iv) and with a particular VL chain cDNA expression vector selected from the VL chain mini-library, and growing co-transfected cells under conditions and for a sufficient time to permit the co-transfected cells to form a clone that stably produces an antibody; (ii) determining whether the clone produces the monoclonal antibody that specifically binds to the particular known antigen; (iii) if the clone produces the monoclonal antibody that specifically binds to the particular known antigen then proceeding to step (l)(iv), and if the co-transfected cells do not produce the monoclonal antibody, then repeating steps (l)(i) and (l)(ii) with a different particular VL chain cDNA expression vector until a particular VL chain cDNA expression vector is identified that produces the monoclonal antibody; (iv) identifying the VL chain cDNA that encodes the VL chain of the monoclonal antibody, and selecting the VL chain cDNA expression vector that was used to make the clone that produces the monoclonal antibody; and (m) co-transfecting an appropriate host cell with the identified VH chain cDNA expression vector of step (k)(iv) and the identified VL chain cDNA expression vector of step (l)(iv) to produce a host cell that produces the monoclonal antibody that specifically bind to the particular known antigen, thereby producing a monoclonal antibody that binds to a particular known antigen.

In the above-described method, the VL chain can be a Vκ chain or a Vλ chain.

The host cells can be, e.g., bacterial cells, 273 T cells, or Chinese hamster ovary cells and the eukaryotic expression vector can be, e.g., an IgG1, kappa, or gamma eukaryotic expression vector.

In the above-described method, the VH chain and VL chain cDNAs can be cloned into the same expression vector.

The particular known antigen can be an antigen from a pathogen, e.g., a virus, a bacterium, a prion, a fungus, a yeast, or a parasite. For example, the pathogen can be human immunodeficiency virus (HIV), e.g., HIV-1 or HIV-2.

In the above-described method, the isolated memory B cells can be cultured, e.g., at a density of approximately 100 memory B cells per well.

The animal from which the B memory cells are obtained can be previously exposed to the pathogen by immunization with a vaccine against the pathogen, or the animal can be previously naturally infected with the pathogen. In certain instances, the animal will have been infected with a human immunodeficiency virus and the animal will be able to spontaneously control viremia.

The animal from which the B memory cells are obtained can have an autoimmune disease that makes antibodies against a self antigen, which disease is a member selected from the group comprising systemic lupus erythematosus (SLE), diabetes mellitus type 1, Crohn's disease, multiple sclerosis, myasthenia gravis. These auto-antibodies can be used as targets for treatment of the autoimmune disease.

The animal from which the B memory cells are obtained can have a tumor or cancer at the time the B memory cells are obtained or prior to the time the B memory cells are obtained. The B memory cells, when allowed to mature into antibody-producing plasma cells, can produce antibodies that specifically bind the tumor or cancer cells.

The antigen can be a member of the group including carbohydrates, lipids, proteins, peptides, nucleic acids, and small molecules (organic and inorganic).

The animal can be a human, in which case the monoclonal antibodies are fully human monoclonal antibodies.

In a second aspect, provided herein is monoclonal antibody isolated by the method described above. The monoclonal antibody can have a third complementarity-determining region of a variable heavy chain (VH) that comprises an amino acid sequence of at least one of SEQ ID NO: 73 through SEQ ID NO: 115. The monoclonal antibody can have a third complementarity-determining region of a variable light chain (VL) that comprises an amino acid sequence of at least one of SEQ ID NO: 116 through SEQ ID NO: 163.

In a third aspect, provided herein is a method for treating or preventing infection by human immunodeficiency virus in a subject, including administering to the subject a monoclonal antibody isolated by the method described above.

In a fourth aspect, provided herein is a method for identifying a monoclonal antibody for therapeutic use in treating or preventing a disease caused by an infection with human immunodeficiency virus (HIV). The method includes: (a) obtaining a blood sample from an animal that is an elite controller or a natural virus suppressor of HIV; (b) determining if the blood sample contains any antibodies that bind to the particular known pathogen; (c) isolating memory B cells from the blood sample; (d) culturing the plurality of the isolated memory B cells under conditions and for a sufficient time to permit the memory B cells to differentiate into plasma cells that stably produce monoclonal antibodies; (e) determining if the plasma cells produce monoclonal antibodies that specifically bind to HIV; (f) comparing the monoclonal antibodies made by the plasma cells to the antibodies in the blood sample; and (g) if the monoclonal antibodies made by the plasma cells are different from the antibodies in the blood sample, then identifying and selecting the different monoclonal antibodies made by the plasma cells.

The plasma cells of step (g) above can be selected to produce a transformed host cell clone that stably produces the different monoclonal antibodies using steps (e)-(m) of the method described in the first aspect above.

In a fifth aspect, provided herein is a method for determining whether an animal has been exposed to a particular known antigen when the animal is not currently producing antibodies that specifically bind to the particular known antigen. The method includes: (a) obtaining a blood sample from the animal; (b) isolating memory B cells from the blood sample; (c) culturing isolated memory B cells under conditions and for a sufficient time to permit the memory B cells to differentiate into plasma cells that stably produce monoclonal antibodies;

and (d) determining whether the plasma cells produce a monoclonal antibody that specifically binds to the particular known antigen, whereby production of the monoclonal antibody indicates that the animal has been exposed to the particular known antigen and whereby non-production of the monoclonal antibody indicates that the animal might not have been exposed to the particular known antigen.

The antigen can be an antigen from a pathogen, such as human immunodeficiency virus (HIV).

BRIEF DESCRIPTION OF THE DRAWINGS

The present invention is illustrated by way of example, and not by way of limitation, in the figures of the accompanying drawings and in which:

FIG. 5. Identification of CD4i and CD4bs mAbs by ELISA. Representative CD4i and CD4bs mAbs were tested in three formats of HIV-1 Env ELISAs as described in the Examples. A) Right, middle and left charts show results for CD4i mAbs (17b,ED47,A32), CD4bs mAbs (b12,M14,sCD4-Ig), and mAb 2G12, respectively. ELISA curves for reactivity to FLSC (filled symbol) and to gp120$_{Ba-L}$ (open symbol) are shown. B) OD values of ELISAs for all these representative mAbs at 0.1 ug/ml are shown. CD4i mAbs are identified by their strong binding to FLSC and weak binding to gp120$_{Ba-L}$ or gp140$_{Ba-L}$, while CD4bs mAbs are identified by comparison of their strong binding to gp120$_{Ba-L}$ or gp140$_{Ba-L}$, and their weak biding to FLSC. MAbs other than CD4i and CD4bs are denoted as the 'Other' category. One of the 'Other' mAb, 2G12, binds equally well to FLSC and gp120$_{Ba-L}$, and therefore, is used to standardize the ELISAs.

DETAILED DESCRIPTION

Figure 1A:
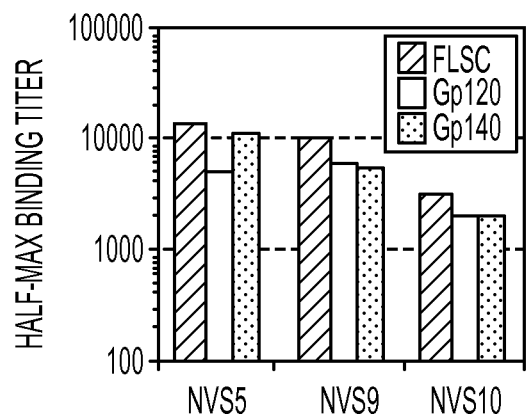
FIG. 1. Characterization of plasma Abs to HIV-1 Env protein. A) Plasma Abs against FLSC, gp120$_{Ba-L}$, and gp140$_{Ba-L}$ were detected by ELISA and half-max binding titers are shown on a log scale. B) CD4i Abs in plasma of NVS donors were detected by enhanced neutralization of HIV-2$_{7312A-V434M}$ in the presence of a sub-inhibitory concentration of sCD4. IC90 titers are shown and the dashed line is the detection limit. C) Top panel shows results of CD4bs Abs in plasma detected by competition ELISA against b12 mAb (left), competition ELISA against sCD4-Ig (middle), and inhibition of gp120-Ig binding to cell surface CD4 (right). Lower panel shows results of CD4i Abs in plasma detected by competition ELISA against 17b mAb (left), competition ELISA against ED47 mAb (middle) and inhibition of FLSC-Ig binding to cell surface CCR5 (right). Results of NVS5, NVS9, and NVS10 are shown as circles, squares, and triangles, respectively.

We have discovered that analysis of memory B cells (B$_{Mem}$) can be used to identify prior antibody (Ab) responses to a particular known antigen. Such antibody responses are often not detectable by analysis of contemporaneous plasma Ab samples. Our results show that analyzing the diversity of monoclonal antibodies (mAbs) made by B$_{Mem}$ complement serological studies in attempts to correlate Ab specificities and protective immunity against a particular pathogen or antigen. Thus certain embodiments of the invention are directed to a method for identifying mAb that specifically bind to a know antigen that were made by an animal known to have been exposed to the antigen in the past, but which mAb are not presently detectable in a contemporaneous serum sample from the animal. Using this method, we have discovered that certain individuals who are elite controllers (EC) or natural viral suppressors (NVS) infected with HIV-1 have B$_{Mem}$ that are capable of making anti-Env mAb that are not detectable in a contemporaneous serum sample. The newly discovered anti-Env mAb have therapeutic significance because they were made by a rare group of individuals who were able, without drug therapy, to self-control a potentially deadly HIV-1 infection. In particular we discovered that mAB against the antigen CD4i have particular utility in treating HIV-1 infection. Such antibodies include N5-I1, N5-I2, N5-I3, 7b, ED47, and A32 (described herein). The new methods can be used to make monoclonal antibodies against any molecule that can be made antigenic, i.e. able to elicit an immune response in a host.

In the course of our studies, we not only identified new therapeutically useful antibodies, we developed a new method for making fully human monoclonal antibodies that specifically bind to a known antigen without using hybridoma cell fusion, phage display, or EBV transformation. Certain embodiments are directed to this new method and to the recombinant mAb made using it, specifically the newly discovered anti-HIV Env mAb described below.

Certain other embodiments are directed to a method for determining if an animal has been exposed to or infected with a known antigen when the animal is not presently making antibodies that specifically bind to the known antigen.

The nature of antiviral Ab responses during the key window of early acute HIV-1 infection is important for vaccine and drug design but is inherently difficult to assess. Ab specificities are likely to change significantly once chronic infection has been established, particularly under conditions where replication and antigenemia are limited by natural processes or drug intervention. Thus, past responses are unlikely to be reflected in present-day samples. Several groups are attempting to overcome this limitation by establishing networks that follow high-risk individuals in hopes of obtaining samples at the earliest possible times after acute infection. However, these efforts face numerous practical and logistical limitations, particularly in resource poor settings.

Long-lived $B_{Mem}$ provide an historical archive of Ab specificities that have occurred over much of the host lifespan (11). For example, $B_{Mem}$ can persist for 50 years after vaccination with vaccinia (12). By contrast, circulating Abs usually decline after antigen clearance. For instance, up to half of vaccinees lose protective Abs within a few years after vaccination with the HBV vaccine (13). On the other hand, HBV-specific $B_{Mem}$ persist in the absence of Ab and set the stage for rapid protective Ab responses upon exposure to HBV or the vaccine (14-17). These studies provide strong collective evidence that $B_{Mem}$ provide a highly stable record of prior Ab responses. Since $B_{Mem}$ persist for much of the host's lifespan, we reasoned that they should provide a record of such early responses and might offer a new window through which Ab specificities can be correlated with viral control in our NVS cohort.

Analyses of the $B_{Mem}$ compartment in HIV-1 infected persons are inherently difficult because HIV-1 pathogenesis includes significant immune dysfunction that extends to humoral immunity (18, 19). Fortunately, EC or NVS who maintain a relatively intact immune systems provide an opportunity to census the archive of humoral immunity elicited by the HIV-1 Env protein during infection. Accordingly, we employed a local NVS cohort (5) to compare and contrast archived $B_{Mem}$ specificities with contemporaneous plasma Ab responses directed against two highly conserved, cross-reactive neutralization targets on gp120: the CD4bs and the coreceptor binding domain, which includes a subset of CD4-induced (CD4i) epitopes (20-23).

NVS Volunteers

Figure 4:
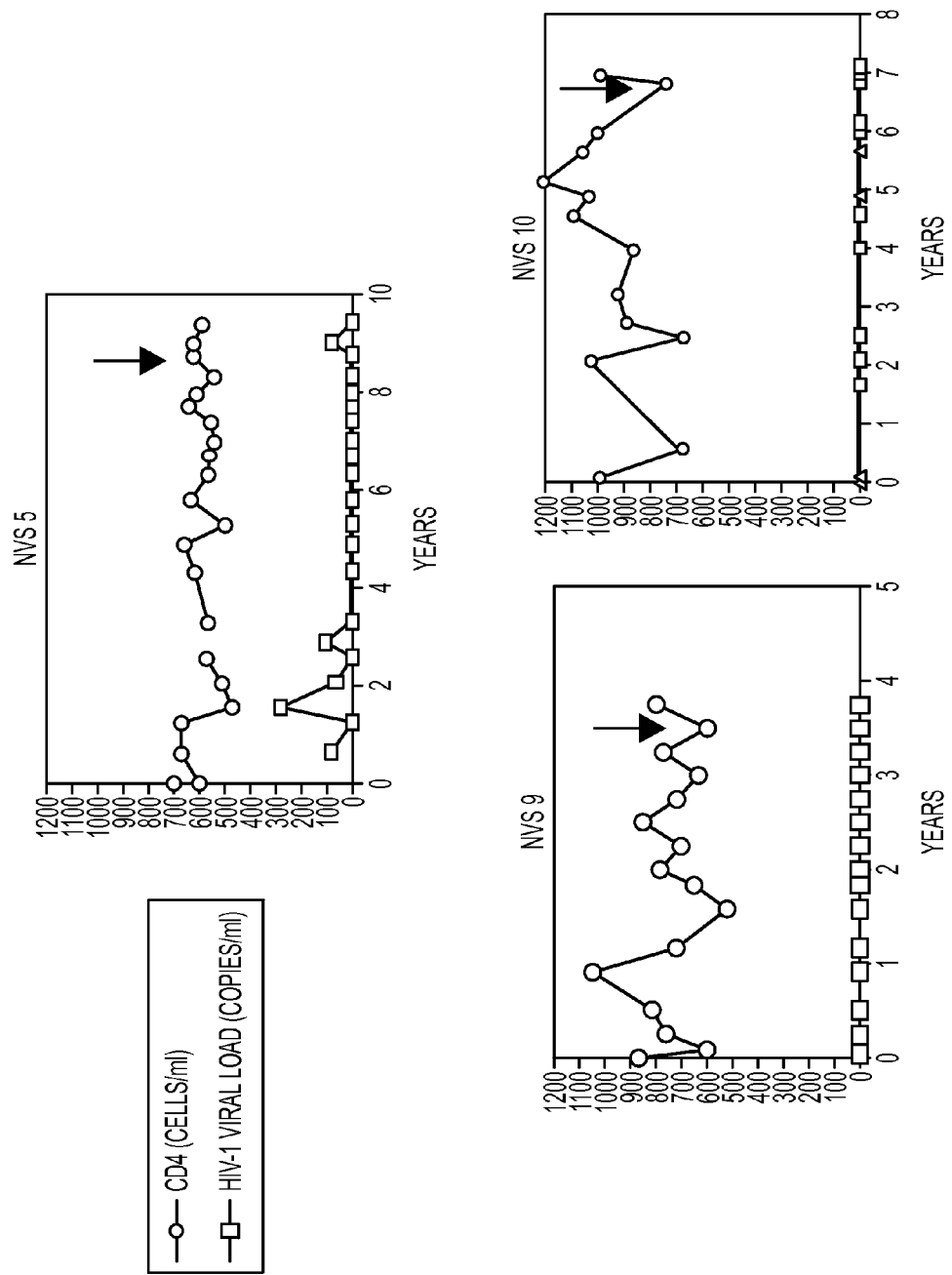
FIG. 4. Viral loads and CD4 counts for NVS5, NVS9, and NVS10. All donors had stable CD4 count (circle, cells/ml). Viral load (square) detection limit was 75 copies/ml. A less sensitive viral load assay (<400 copies/ml) was used at several time points for NVS10 (triangles). Arrow indicates the time point of sampling for this study.

During the early phase of studies to define anti-Env Ab responses in our NVS cohort, we observed an apparent discordance in specificity between plasma Abs and $B_{Mem}$ that specifically bind to HIV-1 Env epitopes. More detailed studies were carried out on three volunteers, NVS5, NVS9, and NVS10, to explore this observation. The clinical characteristics are shown in Table 1 for each volunteer. The times since diagnosis were 5 years for NVS9 (53 year old African American male, risk factor=intravenous drug use), 13 years for NVS10 (57 year old African American female, risk factor=sex), and 17 years for NVS5 (50 year old African American female, risk factor=sex). None of these individuals received antiretroviral therapy during this time. Total B cell and $B_{Mem}$ frequencies are in the normal range [19] indicating the lack of global immune dysregulation in these individuals (Table 1). This is also supported by undetectable viral loads and normal CD4+ T cell counts. NVS9 and NVS10 suppressed viral replication to undetectable levels (<75 copies per ml of plasma) at all times tested (FIG. 4). By contrast, NVS5 had transient spikes of low-level viremia of up to approximately 300 copies per ml of plasma during the first three years of observation followed by approximately 4 years of control to undetectable levels (FIG. 4). Interestingly, a viral spike of approximately 100 copies per ml of plasma was observed shortly after specimens were obtained for the studies reported here. As discussed below, this might be significant in that NVS5 is the only volunteer of the three that had significant neutralizing Ab titers. It could reflect that at 17 years post-diagnosis, NVS5 has been infected the longest of the three NVS volunteers studied here. Importantly, all three donors had stable CD4+ T cell counts in the normal range throughout the time of observation (FIG. 5). Taken together, these data show that the three NVS volunteers maintain undetectable viral loads over many years in the absence of antiretroviral therapy and that in terms of gross phenotypes, their lymphocyte subsets are normal.

Despite apparent strong control of viral replication, all three NVS volunteers remained seropositive for Env epitopes at the time that specimens were collected. This was determined by three ELISA formats using $gp120_{Ba-L}$, a full length single chain (FLSC) fusion protein of $gp120_{Ba-L}$ and CD4 D1D2, or $gp140_{Ba-L}$, all based on the HIV-$1_{Ba-L}$ Env protein, as described in the Examples. As shown in FIG. 1A, each volunteer had plasma Abs that recognize each of the three antigens with titers in the range of $10^{-3}$ to $10^{-4}$. These ELISA formats do not permit epitope-specific discrimination but they do show that the three NVS volunteers are seropositive for Env epitopes at low levels despite undetectable viral loads at the time of specimen collection.

TABLE 1

Characterization of three NVS donors

| | Year of Diagnosis | Sampling Date | B cell (PBMC %)* | $B_{Mem}$ (B cell %)* | Plasma IgG (mg/ml)* |
|---|---|---|---|---|---|
| NVS5 | 1991 | July 2006 | 10.5 | 32.7 | 34.2 |
| NVS9 | 2003 | July 2006 | 10.8 | 52.8 | 13.6 |
| NVS10 | 1995 | July 2006 | 10.6 | 36.0 | 18.4 |

*Normal values were described in literature (18, 19)

Plasma CD4bs and CD4i Ab Titers

Figure 1B:
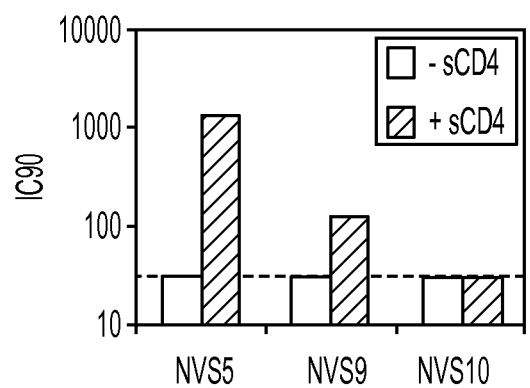
Figure 1C:
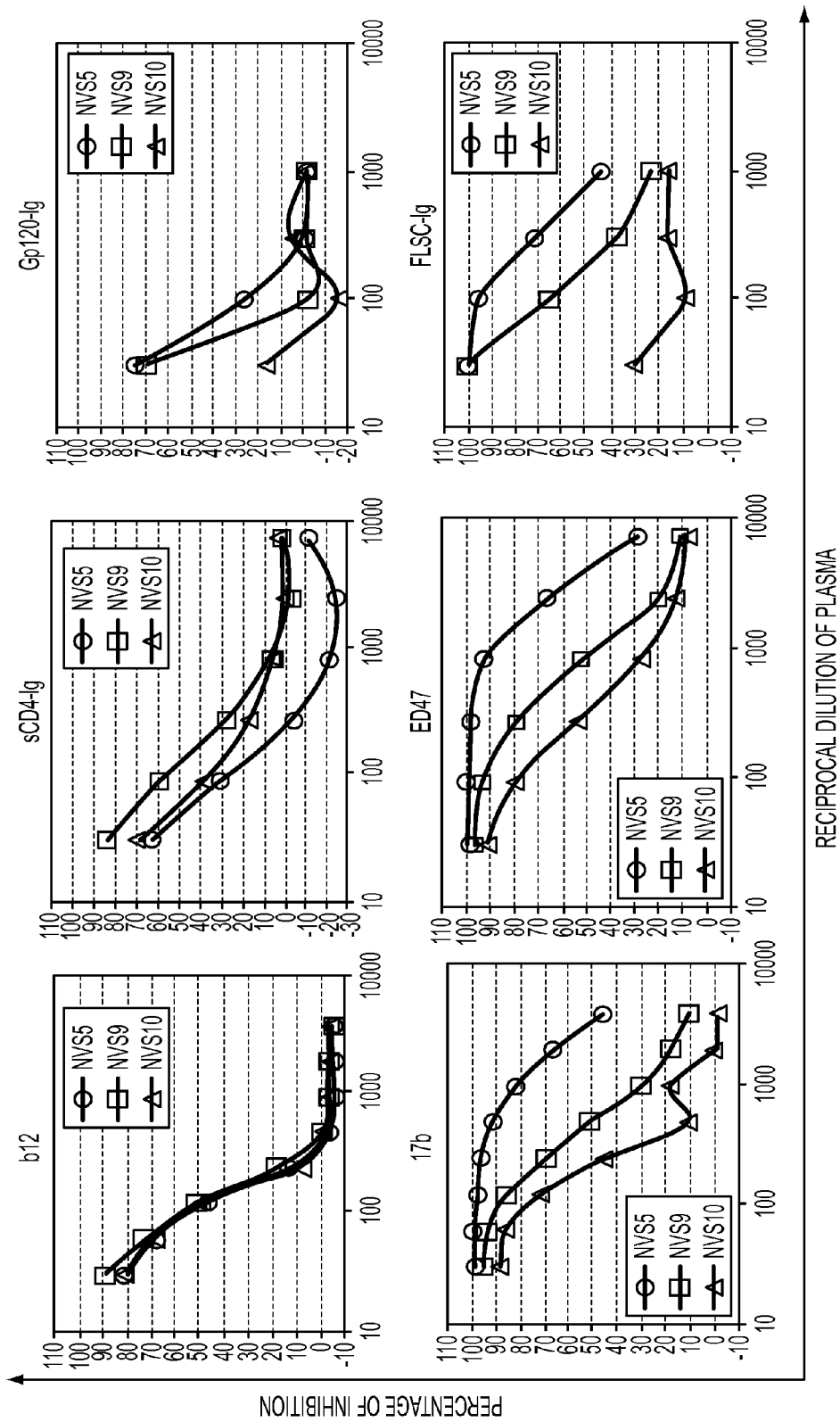

Of the known conserved neutralization epitopes of HIV-1, those associated with the CD4 and co-receptor binding sites of gp120 are the most consistently immunogenic during infection (20, 24). For this reason, our early analyses focused on the plasma and $B_{Mem}$ responses to these epitopes in NVS volunteers. We probed the NVS plasmas for CD4bs Abs using three independent competition assays. First, serial 0.5 log plasma dilutions were evaluated for their ability to block binding of a limiting concentration of biotinylated mAb b12 to $gp120_{Ba-L}$ captured on ELISA plates. Monoclonal Ab b12 recognizes a highly conserved neutralization epitope associated with the CD4bs of gp120 (25). Second, serial 0.5 log plasma dilutions were evaluated by capture ELISA for their ability to block binding of sCD4-Ig to plates captured with $gp120_{Ba-L}$. Third, serial 0.5 log plasma dilutions were evaluated by flow cytometry for their ability to block the binding of APC-tagged gp120-Ig to the CD4+ T cell line, CEM-NK$^r$. As shown in FIG. 1C, upper panel, the plasma Ab responses to CD4bs epitopes were nil to marginal in all three NVS volunteers, with the strongest competitions in any assay format being only 0.5 log above the limit of detection. For example, the half-maximum competition values for each of the plasmas for blocking the binding of b12 were approximately $10^{-2}$, whereas the background competition is $10^{-1.5}$. These marginal titers in each of the three independent assay formats showed that the NVS volunteers had little in the way of ongoing plasma Ab responses to CD4bs epitopes. As described below, this stands in stark contrast to high frequencies of CD4bs specific $B_{Mem}$ in two of these three individuals.

Similar analyses were also carried out for broadly cross-reactive CD4i Abs that are found in most HIV-1-infected individuals at titers in the $10^{-3}$ to $10^{-5}$ range by a CD4-triggered neutralization assay using an HIV-2 indicator virus that selectively detects these Abs (20). Using this neutralization assay (FIG. 1B), NVS5 had CD4i-neutralizing Abs with an IC90 titer of approximately $1.5 \times 10^{-3}$. As expected for CD4i Abs, neutralization was observed only in the presence of limiting concentrations of sCD4 (FIG. 1B). By contrast, NVS9 and NVS10 showed low and negative titers, respectively, in this assay. Thus, the rank order of neutralization in the CD4-triggered assay is NVS5>NV9>NVS10.

The CD4i neutralization rank order was confirmed by blocking studies in which the NVS plasmas were probed for competition with the binding of two biotinylated CD4i mAbs, 17b and ED47, to FLSC in ELISA and with the binding of fluorescent FLSC-Ig to CCR5 on CfT2h-CCR5 cells. As shown in FIG. 1C, lower panel, NVS5 plasma had higher competition titers in all three assays than NVS9 and NVS10. The differences in competition titers for 17b or ED47 were less apparent between NVS9 and NVS10, although the titers were slightly higher for NVS9. By contrast, plasma from NVS9 blocked the binding of fluorescent FLSC-Ig to CfT2h-CCR5 cells at a titer of approximately $2 \times 10^{-2}$ whereas no competition was observed for plasma from NVS10. Taken together, the competition data confirm that the rank order of CD4i Ab responses is NVS5>NVS9>NVS10.

Neutralizing Abs in NVS Plasmas

NVS plasmas were also evaluated in two independent 'conventional' neutralization formats to further assess their rank order of activity. In the first format, plasma samples from the three NVS volunteers were evaluated using a PBMC-based assay as described in Materials and Methods. As shown in Table 2, despite the absence of anti-CD4bs Abs, the NVS5 plasma exhibited remarkably broad cross-reactivity and neutralized all ten isolates tested with IC50 titers ranging from $1.8 \times 10^{-2}$ to $6.8 \times 10^{-3}$. By contrast, plasmas from NVS9 and NVS10 neutralized three often isolates and one often isolates, respectively, at marginal titers in the range $4 \times 10^{-1}$ to $6 \times 10^{-1}$.

In the second format, whole IgG was purified from NVS plasma and evaluated in a cell-line based pseudovirus assay. In accordance with the plasma neutralizing activity, NVS5 IgG neutralized eleven of the twelve pseudoviruses with IC90 at IgG concentrations ranging from approximately 10 μg/ml to 200 μg/ml (Table 3). On the other hand, IgG from NVS9 and NVS10 neutralized five of twelve and three of twelve pseudoviruses, respectively, at titers the range of approximately 10 μg/ml to 290 μg/ml (Table 3). It should be noted that in both assays (Tables 2 and 3) plasmas or IgGs from NVS9 and NVS10 selectively neutralized X4 viruses or relatively sensitive R5/dual-tropic viruses. Taken together, these data show that the rank order for neutralization is NVS5>>NVS9≥NVS10 in two independent assay formats, indicating that NVS5 has an ongoing Ab response that is broadly neutralizing whereas NVS9 and NVS10 have very weak ongoing neutralizing Ab responses that are narrow in specificity. It should be noted that NVS5 is the only subject of the three to exhibit transient, low level viremia and that the specimens analyzed above were taken just before an increase in viral load to detectable levels (FIG. S1).

Natural Viral Suppressors Preserve High Frequency of $B_{Mem}$ that Specifically Bind to Conserved Epitopes of the HIV-1 Env Protein Independent of Serological Status The above results show that while there are only small differences in total circulating Ab titers to gp120 or gp140 epitopes among the NVS subjects, there are marked differences in Ab fine specificity. The Ab responses to CD4bs epitopes were weak to nil in all three subjects and the rank order for circulating Abs to CD4i epitopes was NVS5>NVS9>NVS10. Collectively, these data provide no apparent relationship between plasma Ab specificity and control of infection in the three NVS subjects. However, antigen loads are likely to be low in these individuals, because they control their infections. We sought to determine whether significant Ab responses had occurred in the past, which waned as antigen burdens decreased. If this were so, circulating Ab responses would provide a poor indication of the initial responses that might correlate with the control of infection.

Since $B_{Mem}$ persist for much of the host's lifespan, we reasoned that they should provide a record of such early responses and might offer a new window through which Ab specificities can be correlated with viral control in our NVS cohort. To test this hypothesis, we evaluated the NVS subjects for the presence of $B_{Mem}$ that make antibodies that specifically bind to the Env epitopes discordant with those recognized by plasma. First, we established culture conditions and assays to detect anti-Env Abs secreted by single $B_{Mem}$ precursors meaning that these are monoclonal antibodies. Our culture conditions were based on those described to polyclonally activate $B_{Mem}$ to divide and secrete Abs (26, incorporated herein by reference). Preliminary studies showed that culturing 50 to 100 bead-enriched $B_{Mem}$ together with feeder cells (PBMCs from unrelated donors irradiated for 7-14 days) was sufficient to induce high enough levels of IgG anti-Env Abs to permit ready analysis of Ab specificity by ELISA. Each culture supernatant was tested in three ELISA formats using $gp120_{Ba-L}$, FLSC, or $gp140_{Ba-L}$, as described in the Examples. This approach enabled us to differentiate Abs that specifically bind to CD4bs and CD4i epitopes from each other and from other HIV-1 Env epitopes.

This strategy was validated using human mAbs that specifically bind to CD4bs, CD4i, and other HIV-1 Env epitopes. The CD4bs mAbs, b12 and m14 as well as CD4-Ig, reacted selectively with gp120, confirming that reactivity with gp120, but not FLSC, is indicative of Abs that specifically bind to CD4bs epitopes (FIG. 5-A, middle). By contrast, the CD4i mAbs 17b, ED47, and A32 reacted with FLSC but reacted poorly when gp120 was used in lieu of FLSC, confirming that reactivity with FLSC but not gp120 detects CD4i specific mAbs (FIG. 5-A left).

We were also able to detect Abs that specifically bind to other epitopes that are expressed on gp120 as shown by reactivity with mAb 2G12 that binds to carbohydrate epitopes (FIG. 5-A, right). In this case, there was no difference in binding whether FLSC or gp120 was captured on the plate. Finally, we also evaluated each culture supernatant for reactivity with $gp140_{Ba-L}$. Because we are comparing binding of single supernatants to multiple Env preparations, it was important to standardize the ELISAs using known mAbs to detect specific binding at levels expected for Abs in $B_{Mem}$ culture supernatants. The data shown in FIG. 5-B are indicative of the degrees of binding for different mAbs to gp120, FLSC, or gp140 when their IgG concentrations are at levels typical of those found in supernatants from cultures of activated $B_{Mem}$.

In the experiments described herein, selective reactivity with FSLC is taken as putative CD4i specificity, selective reactivity with gp120 is taken as putative CD4bs specificity, and reactivity with all antigen preparations or gp140 alone is denoted as 'Other' Abs. We have confirmed this strategy by mAb isolation from activated $B_{Mem}$ (FIG. 3 and in preparation) and by control studies using either $B_{Mem}$ isolated from HIV-1 naïve individuals or from CD19+ CD27- cells from these NVS subjects. In both cases, no Env-specific precursors were observed.

Using these assays, we censused $B_{Mem}$ for precursors that recognize CD4bs, CD4i, and "Other" Env epitopes. An example of the type of ELISA data generated is shown in FIG. 2A for NVS10. In this subject, the $B_{Mem}$ precursors were approximately equal for CD4i, CD4bs, and 'Other' specificities in the range of 200 to 300 precursors per million $B_{Mem}$ (FIG. 2B, C). Further subdivision within the 'Other' category is apparent in FIG. 2A with approximately 70% (10/14) of the $B_{Mem}$ precursors selectively recognizing the gp140 oligomer. We are hesitant at this point to read too much into the apparent specificity for oligomer as the gp140 preparations are heterogeneous in size and perhaps in native structures once they are adsorbed to plastic. This caveat does not change the conclusion that CD4i and CD4bs $B_{Mem}$ precursors are prevalent in NVS10, whereas the levels of circulating anti-Env Abs having the same specificities in this individual were very low. A similar picture was found for NVS9 (FIG. 2B, C), who also had approximately equal frequencies of $B_{Mem}$ that make antibodies that specifically bind to CD4i, CD4bs, and 'Other' Env epitopes in the range of 400 to 600 precursors per million $B_{Mem}$. Again, the prevalence of $B_{Mem}$ precursors make CD4i and CD4bs epitopes was discordant with the titers of circulating Abs to these epitopes.

$B_{Mem}$ precursor analysis for NVS5 presented a different and potentially important picture. This individual had very low levels of CD4bs specific $B_{Mem}$ at approximately 20 precursors per million $B_{Mem}$. This corresponds to 5.6% of the total Env specific $B_{Mem}$ precursors for this individual and is barely above our limit of detection in this assay format of 10 precursors per million $B_{Mem}$. By contrast, the $B_{Mem}$ precursor pool was dominated by $B_{Mem}$ that make antibodies that specifically bind for CD4i and 'Other' Env epitopes, corresponding to 50% and 44.4% of detectable Env specific precursors, respectively (FIG. 2B, C). The absence of CD4bs specific plasma Abs and especially the very low levels of CD4bs specific $B_{Mem}$ strongly indicates that the broad neutralizing Ab response for NVS5 is not due to Abs that specifically bind to CD4bs epitopes.

Figure 3:
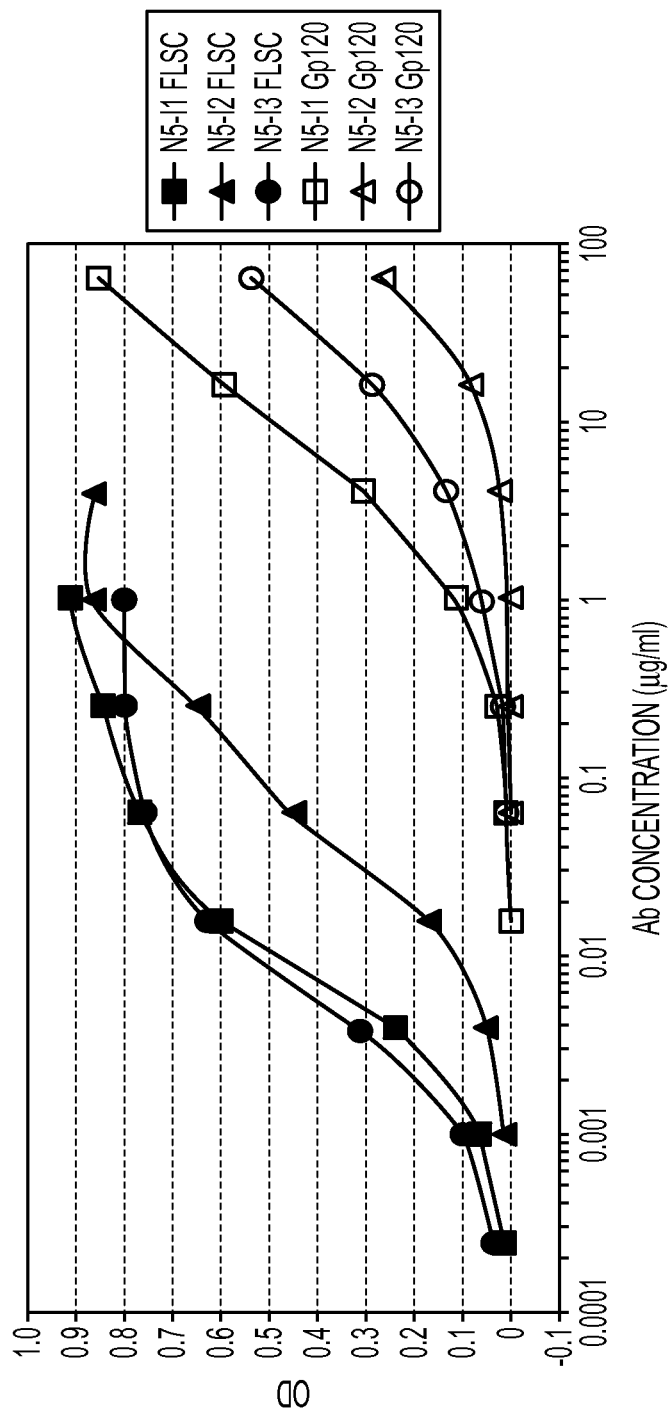
FIG. 3. Isolation of three CD4i mAbs. Three mAbs were cloned from CD4i Ab positive wells of NVS5 as described in Materials and Methods. ELISA curves for selective reactivity of the mAbs to FLSC (filled symbol) relative to gp120$_{Ba-L}$ (open symbol) are shown.

Because our conclusions are based on analysis of supernatants of $B_{Mem}$ activated under limiting dilution conditions, it was important to confirm that the mAb specificities found in the supernatants match those of the $B_{Mem}$ themselves. This was addressed by mAb isolation using a new algorithm developed for this purpose and described in detail below. This new algorithm enabled us to identify the specific VH and VL chains that encode a specific mAB and to clone cells transfected with the genes for the appropriate VH and VL chains to express and secrete large amounts of fully human Ab without using hybridoma cell fusion technology, phage display or EBV transformation. As proof of principle for the new method, we identified $_{BMem}$ cells in wells whose supernatants were positive for CD4i antibodies, and we cloned three mAbs (N5-I1, N5-I2, and N5-I3) from them. As shown in FIG. 3, all three IgG1 mAbs showed strong reactivity with FLSC and low reactivity with gp120 in ELISA. Furthermore, each mAb was encoded by the VH(1-69) gene segment that is found in the majority of CD4i mAbs published to date [27]. This result was also confirmed by an ongoing analysis of 23 additional Env-specific mAbs isolated from $_{BMem}$ cultures in our NVS cohort (in preparation). Taken together, the data described above strongly suggest that the specificities of $_{BMem}$ should be evaluated as a component of studies aimed toward correlating Ab specificity and control of HIV-1 infection.

The experiments described herein show that analyses of $B_{Mem}$ provides a facile and highly informative method for viewing past Ab responses against cross-reactive HIV-1 Env epitopes in clinical cohorts where these responses might not be paralleled by the circulating Ab pool. Our NVS cohort (5), which is comprised of HIV-1 infected individuals who control viremia to undetectable levels for many years without anti-retroviral therapy, is one such population. These individuals are expected to have low antigen burdens consequent to viral control and this should be reflected by simultaneously low steady state Ab responses to certain HIV-1 epitopes. Our serological analyses (FIG. 1) of reactivity with conserved receptor binding sites on gp120 are consistent with this prediction. Our data also agree with recent studies showing that elite controllers and HAART (highly active antiretroviral therapy)-treated patients with undetectable viremia have lower levels of both Env-binding and neutralizing Abs compared to viremic chronic progressors (9, 10). Nevertheless, our studies show that specificities to conserved neutralizing targets (CD4bs and CD4i epitopes) are clearly evident in the $B_{Mem}$ pool of two NVS subjects (NVS9 and NVS10) who had little or no cognate Ab titers at the time of plasma collection. Moreover, the high frequencies of these $B_{Mem}$ suggest that responses to CD4i and CD4bs epitopes were quite robust at some point during an earlier stage of infection. Using larger cohorts, it should now be possible to determine whether these archived responses correlate with NVS status or some form of transient immunological control that eventually wanes as viremia is cleared.

Our third NVS subject, NVS5, had broadly neutralizing Abs in the circulation as determined in the CD4-triggered and two conventional neutralization assay formats (Tables 2 and 3; FIG. 1B). This individual had the strongest binding Ab responses to CD4i epitopes of the NVS subjects while significant responses to CD4bs epitopes were not apparent. This pattern was also reflected in the $B_{Mem}$ pool where approximately 50% of the precursors were specific for CD4i epitopes and only a marginal 5.6% were specific for CD4bs epitopes.

TABLE 2

Neutralization in PBMC format

IC50 (dilution of plasma) for HIV-1 strain

| | BaL | ADA | 92BR020 | IIIB | 2044 | 2005 | 89.6 | SF2 | 92HT594 | 92HT599 |
|---|---|---|---|---|---|---|---|---|---|---|
| NVS5 | 380 | 520 | 1040 | 320 | 240 | 180 | 520 | 6800 | 320 | 320 |
| NVS9 | <30 | <30 | <30 | <30 | 40 | <30 | <30 | 60 | <30 | <30 |
| NVS10 | <30 | <30 | <30 | <30 | <30 | <30 | <30 | 60 | <30 | <30 |

TABLE 3

Neutralization in Env-pseudotyped virus format

| | IC90 (µg/ml of total IgG) for HIV-1 strain | | | | | | | | | | | | |
|---|---|---|---|---|---|---|---|---|---|---|---|---|---|
| | 6535 | APV6 | APV14 | APV17 | APV19 | BaL | BX08 | MN | NSC | SF162 | JRCSF | NL4-3 | VsVg |
| NVS5 | 134 | >300 | 144 | 128 | 125 | 193 | 112 | 203 | 67 | 90 | 12 | 32 | >300 |
| NVS9 | >300 | >300 | 260 | >300 | >300 | >300 | >300 | >300 | 80 | 243 | 9 | 25 | >300 |
| NVS10 | >300 | >300 | >300 | >300 | >300 | >300 | >300 | >300 | 201 | >300 | 80 | 136 | >300 |

It has recently been posited that the broadly neutralizing activity seen in rare HIV-positive individuals is attributed to Abs directed against the CD4bs (6, 7) and that natural or vaccine-induced control of infection must rely on such specificity. Because one mAb that specifically binds to a CD4bs epitope is broadly neutralizing (25), there is intense interest in identifying such responses in vivo as a correlate of protection (6, 7). By contrast, we discovered that NVS5 developed little or no circulating Ab response or $B_{Mem}$ precursors for CD4bs epitopes over the course of infection yet harbored broadly neutralizing immunoglobulin activity. Specifically, we discovered that NVS5 had $B_{Mem}$ precursors for CD4i epitopes that appear to be equally important for controlling the HIV-1 infection in this individual. In fact, based on our data, it is unlikely that CD4bs-specific Abs contributed to viral control in NVS5.

NVS5 was also distinct in that there was a good specificity match between the circulating Ab response and the $B_{Mem}$ precursor pool. Notably, NVS5 was the only individual in our cohort who exhibited transient, low level viremias in the range of 100 to 400 copies during the first three years of observation and again in the eight year of observation, shortly after the specimens studied above were collected. It is likely that the neutralizing Abs observed in the plasma of NVS5 were elicited in response to the increase in viral load that occurred around the time that the test specimens were collected. Since subsequent analyses of viral loads (FIG. 4) indicated that this rebound is being controlled, NVS5 offers a unique opportunity to implicate particular Ab specificities in the control of HIV-1 infection.

Importantly our results show that CD4i-specific $B_{Mem}$ were present at high frequencies in all three NVS subjects, even though two of the NVS subjects who exhibited tight control of viremias had nil to low levels of circulating Abs that specifically bind to CD4i epitopes. By contrast, the third subject NVS5 exhibited much higher titers of Abs that specifically bind to CD4i epitopes in each of the assay formats. This observation is consistent with boosting of these responses by transient viremia and implicates CD4i Abs in the dampening of viral replication in NVS5. Although we cannot yet establish causality between viral control and the presence of CD4i specific Abs alone in NVS5; they are consistent with our recent demonstration of a correlation between viral control and circulating Abs that specifically bind to CD4i epitopes in rhesus macaques immunized with a version of FLSC in which the CD4 component was derived from rhesus macaques (rhFLSC) [28]. It is also relevant that most HIV-1 infected individuals mount Ab responses to CD4i epitopes and that these responses appear around the time of initial viral control in people [29] and in our rhFLSC vaccine model in rhesus macaques [28]. Therefore, certain embodiments are directed to a method for treating HIV infection in a human by administering a therapeutically effective amount of anti-CD4i-specific antibodies, preferably fully human monoclonal anti-CD4i-specific antibodies, including those identified in our NVS cohort including the mAbs listed below. The new method for making mAB is not limited to humans, but can be adapted to make fully homologous mAb for any animal species. It thus has utility for making mAb for veterinary use.

Overall, our data show that comprehensive analysis of $B_{Mem}$ specificity pools is needed for more precise characterizations of antibodies that are effective in treating an infection, such as anti-envelope humoral responses, than are possible with serological analyses of plasma Ab responses alone. This view is obvious for subjects NVS9 and NVS10 where plasma CD4bs and CD4i responses were low to negative but where both sets of specificities are well-represented in the $B_{Mem}$ pool. Thus, in at least some individuals who strictly control viremia, serological responses under-represent the true spectrum of Ab response made by that individual at times when the virus was being brought under control. Comprehensive analysis of $B_{Mem}$ specificity pools is also needed for more precise characterizations of antibodies against other pathogens in other infectious diseases since the level of circulating antibodies may be much lower in titer and less broad in specificity than the memory B cell archive.

Certain embodiments of the invention are directed to the new monoclonal antibodies set forth herein.

Method for Making Fully Human Monoclonal Antibodies

In the process of conducting the experiments described above to identify particular mAb-producing memory B cells, we developed a new method for making fully human mAb that specifically bind to a known antigen that obviates many of the problems encountered with conventional methods such as hybridomas, EBV transformation, and phage display. This new algorithm is based on the direct cloning and expressing heavy chain variable region genes (VH) and light chain variable regions genes (VL) from cultures of activated $B_{Mem}$ that contain antibody secreting cells for the target immunogen. The method is based on activating $B_{Mem}$ so that they differentiate into plasma cells in vitro that secrete the desired mAb. The $B_{Mem}$ were isolated from peripheral blood cells of individuals who have been either immunized with vaccines or naturally infected with a pathogen. In the studies described here, we isolated $B_{Mem}$ from HIV-infected self controllers. $B_{Mem}$ can also come from individuals who are making autoimmune responses, such as patients who have systemic lupus erythematosus (SLE), diabetes mellitus type 1, Crohn's disease, chronic fatigue syndrome, multiple sclerosis, myasthenia gravis, Parkinson disease, and many others. The autoimmune antibodies can be used as targets to obtain therapeutic molecules, such as therapeutic antibodies, that block the activity of the autoimmune antibodies. $B_{Mem}$ can also come from individuals who have a tumor or who previously have had a tumor and whose $B_{Mem}$ might include tumor-specific immune responses. Such tumors can include, for example, breast, ovarian, and uterine tumors; prostate tumors; lung tumors; skin tumors (e.g., melanoma, basal cell carcinoma, and squamous cell carcinoma); liver tumors, brain tumors, etc.

The $B_{Mem}$ cells are activated by culturing under conditions that permit them to differentiate into mAb-producing plasma cells. In the new algorithm immunoglobulin genes that make the VL and VH chains of an antibody that specifically recognize an antigen of interest (in the Examples described herein, the antigen of interest was one of the above-described HIV Env proteins) are cloned from the plasma cells and expressed in a convenient cell line such as 293T cells (a human embryonic kidney cell line) to produce the desired antibody. Any mammalian or insect cell line commonly used for expressing recombinant mammalian proteins can be used.

The algorithm is general in that it only requires the presence of the desired plasma cells at a minimal frequency of approximately 1% of the population to clone the immunoglobulin genes. In principle, it can be used to identify and isolate human mAbs from any individual who has mounted a conventional antibody response at some point in their life as $B_{Mem}$ are known to circulate for at least ten decades in the peripheral blood (45). The new method is not limited to humans, but can be used to produce antibodies for any animal that can mount an immune response.

We have reduced the algorithm to practice in the context of HIV-1 infected individuals who control viremia without antiretroviral therapy (5). These individuals have mounted strong immune responses to the HIV-1 envelope glycoprotein, Env, apparently early in infection, and control viremia to the point that antigen burdens are likely to be very low. Since the continuous presence of antigen is required to drive ongoing antibody responses, the circulating antibody titers against Env epitopes are typically low in these individuals (9). However we found that Env-specific $B_{Mem}$ persist even after antibody titers have diminished.

Identification of Plasma Cells Secreting Anti-Env Antibodies

PBMCs are isolated from a donor that is either infected or vaccinated with the pathogen of interest, or that has an autoimmune disease. In the Examples described herein, memory B cells were purified from the PBMC of three different HIV-self controlling donors by negative bead sorting (StemCell, Vancouver, Canada). $B_{Mem}$ were further enriched by positive cell sorting using anti-CD27 mircrobeads (Miltenyi Biotec, Auburn, Calif.,). B cell populations depleted of $B_{Mem}$ were also recovered to provide negative controls. Any method known in the art can be used to separate the $B_{Mem}$ cells.

Plasma cells secreting antibodies against the antigen of interest (one of the three anti-Env antibodies) were identified indirectly by causing Env-specific $B_{Mem}$ to differentiate into antibody-secreting plasma cells in tissue culture. This was accomplished by culturing approximately 100 $B_{Mem}$ isolated by cell sorting from the peripheral blood of HIV-1 infected individuals who spontaneously control viremia with CpG ODN2006, an agonist for Toll Like Receptor Nine (TLR9) that specifically binds to TLR9 and triggers the associated intracellular signaling cascade (47). Also included were IL-2, IL-10, and EBV as described (26, 48) by others. EBV has been shown to drive $B_{Mem}$ to differentiate into plasma cells in vitro (48). The published protocol was modified by the addition of 50,000 irradiated PBMCs from an unrelated donor in which the B cell fraction was depleted by cell sorting. The irradiated, B cell depleted PBMCs are designated as feeder cells hereafter. Persons of skill in the art will recognize other methods for activating memory B cells. Because as much as 10% of the total cell protein in a plasma cell can be the antibody, they are excellent sources of mRNA for cloning the VH and VL genes encoding the antibody made by this cell.

Figure 6A:
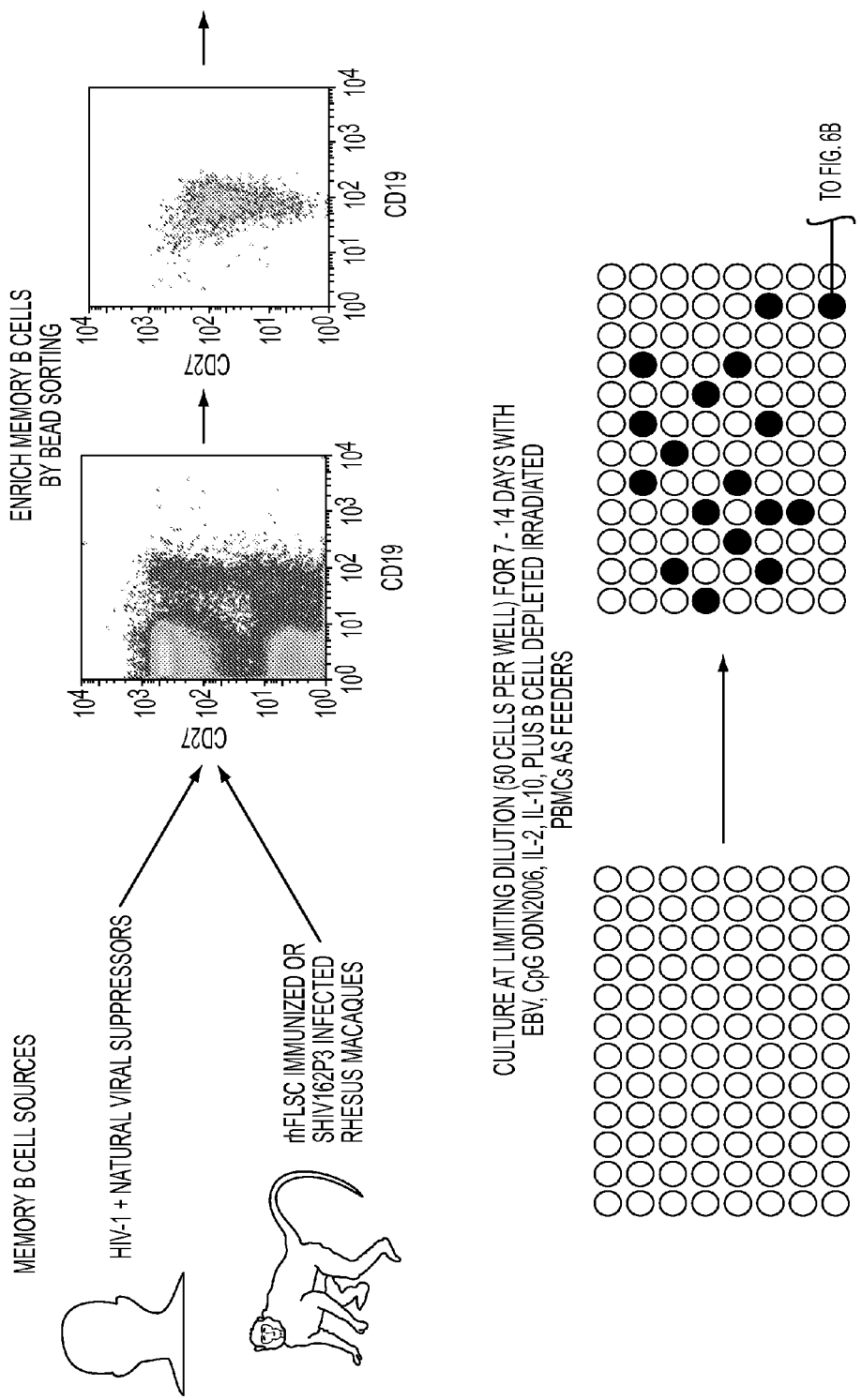
FIG. 6. Schematic of the steps used to identify plasma cells that secrete anti-Envelope antibodies.
Figure 6B:
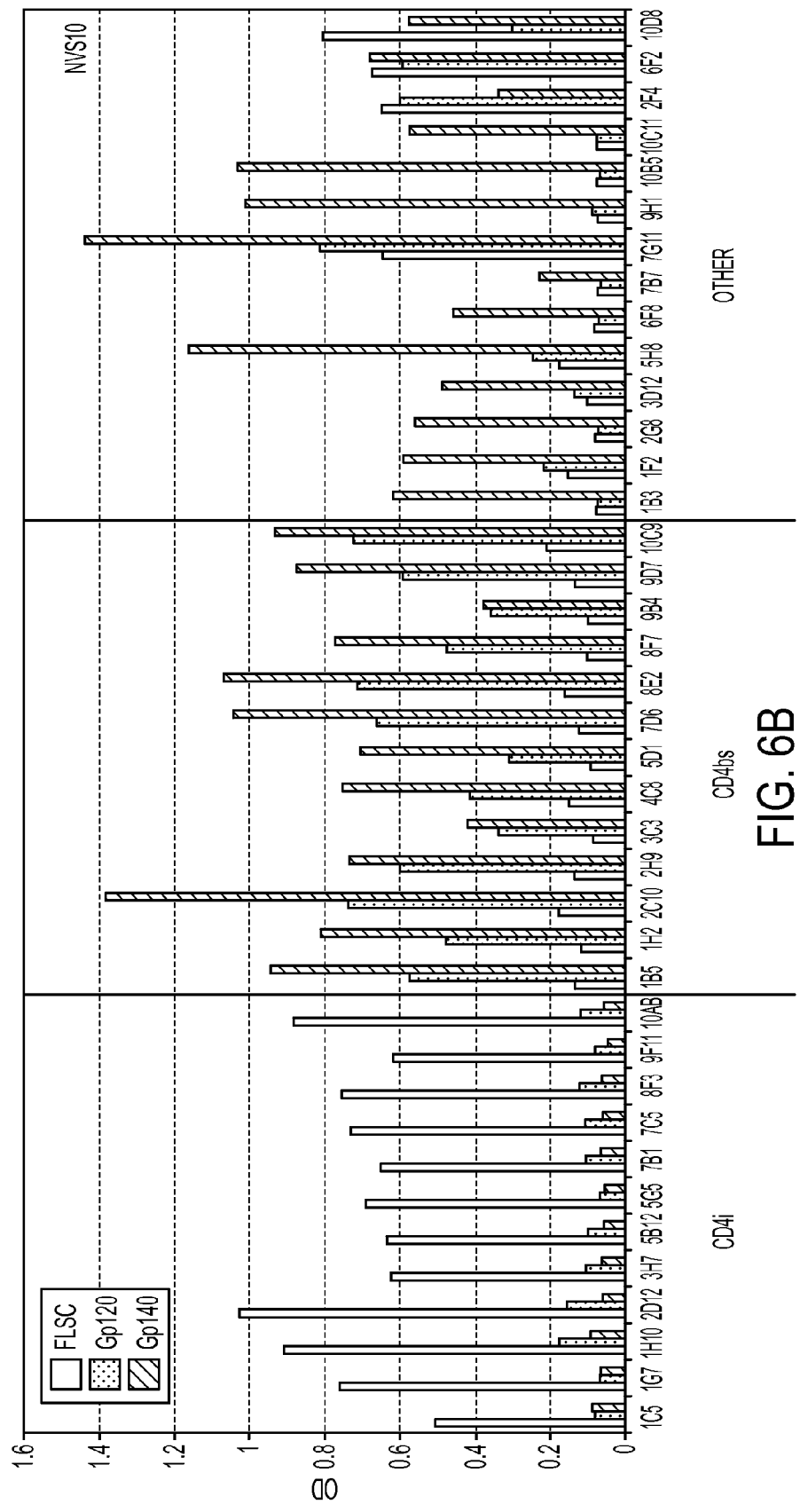

The new algorithm for isolating human mAbs has two major steps; identification of the plasma cells secreting the desired antibody and cloning the immunoglobulin VH and VL genes encoding the antibody. These steps are illustrated in FIG. 6 and described below.

Specifically one hundred $B_{Mem}$ per well were cultured in 96 well round-bottom plates with 1 μg/ml CpG ODN-2006, 5 ng/ml IL-2, 5 ng/ml IL10, 25% EBV supernatant, and feeder cells in RPMI1640-10% FSC medium with final volume of 200μl per well. The plates were incubated at 37° C. in a humidified incubator with 5% $CO_2$. Supernatants were collected a 2 week incubation and screened for total anti-HIV-1 Env Abs by using a mixture of anti-human λ-chain and κ-chain Abs. Supernatants were evaluated by ELISA for total immunoglobulin and for specific anti-Env antibodies using recombinant Env antigens. The Env antigen panel included the three recombinant proteins:

1. gp120, the receptor binding domain of the outer envelope glycoprotein, gp160, of HIV-1;
2. FLSC (full-length single chain) that is a fusion protein between gp120 and the gp120-binding domains of human CD4 (30). The gp120 and CD4 moieties of FLSC bind to one another forming a stable intramolecular complex that constitutively exposes CD4i epitopes that are recognized by broadly neutralizing antibodies elicited by HIV-1 infection (30, 20).
3. A stable oligomeric protein, gp140 that corresponds to the ectodomain of Env. These reagents permit the rapid identification of antibodies that specifically bind to CD4i epitopes, CD4 binding site epitopes (CD4bs), and 'Other' epitopes that include a variety of epitopes that are expressed on all forms of Env or only on oligomeric forms of Env.

Anti-Env+ supernatants were subsequently evaluated for individual light chain specificity and heavy chain isotype. Greater than 90% of the anti-Env+ cultures were IgG+. Total IgG in the supernatants was also quantified by capture ELISA, however any method known in the art can be used including RIA, radial immunodiffusion, or immunofixation. Total human IgG concentrations were typically in the range 0.5 to 2 μg/ml.

We established that culturing 100 $B_{Mem}$ in 96 well culture trays resulted in fewer than 10% of the wells being positive for anti-Env antibodies. By the Poisson statistic, we determined that the antibodies from any positive well are from the differentiation of a single Env-specific $B_{Mem}$ into a plasma cell. This was confirmed by isolating mAbs from random wells. Frequencies of HIV-1 Env specific $B_{Mem}$ precursors were estimated from the fraction of wells containing Env-specific Abs relative to the total wells and normalized as per million $B_{Mem}$ after correcting for $B_{Mem}$ purity. These frequencies are in good agreement with other studies measuring the frequencies of human $B_{Mem}$ for a variety of antigens [38]. An example of supernatant analysis from day 7 $B_{Mem}$ cultures is shown at the bottom of FIG. 1.

These results show that individual plasma cell clones secreting distinct anti-Env antibodies can be identified readily after culturing $B_{Mem}$ for 7-14 days under the culture conditions described above. This system is not limited to HIV-1 antigens. In principle, it can be used for any antigen to which a person can mount an antibody response. Furthermore, it is not limited to humans and should be applicable to any species for which antigen-specific $B_{Mem}$ can be found. This culture system provides the substrate for cloning and expressing immunoglobulin genes encoding the desired antibody.

Figure 7:
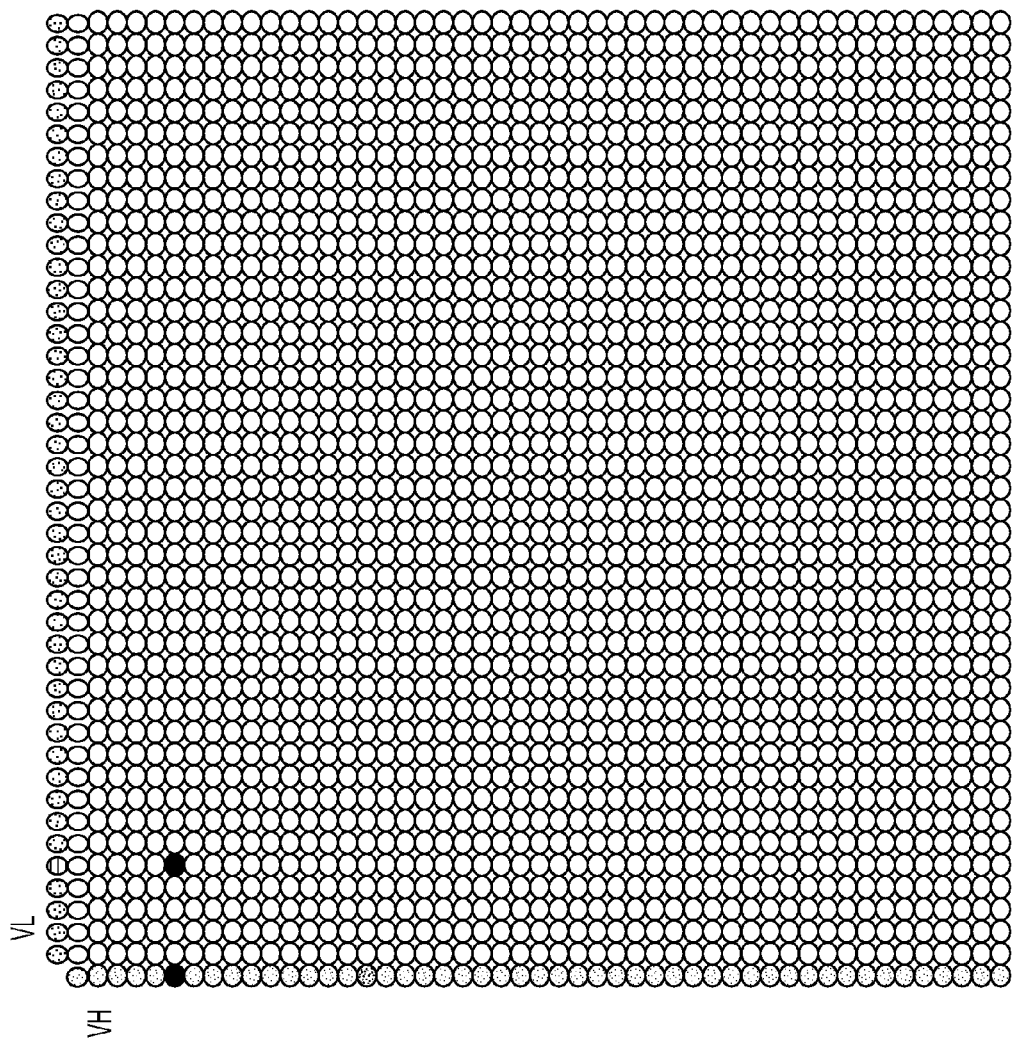
FIG. 7. Schematic showing the complexity of finding the correct VH-VL gene pair.
Figure 8:
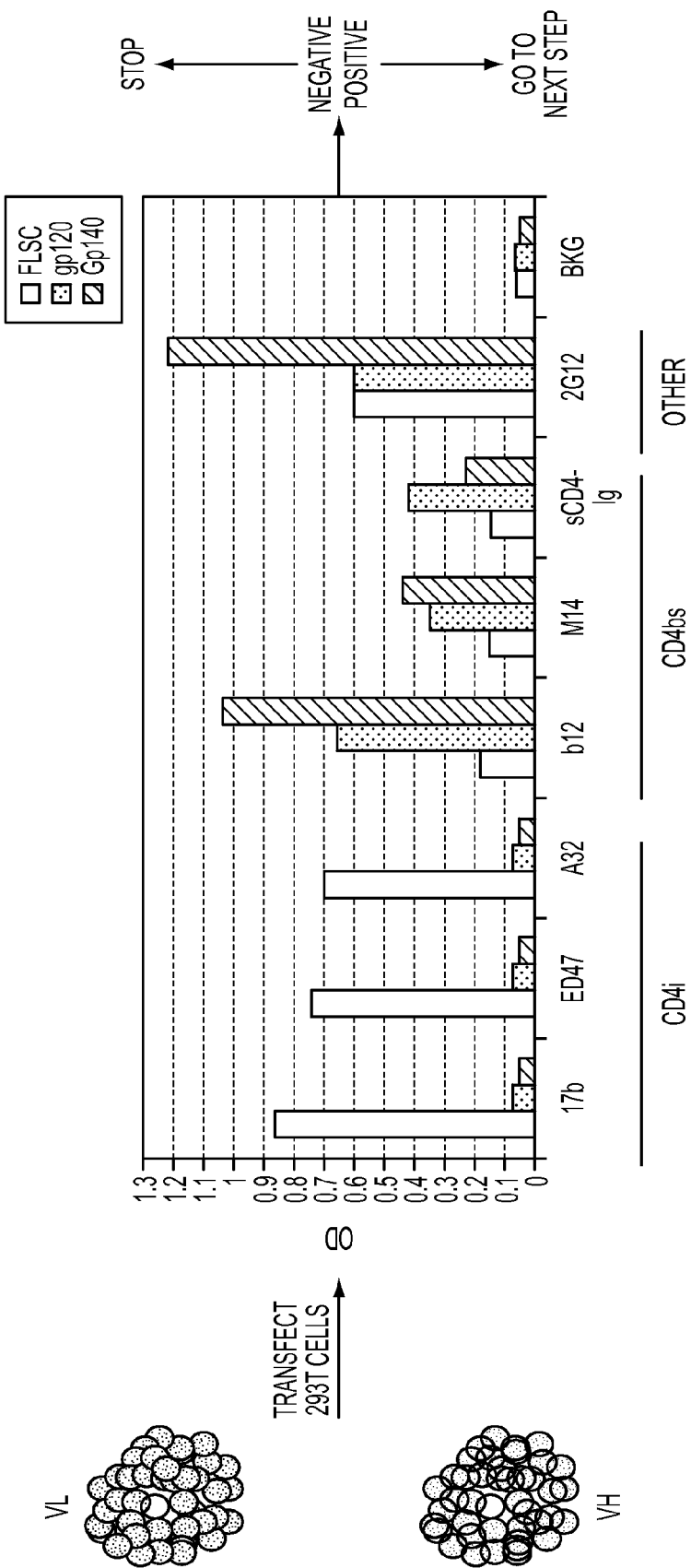
FIG. 8. Schematic showing the transfection of cells with a mixture (pool) of the cDNAs from the VH (variable heavy) and the VL (variable light) mini-libraries.
Figure 9:
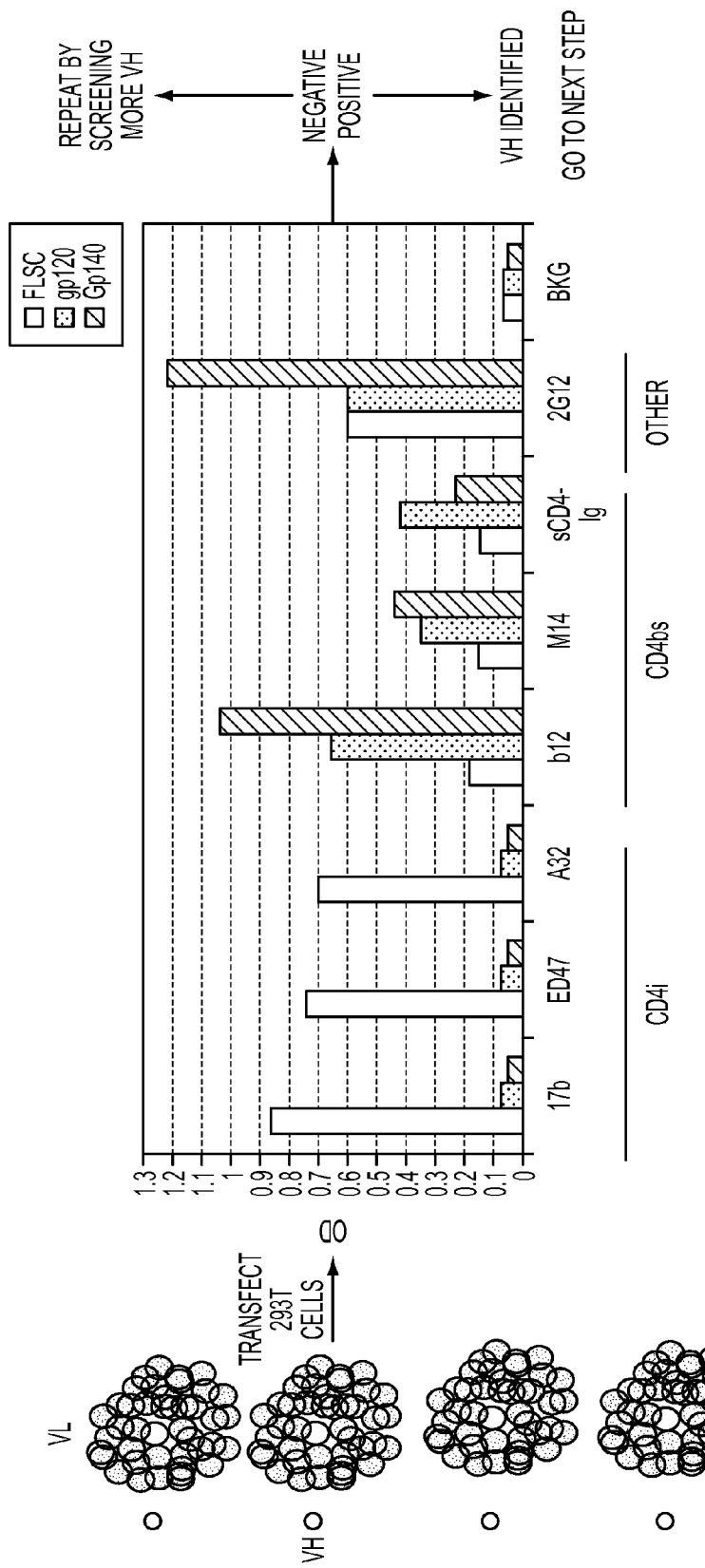
FIG. 9. Schematic showing how to identify the VH chain cDNA that makes the anti-Envelope antibody.
Figure 10:
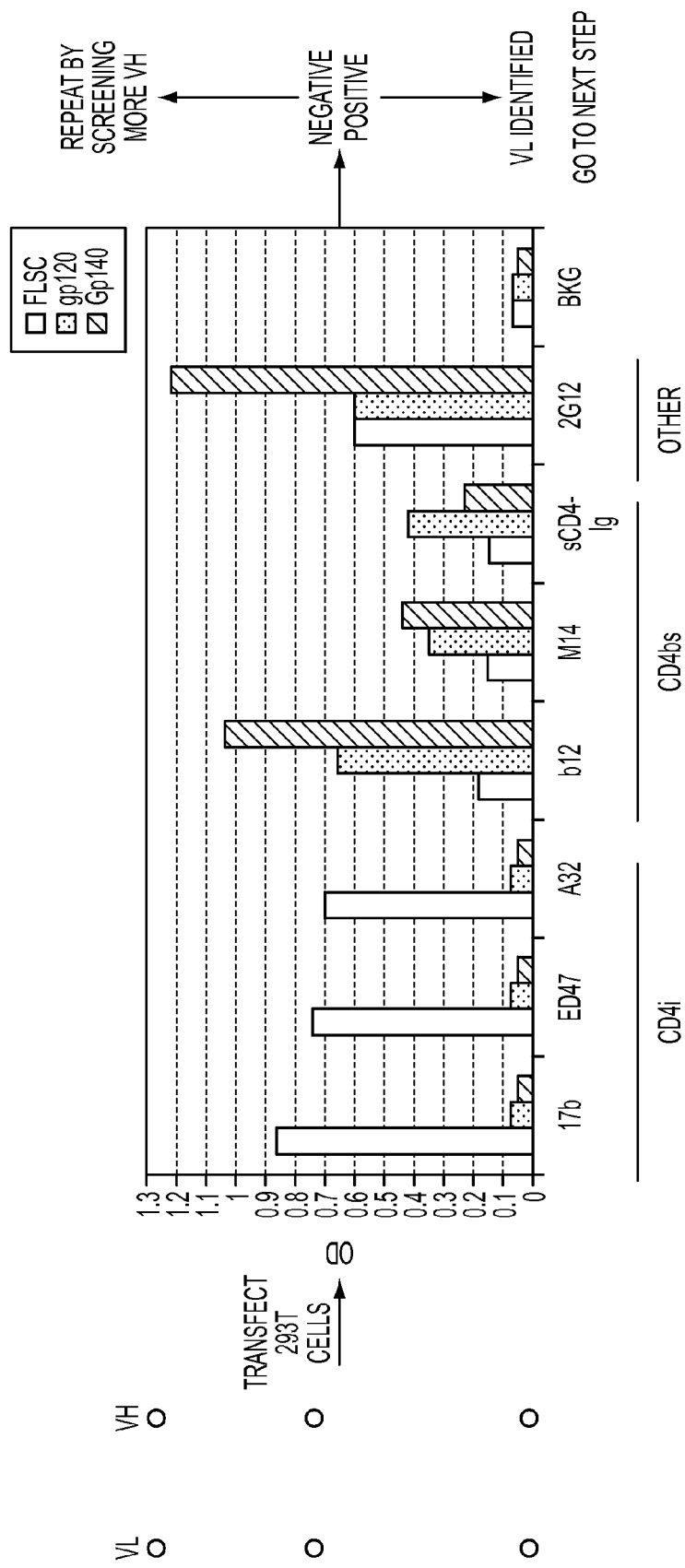
FIG. 10. Schematic showing how to identify the VL chain cDNA that makes the anti-Envelope antibody.

The new algorithm is directed to a method for making fully human monoclonal antibodies, or monoclonal antibodies from another species of animal, against a known antigen having the steps of:

1. obtaining a blood sample from an animal that has been exposed to the particular known antigen,
2. isolating a plurality of memory B cells from the blood sample,
3. culturing the plurality of the isolated memory B cells under conditions and for a sufficient time to permit the memory B cells to differentiate into plasma cells that stably produce monoclonal antibodies,
4. determining if the plasma cells produce the monoclonal antibodies that specifically bind to a particular known antigen,
5. if the plasma cells produce the monoclonal antibodies, then isolating total RNA from the plasma cells, and if the plasma cells do not produce the monoclonal antibodies, then repeating steps 2-4 until a plurality of isolated memory B cells is identified that differentiates into plasma cells that stably produce the monoclonal antibodies, Isolation of Env-Specific mAbs from $B_{Mem}$ Cultures Once a well has been identified that contains plasma cells that produce and secrete mAb that specifically bind to the known antigen (in our example anti-Env mAb) the next step is to clone the immunoglobulin genes encoding the desired antibody and to express them in a eukaryotic cell line to produce the antibody without requiring hybridoma technology, EBV transformation or phage display This presents a problem in that an antibody is made by the expression of two sets of genes, one encoding the heavy chain and another encoding the light chain. The antigen-binding site of an antibody is encoded by a VH gene (denoted VH for a generic heavy chain V region gene) and a VL gene, which is either a Vκ or Vλ gene (denoted VL for a generic light chain V region gene), each fused with the respective constant region genes. For a culture initiated with 100 $B_{Mem}$, theoretically, there will be 100 different VH genes and 100 different VL genes in the population. The problem is to find the correct VH and VL gene pair that encodes an anti-Env antibody out of a potential 10,000 VH-VL gene pairs for the population of 100 $B_{Mem}$. The complexity problem is illustrated in FIG. 7 where the correct VH and VL genes are represented by the blue circles. For clarity the FIG. 7 represents only 50 VH and 50 VL genes, but the complexity of the problem is apparent.

While it should be possible to transfect 10,000 different VH-VL gene pairs and to screen them by ELISA using high-throughput robotic methods, this is not practical. We were able to solve this 'complexity' problem by our discovery that a mixture of large pools of separately cloned genes containing only one or two target genes of interest (here the genes encoding the VH and VL chains of the identified mAb) can be co-transfected into a single cell, and the desired gene product can then be identified. The only limitation is the requirement for an assay that is sensitive enough to identify this product. Transfecting a single cell with multiple expression vectors was the basis of an expression cloning method that was developed over twenty ago (50,51) and we adapted it for use in our algorithm.

Preparation of Mini-libraries of Genes for the VH Chain and VL Chain cDNAs

To determine whether the specificity of $B_{Mem}$ is reflected accurately by the analysis of culture supernatants, we needed to isolate mAbs from the selected cultures producing the identified anti-Env mAbs. Our initial attempts using a modified EBV transformation method (26) were unsuccessful in isolating stable cell lines secreting the identified Env-specific mAbs, despite several attempts. For this reason, we developed an entirely new algorithm that includes creating 'mini-libraries' of VH and VL chain (Vκ/λ) genes prepared directly from the $B_{Mem}$ cultures in the selected well, and using genes in the mini-library to identify the specific VH and VL chain (Vκ/λ) genes that encode the specific anti-Env mAb made by $B_{Mem}$ cultures in the selected well. Although more than one of the $B_{Mem}$ cultures may make the desired anti-Env mAb, one selects only one positive mAb-producing well for the next step. Other mAb-producing wells can be similarly processed to make their respective mAb. Keep in mind that there are many possible mAbs against a single Env protein given that the protein has many epitopes. In certain embodiments a person of skill in the art may identify several different mAb-producing wells and want to test the different mAbs for affinity for the target antigen or cross-reactivity or other property to determine whether one of the mAbs may have greater potential significance in either clinical or research use before proceeding.

Cells from the selected anti-Env-producing mAb-positive wells were then harvested without passage in tissue culture and total RNA was isolated using RNAEasy™ miniprep kit (QIAGEN, Valencia, Calif.). Any method known in the art to isolate total RNA can be used. We then selectively amplified the human VH and the variable light (VL) chain genes (either the Vκ or Vλ set of genes, but not both) by reverse transcriptase-PCR to make the respective cDNA molecules. The choice of Vk or Vl is determined by the light chain isotype of the original antibody in the culture. This is determined by using either κ or λ chain specific detector antibodies via ELISA. The VH and Vκ or Vλ cDNAs were then cloned into IgG1 and κ or λ eukaryotic expression vectors with modifications of a previously published method (39); any eukaryotic expression vector can be used so long as it includes promoter and secretion sequences that allow the protein to be secreted by a mammalian or insect cell line.

Individual VH or Vκ/Vλ 'mini-libraries' were prepared for the selected positive well by pooling all of the VH plasmid clones to make a VH mini-library. All of the Vκ or Vλ plasmid clones were pooled to make a separate Vκ or Vλ mini-library. The VH and either the Vκ or Vλ mini-libraries were then mixed and used to transfect 293T cells. Thus, the cells were co-transfected with all of the individual VH chain and VL chain cDNA expression vectors at the same time. We used a Lipofectamine 2000 kit (Invitrogen Carlsbad, Calif.), but any method known in the art can be used. A person of skill in the art will recognize that other host cells can be used including Chinese Hamster Ovary cells, baculovirus, insect cells, and any viral system capable of expressing secreted mammalian proteins in permissive cell lines.

The transfected cells were then cloned and grown under conditions and for a duration of time (about 2-3 days) that enabled the cells to produce antibodies. The culture supernatants were then analyzed by ELISA to identify clones that expressed Env-specific Abs. Any method known in the art can be used to identify the appropriate antibody expression. Co-transfection of the mini-libraries verified that at last one anti-Env VH-Vκ/λ pair was present in the mixture. Modeling studies using cloned VH and Vκ/Vλ genes from existing CD4i and CD4bs mAbs showed that this step could detect the correct VH and Vκ/λ pair if it was present in the mix at a frequency of 1% or greater, which is in a workable range when the mini-libraries are made from cultures of 50 to 100 total memory B cells per well. The wells expressing functional anti-Ebv Abs were identified by screening with the recombinant antigen/antigens of interest. If there are no antibody-producing wells then the process stops (and is repeated with a new group of memory B cells). Once it is established that the mini-libraries contain at least one copy of the desired VH and VL genes (as is evidenced by the production of an antibody of interest), the next step is to identify the correct VH gene.

The correct VH gene was identified by co-transfecting an individual VH gene (cDNA) with either the entire Vκ or the entire Vλ mini-library of cDNAs into 293T cells. FIG. 4. Our results have shown that typically, screening only about 12 to 25 individual VH clones is sufficient to identify at least one VH cDNA that encodes a functional anti-Env Ab. The transformed cells are then grown in individual wells under conditions and for a duration of time that permit antibody expression, and the culture supernatants are screened (for example by ELISA) for production of functional antibody against the antigen of interest. A positive clone indicates that a correct VH gene has been found.

The next step is identifying the correct VL cDNA, which is accomplished as shown in FIG. 5 by co-transfecting individual Vκ or Vλ genes with the VH gene that was identified in the previous step, and again screening culture supernatants for functional anti-Env antibody. As was observed for the VH gene, screening out 12 to 25 individual VL clones is sufficient to identify at least one that encodes a functional anti-Env Ab.

To make a clone that produces fully human mAb, we transiently transfected 293T cells with the indentified VH and Vκ/λ pair. After being grown under conditions and for a duration of time that permitted the transfected cells to make antibody, mAb was purified from the supernatant using Protein-A affinity chromatography. The antibody can be purified by any other method conventionally employed to purify immunoglobulins such as size exclusion chromatogarpy, ion-exchange chromatography, or high salt fractionation.

These steps can be summarized as:

6. using the isolated total RNA of step 5, make cDNA for each VH chain and each VL chain encoded by the total RNA,
7. cloning each VH chain and VL chain cDNA into a separate eukaryotic expression vector,
8. selecting all of the expression vectors comprising the VH chain cDNA to make a VH chain mini-library and selecting all of the expression vectors comprising the VL chain cDNA to make a VL chain mini-library,
9. co-transfecting an appropriate host cell with a mixture comprising each of the VH chain cDNA expression vectors in the VH chain mini-library and with a mixture comprising each of the VL chain cDNA expression vectors in the VL chain mini-library, and growing the co-transfected cells under conditions and for a sufficient time to permit the cells to stably produce antibodies,
10. determining that the co-transfected cells produce the monoclonal antibodies,
11. identifying the VH chain cDNA that produced the monoclonal antibody in step 10, using the steps of
   a. co-transfecting host cells with a particular VH chain cDNA expression vector obtained from the VH chain cDNA mini-library and with a mixture comprising one of each of the cDNA expression vectors from the VL chain mini-library, and growing the co-transfected cells under conditions and for a sufficient time to permit the co-transfected cells to form a clone that stably produces antibodies,
   b. determining whether the clone produces the monoclonal antibodies,
   c. if the co-transfected cells produce the monoclonal antibodies, then proceed to step 11d, and if the co-transfected cells do not produce the monoclonal antibodies, then repeating step 11a and 11b using a different particular VH chain cDNA expression vector until a particular VH chain cDNA expression vector is identified that produces the monoclonal antibodies,
   d. identifying the VH chain cDNA that produced the monoclonal antibodies, and selecting the VH chain cDNA expression vector that was used to make the monoclonal antibody-producing clone,
12. identifying the VL chain cDNA that produced the monoclonal antibodies in step 11, using the steps of
   a. co-transfecting host cells with the VH chain cDNA expression vector identified in step 11d and with a particular VL chain cDNA expression vector selected from the VL chain mini-library, and growing the co-transfected cells under conditions and for a sufficient time to permit the co-transfected cells to form a clone that stably produces antibodies,
   b. determining whether the clone produces the monoclonal antibodies,
   c. if the clone produces the monoclonal antibodies then proceeding to step 12d, and if the co-transfected cells do not produce the monoclonal antibodies, then repeating step 12a and b with a different particular VL chain cDNA expression vector until a particular VL chain cDNA expression vector is identified that produces the monoclonal antibodies,
   d. identifying the VL chain cDNA that produced the monoclonal antibodies, and selecting the VL chain cDNA expression vector that was used to make the monoclonal antibody-producing clone, and
13. co-transfecting a host cell with the identified VH chain cDNA expression vector of step 11d and the identified VL chain cDNA expression vector of step 12d to make a host cell that produces the monoclonal antibodies that specifically bind to the particular known antigen.

Once the desired VH-VL gene pair has been identified, mAb can be made in the amount needed based on the specific goal of the project. To produce laboratory scale quantities (1 to 20 mg), we simply transfected 293T cells with the cDNA expression vectors encoding the correct VH and VL genes of the desired mAb using standard 75 cm$^2$ or 150 cm$^2$ tissue culture flasks. We then isolated the IgG from culture supernatants by protein-A chromatography after several days of culture. Once cloned, the VH and VL genes can be expressed in any of the standard industrial systems such as CHO cells or baculovirus to produce larger quantities of the desired fully human mAb. A person of skill in the art will know how to identify the appropriate host cell.

Other embodiments are directed to a method for determining if an animal has been exposed to or is infected with a known antigen when the animal is not presently making antibodies that specifically bind to the known antigen.

Algorithm Alternatives and Automation

The skilled artisan will understand how to automate or otherwise streamline the methods described herein. One modification that saves time is to carry out steps 2.2 and 2.3 simultaneously by replacing the 'known' VH gene in step 2.3 with the VH mini-library. This results in the contemporaneous identification of the correct VH and VL genes, which is confirmed by the subsequent transfection to produce the antibody. Additional steps during the process can be automated; for example, a centrifuge that enables the preparation of several hundred plasmid mini-preps a day can be used in the methods described herein. Similarly, parallel liquid handling methods can be readily adapted to setting up and harvesting the B$_{Mem}$ cultures, carrying out the RNA isolations, and cloning the VH and VL genes. Transfections in 96 well trays, described herein, can be adapted to liquid handling automation.

The experiments described herein employ 96 well trays for $B_{Mem}$ activation and supernatant production. By the $B_{Mem}$ at the same density of 100 cells per 200 ul volume but using trays that have 384 or 1536 wells, it should be possible to find cultures that have a single Env-specific $B_{Mem}$ and very few other BMem (especially with the 1536 well tray). Due to the increased screening by ELISA the latter tray requires a liquid handling device to reduce variation among cultures and assays, but these methods have been worked out already for the human genome project and should be readily adaptable. The major advantage of using the 1536 well tray is that the complexity of the mini-libraries would be simplified to the point that this step could be eliminated.

The monoclonal antibodies that we have produced as described herein are "recombinant" antibodies that are expressed using a recombinant expression vector transfected into a host cell. The new recombinant mAbs and fragments or variants thereof described and claimed herein are produced by host cells transformed with cDNA encoding appropriate immunoglobulin light and heavy chains. These recombinant antibodies may be produced by any known genetic engineering techniques. In one preferred embodiment the cDNA encoding the immunoglobulin light and heavy chains of the desired antibody are operatively linked to their own transcriptional and translational expression control sequences. The expression vector and expression control sequences are chosen to be compatible with the expression host cell used. In some embodiments, both genes are inserted into the same expression vector. The memory B cells can be isolated from any antibody-producing animal. Eukaryotic host cells such as 293T cells used in the Examples, but other host cells such as Chinese hamster ovary (CHO cells), insect cells, or any viral system capable of expressing secreted eukaryotic proteins in permissive cell lines. CHO cells are the most commonly used mammalian hosts for industrial production of recombinant protein therapeutics. Since the onset of gene technology, a plethora of bacterial microorganisms, fungi and mammalian cells have been developed for the production of foreign proteins. Common organic 'platforms' or host cells that can be transfected with an expression vector carrying the gene for a protein of interest include the bacterium E. coli, and several yeasts and mammalian cells, most of them derived from Chinese hamster cells.

Expression in eukaryotic host cells is preferred for making fully human mAb because such cells are more likely than prokaryotic cells to assemble and secrete a properly folded and immunologically active antibody. However, any antibody produced that is inactive due to improper folding (for example, an antibody produced in prokaryotic cells) may be renaturable according to well-known methods (Kim and Baldwin, "Specific Intermediates in the Folding Reactions of Small Proteins and the Mechanism of Protein Folding", Ann. Rev. Biochem. 51, pp. 459 89 (1982)). In addition, host cells can be used to produce portions of intact antibodies, such as light chain dimers or heavy chain dimers, which also are antibody homologs according to the present invention.

It will be understood that variations on the above procedure can be used in the present invention. Recombinant DNA technology can be used to remove some or all of the DNA encoding either or both of the light and heavy chains that is not necessary for binding to the targeted protein, e.g., the constant region may be modified by, for example, deleting specific amino acids. The molecules expressed from such truncated DNA molecules, which are also referred to herein as "antibody fragments." In addition, bifunctional antibodies may be produced in which one heavy and one light chain are directed against a first antigen, and the other heavy and light chain specifically bind to a different second antigen, or another epitope of on the first antigen.

With the new methods, it is no longer necessary to make chimeric antibodies, such as mouse/human chimeras, for therapeutic use in humans, which are very expensive to make and can elicit an unwanted immune response. However, should there be a use for them, chimeric immunoglobulin chains can be produced using the VH or VL cDNA described herein using recombinant DNA techniques known in the art.

It has recently been shown that antibodies against co-receptor have been useful in treating HIV. J Infect Dis. 2008 Mar. 1; 197(5):721-7. Links Safety, pharmacokinetics, and antiviral activity of HGS004, a novel fully human IgG4 monoclonal antibody against CCR5, in HIV-1-infected patients; and Lalezari J, Yadavalli G K, Para M, Richmond G, Dejesus E, Brown S J, Cai W, Chen C, Zhong J, Novello L A, Lederman M M, Subramanian G M, incorporated herein by reference. Certain embodiments of the invention are directed to making fully human monoclonal antibodies against this co-receptor antigen target for therapeutic use in treating HIV or AIDS.

Additional Uses of the Method

The algorithm can be extended readily to isolate mAbs that specifically bind to any antigen to which an animal has mounted a $B_{Mem}$ response in the frequency of 1 precursor per thousand total $B_{Mem}$. Any antigenic molecule, organic or inorganic, that can elicit an immune response, or that can be modified or derivatized to be antigenic, can be used to make the monoclonal antibodies. This is readily in the range of most immune responses to vaccines or pathogens (52, 38). The method will not work for other species such as non-human primates such as rhesus macaques.

It is known that immunization of rhesus macaques with immunogens derived from humans results in antibody responses that would be deleted in humans because they are 'anti-self'. On the other hand, rhesus macaques and humans use similar VH and VL genes enabling the grafting of antibody specificities from rhesus macaques to human immunoglobulins via molecular genetics. For example, a rhesus macaque can be immunized with a cellular protein from humans that is a potential target for a therapeutic mAb. Because these proteins are 'self' in humans, it would be difficult to raise autoantibodies against this protein in people. By contrast, rhesus macaques should make such antibody responses and rhesus macaque mAbs that specifically bind to the desired immunogen could be isolated using our method. The mAb could be readily humanized by simply grafting the rhesus VH and VL genes onto coding sequences for the desired IgG isotype.

Antibodies and Antibody-Based Assays

"Antibody" or "antibodies" include intact molecules as well as fragments and variants thereof that are capable of specifically binding to an epitope of a protein of interest, including the exemplified monoclonal antibodies that specifically bind to HIV Env proteins. The monoclonal antibodies described herein can be used therapeutically and diagnostically. For example the monoclonal anti-Env antibodies can be used to treat HIV or AIDS. As used herein, "specific binding" refers to the property of the antibody, to: (1) to bind to the protein of interest, e.g., HIV Env proteins, with an affinity of at least about $1 \times 10^7$ $M^{-1}$, and (2) preferentially bind to the protein, with an affinity that is at least two-fold, 50-fold, 100-fold, 1000-fold, or more greater than its affinity for binding to a non-specific antigen (e.g., BSA, casein) other than the protein of interest. In a preferred embodiment, the interaction, e.g., binding, between an antibody and the protein of interest occurs with high affinity (e.g., affinity constant of at least $10^7$ $M^{-1}$, preferably, between $10^8 M^{-1}$ and $10^{10} M^{-1}$, e.g., about $109 M^{-1}$) and specificity. As used herein, a "therapeutically or prophylactically effective amount" of the antibody refers to an amount that is effective, upon single-or multiple-dose administration to the subject, in preventing, reducing or delaying the occurrence of the onset or recurrence of any of the described diseases, or reducing a related symptom.

An antibody is considered to selectively or specifically bind to a protein of interest, even if it also binds to other proteins that are not substantially homologous with the protein of interest. This happens when these other proteins share homology with a fragment or domain of the protein of interest. This conservation in specific regions gives rise to antibodies that bind to both proteins by virtue of the homologous sequence. In this case, it would be understood that antibody binding to the protein of interest is still selective.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids.

The terms "antibody" and "antibodies" include polyclonal antibodies, monoclonal antibodies, humanized or chimeric antibodies, single chain Fv antibody fragments, Fab fragments, and F(ab)$_2$ fragments and any other fragment or variant thereof. Polyclonal antibodies are heterogeneous populations of antibody molecules that specifically bind to a particular antigen, while monoclonal antibodies are homogeneous populations of antibodies to a particular epitope contained within an antigen. Monoclonal antibodies are the focus of the embodiments of the present invention.

Antibody fragments that have specific binding affinity for the a particular protein or polypeptide of interest can be generated by known techniques. Such antibody fragments include, but are not limited to, F(ab')$_2$ fragments that can be produced by pepsin digestion of an antibody molecule, and Fab fragments that can be generated by deducing the disulfide bridges of F(ab')$_2$ fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA), described below. See, Short Protocols in Molecular Biology eds. Ausubel et al., Green Publishing Associates and John Wiley & Sons (1992). Suitable antibodies typically have equal binding affinities for recombinant and native proteins.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

The term "recombinant" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. The described and claimed anti-Env protein monoclonal antibodies identified herein are recombinant antibodies that are expressed using a recombinant expression vector transfected into a host cell. The methods discovered, described and claimed herein can be used to make fully human mAbs naturally, without chemical synthesis. Moreover, the host cell that is transfected with the human VH and VL cDNA is preferably selected to be a cell type that will permit the appropriate posttranslational modification.

The immunoassays, immunohistochemistry, RIA, IRMAs that can be used in the methods of the present invention, are based on the generation of various antibodies, or their variants or fragments.

The amount of an antigen in a biological sample may be determined by a radioimmunoassay, an immunoradiometric assay, and/or an enzyme immunoassay. "Radioimmunoassay" is a technique for detecting and measuring the concentration of an antigen using a labeled (i.e. radioactively labeled) form of the antigen. Examples of radioactive labels for antigens include H3, C14, and I125. The concentration of antigen (i.e. the targeted protein, e.g. anti-Env proteins) in a sample (i.e. biological sample) is measured by having the antigen in the sample compete with a labeled (i.e. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to the antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoassay" where the antibody is linked (i.e. covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least two antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (i.e. enzyme linked) form of the antibody.

In a "sandwich ELISA", an antibody (i.e. to the particular antigen of interest) is linked to a solid phase (i.e. a microtiter plate) and exposed to the antigen. The solid phase is then washed to remove unbound antigen. A labeled (i.e. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and beta-galactosidase. The enzyme linked antibody reacts with a substrate to generate a colored reaction product that can be assayed for.

Pharmaceutical Compositions

Based on and supported by the data presented above, certain embodiments of the present invention provide methods for treating HIV or AIDS by administering a therapeutically effective amount of one or more of the new recombinant monoclonal antibodies that specifically bind to HIV-anti-Env protein, or fragments or variants thereof. In a preferred embodiment, the monoclonal antibodies specifically bind to the CD4i protein.

The invention encompasses the use of the monoclonal antibodies formulated in pharmaceutical compositions to administer to a subject, or to target cells or tissues in a subject. Uses are both diagnostic and therapeutic. The therapeutic antibodies (also referred to as "active compounds") can be incorporated into pharmaceutical compositions suitable for administration to a subject, e.g., a human. Such compositions typically comprise antibody and a pharmaceutically acceptable carrier. It is understood however, that administration can also be to cells in vitro as well as to in vivo model systems.

Formulations of the present monoclonal antibodies may contain more than one type of antibody and more than one other active compound that treats HIV, as necessary for the particular indication being treated, preferably those with complementary activities that do not adversely affect each other. Such molecules are suitably present in combination in amounts that are effective for the purpose intended.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

A therapeutically effective amount of antibody, (i.e., an effective dosage) is an amount that reduces or eliminates one or more symptoms of the disease being treated or achieves the desired therapeutic result. Another way to determine a therapeutically effective dose of a monoclonal anti Env protein antibody is to determine the amount that decreases the HIV viral load. Where the monoclonal antibodies specifically bind to another pathogen, the therapeutically effective amounts can be an amount that reduces the amount of pathogen in the subject. This amount typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject, however this can vary. Expressed as a daily dose, this amount can be between about 0.1 nanograms per kilogram body weight per day and about 20 milligrams per kilogram body weight per day, or between about 1 nanogram per kilogram body weight per day and about 10 milligrams per kilogram body weight per day. However, the skilled artisan will appreciate that certain factors may influence the dosage required to effectively treat a subject, including but not limited to the severity of the condition, previous treatments, the general health and/or age of the subject, and other disorders or diseases present. Moreover, treatment of a subject with a therapeutically effective amount of the antibody can include a single treatment or, preferably, can include a series of treatments.

It is understood that appropriate doses of the active therapeutic agents depends upon a number of factors within the ken of the ordinarily skilled physician, veterinarian, or researcher. The dose(s) will vary, for example, depending upon the identity, size, and condition of the subject or sample being treated, further depending upon the route by which the composition is to be administered. It is furthermore understood that appropriate doses depend upon the potency of the therapeutic agent with respect to the expression or activity to be modulated. A physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds or therapeutic agents can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamante tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the antibodies and any other active compounds in the required amount in an appropriate solvent with one or a combination of ingredients enumerated above, as required, followed by filtered sterilization.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

The present invention is more particularly described in the following examples, which are intended as illustrative only, since numerous modifications and variations therein will be apparent to those of ordinary skill in the art.

EXAMPLES

Example 1

Subjects and Reagents

Blood was obtained from NVS donors (5) and normal healthy volunteers under approval of the University of Maryland Institutional Review Board. Plasma was collected from blood after centrifugation and was kept at −80° C. Peripheral blood mononuclear cells (PBMC) were isolated by Ficoll-Hypaque® centrifugation and were stored in liquid Nitrogen after resuspension in freezing medium ((90% (v/v) fetal bovine serum, DMSO).

Recombinant gp120$_{Ba-L}$ from the HIV-1$_{Ba-L}$ isolate and a full-length single chain (FLSC) fusion protein of gp120$_{Ba-L}$ and human CD4 D1D2 were produced in the laboratory as described previously (30). An HIV-1$_{Ba-L}$ gp140 oligomer protein (gp140$_{Ba-L}$) with a chimeric N-terminal gp41 of was prepared at Advanced BioScience Laboratories (Kensington, Md.) according to published methods (31). Soluble human CD4-D1D2 fused to the Fc domain of human IgG1 (sCD4-Ig) was isolated from 293T cells stably transfected with a sCD4-Ig construct generally provided by Dr. Brian Seed, Massachusetts General Hospital, Boston, Mass. Soluble human CD4 D1-D4 protein was provided generously by Biogen, Inc., Cambridge, Mass. An IgG chimera of FLSC (FLSC-Ig) was prepared in our laboratory as described (32). An IgG chimera of gp120$_{Ba-L}$ (gp120-Ig) was derived from the FLSC-Ig construct by removal of the CD4-D1D2 coding region and fusing the gp120 region plus the flexible serine-glycine linker of FLSC with the human IgG Fc fragment of the chimera. The resulting gp120-Ig protein was isolated in the laboratory from a stably transfected 293T cell using protein-A Sepharose columns (Sigma-Aldrich) (30). An affinity purified goat Ab (D7324) that specifically bind to the C-terminal peptide of HIV-1 gp120 was purchased from Cliniqa, Los Angeles, Calif. HIV-1 CD4i Monoclonal Abs (mAbs) 17b, 19e, ED47, C11 and A32 were purified by protein A affinity chromatography from hybridoma cells or 293T supernatants prepared by transfecting heavy and light chain genes encoding the Abs. These mAbs were kindly provided by Dr. James Robinson, Tulane University, New Orleans, La. CD4bs mAb m14 (33) was kindly provided by Dr. Dimiter Dimitrov, NCI, Frederick, Md. CD4bs mAb b12 (25) was made from 293T cells transfected with synthesized b12-IgG1 expression vectors. The broadly neutralizing mAb 2G12 was purchased from Polymun Scientific, Vienna, Austria.

Example 2

Enzyme-Linked Immunosorbent Assay (ELISA)

ELISA was performed using a modified protocol (30, 34). All incubations were performed at 37° C. and used a 50 μl per well volume format. Blotto buffer (TBS (10 mM Tris, 100 mM NaCl, pH 8.0) with 10% dry milk and 0.1% NP-40) was used as blocking solution and diluting solution for sample and detecting Abs. TBS-T buffer (TBS with 1% Tween-20) was used as washing solution. Briefly, plates were coated with D7324 (2 μg/ml) in TBS at 4° C. overnight. Recombinant gp120$_{Ba-L}$ (1 μg/ml) or FLSC (1 μg/ml) were captured onto the plates by incubation for 1 hour, and then Ab or supernatant of B cell culture diluted 4 times in blotto was incubated in plate for 1 hour. Bound Abs were then incubated 1 hour with 1:1000 diluted AP-goat anti-human IgG (for detection of mAb) or anti-human λ-chain and/or κ-chain Abs (for detection of total reactive Ab and determination of light chain) (Southern Biotech, Catalog #2040-04) and detected with Blue Phos Microwell Phosphatase Substrate System (KPL 50-88-00). The gp140 ELISA was performed as above except gp140$_{Ba-L}$ was directly coated on plate at 1 μg/ml overnight at 4° C. Similarly, an in house quantitative human total IgG ELISA was set up by coating with un-conjugated goat anti-human λ and anti-human κ Abs (all from Southern Biotech), detecting with AP-goat anti-human IgG.

Competition ELISA was used as described (35) to determine if plasma samples contain CD4i Abs that block CD4i mAbs (17b, ED47) binding to FLSC or CD4bs Abs that block CD4bs mAbs (b12, sCD4-Ig) binding to gp120. Briefly, we captured FLSC or gp120 to 96-well plates as above. After washing, captured Env was incubated with the indicated concentrations of plasma samples premixed with a biotinylated mAb of half-maximum binding concentration for 1 h, and then detected with AP-conjugated Strepavidin (Southern Biotech) as described above. Data were normalized to the percentage of reactivity seen in the presence of normal serum and IC50 titer was calculated.

Example 3

Inhibition of HIV-1 Env Proteins Binding to CD4 or CCR5

The abilities of Abs to block the binding of gp120-Ig to CD4 or FLSC-Ig to CCR5 were determined by flow cytometry using CEM-NK$^r$ cells (for CD4 assays) or C2fTh/CCR5 cells (for CCR5 assays). Briefly, FLSC-Ig or gp120-Ig was labeled with Zenon-APC reagent (Invitrogen, Carlsbad, Calif.) according to manufacturer's instructions and used in preliminary experiments to confirm specific saturable binding of the ligands to their receptors. The abilities of CD4bs or CD4i Abs in plasma to block binding of the ligands was determined by pre-incubating limiting concentrations of APC-tagged gp120-Ig or FLSC-Ig with plasma dilutions prior to incubation with the indicator cells and measurement of bound ligand by flow cytometry using a FACSCalibur flow cytometer (BD Biosciences, San Jose, CA.).

Example 4

Neutralization Assays

We tested plasma samples in neutralization assays of conventional PHA-PBMC format (28, 36) performed by our group and IgG purified from plasma in an Env-pseudotpyed virus format (8, 37) performed by Monogram Biosciences, Inc., South San Francisco, Calif. As an additional measure of CD4i Abs, plasma was tested in the 'CD4-triggered' neutralization assay that utilizes TZM-bl reporter cells and HIV-$2_{7312A/V434M}$ as described (20). This format specifically detects CD4i Abs by markedly enhanced neutralization of the virus in the presence of sub-inhibitory quantities of soluble CD4 (sCD4) (20, 28).

Example 5

Laboratory Protocol for Cloning Antibodies from Human B$_{Mem}$ Cells

Part I: Reverse Transcription-polymerase Chain Reaction (RT-PCR) for Human Monoclonal Antibody (mAb) VH and VK/VL Genes from RNA Samples.

A) Reagents

1. RT-PCR Kit: Invitrogen™ SKU# 12574-035 (SuperScript® III One-Step RT-PCR System with Platnum Taq High Fidelity)
2. RNase Inhibitor: Promega # N26IB, RNasin® Plus (40 U/ul)
3. RNA isolated from cells of B$_{mem}$ culture by RNeasy® Mini Kit (QIAGEN® #74106) or any RNA sample containing mRNA encoding a desired mAb
4. PCR Primers (sequences shown in list below):
    (a) VH primers: 5'VH Mix (5 uM each) and 3'VH Mix (20 uM each)
    (b) VK primers: 5'VK Mix (5 uM each) and 3'VK Mix (20 uM each)
    (c) VL primers: 5'VL Mix (5 uM each) and 3'VL Mix (20 uM each)
    (d) IgG-VH primers (5'VH Mix paired with 3'IgG-VH-NheI)
    (e) IgG-CH primers (5'VH Mix paired with 3'IgG-HCstop)
    (f) IgCK primers (5'VK Mix paired with 3'Ig-CKstop)
    (g) IgCL primers (5'VL Mix paired with 3'Ig-CLstop)
5. QIAEX II® Gel Extraction Kit (V=variable region; C=constant region; H=heavy chain; L=lambda light chain; K=kappa light chain.)

| List of Primer Sequences (restriction sites are underlined) | |
|---|---|
| 5'VH primers | |
| 5Age1 VH1/5/7 | GTGCC<u>ACCGGT</u>GTACATTCCCAGGTSCAGCTGGTGCARTC; (SEQ ID NO: 1) |
| 5Age1 VH1-24 | GTGCC<u>ACCGGT</u>GTACATTCCCAGGTCCAGCTGGTACAGTC; (SEQ ID NO: 2 |
| 5Age1 VH1-3/18 | GTGCC<u>ACCGGT</u>GTACATTCCCAGGTYCAGCTKGTGCAGTC; (SEQ ID NO: 3) |
| 5Age1 VH1-17 | GTGCC<u>ACCGGT</u>GTACATTCCCAGGTTCAGCTGTTGCAGCC; (SEQ ID NO: 4) |
| 5Age1 VH1-45/58 | GTGCC<u>ACCGGT</u>GTACATTCCCARATGCAGCTGGTGCAGTCTG; (SEQ ID NO: 5) |
| 5Age1 VH2 | GTGCC<u>ACCGGT</u>GTACATTCCCAGRTCACCTTGARGGAGTC; (SEQ ID NO: 6) |
| 5Age1 VH3 | GTGCC<u>ACCGGT</u>GTACATTCCGAGGTRCANCTGGTGGAGTC; (SEQ ID NO: 7) |
| 5Age1 VH3-23 | GTGCC<u>ACCGGT</u>GTACATTCCGAGGTGCAGCTGTTGGAGTC; (SEQ ID NO: 8) |
| 5Age1 VH3-32 | GTGCC<u>ACCGGT</u>GTACATTCCGAGGTGGAGCTGATAGAGTC; (SEQ ID NO: 9) |
| 5Age1 VH3-33 | GTGCC<u>ACCGGT</u>GTACATTCCGAGGTACAGCTCGTGGAGTC; (SEQ ID NO: 10) |
| 5Age1 VH4 | GTGCC<u>ACCGGT</u>GTACATTCCCAGSTGCAGCTGCAGGAGTC; (SEQ ID NO: 11) |

-continued

| List of Primer Sequences (restriction sites are underlined) | |
|---|---|
| 5Age1 VH4-34 | GTGCC<u>ACCGGT</u>GTACATTCCCAGGTGCAGCTACARCAGTG;<br>(SEQ ID NO: 12) |
| 5Age1 VH6 | GTGCC<u>ACCGGT</u>GTACATTCCCAGGTACAGCTGCAGCAGTCAG.<br>(SEQ ID NO: 13) |
| 3'VH primers: | |
| 3Sal1 JH1/2/4/5 | TGCGA<u>AGTCGAC</u>GCTGAGGAGACRGTGACCAGG;<br>(SEQ ID NO: 14) |
| 3Sal1 JH3 | TGCGAA<u>GTCGAC</u>GCTGAAGAGACGGTGACCATTGTC;<br>(SEQ ID NO: 15) |
| 3Sal1 JH6 | TGCGAA<u>GTCGAC</u>GCTGAGGAGACGGTGACCGTGG;<br>(SEQ ID NO: 16) |
| 3Sal1-JH3* | TGCGAA<u>GTCGAC</u>GCTAAAGAGACGGTGACCACTGTC.<br>(SEQ ID NO: 17) |
| 5'VK primers: | |
| 5Age1 VK1 | CTCAC<u>ACCGGT</u>GTCCACTGTGMCATCCAGWTGACCCAGTCTC;<br>(SEQ ID NO: 18) |
| 5Age1 VK1-8/D-43 | CTCAC<u>ACCGGT</u>GTCCACTGTGCCATCCGGATGACCCAGTCTC;<br>(SEQ ID NO: 19) |
| 5Age1 VK1D-8 | CTCAC<u>ACCGGT</u>GTCCACTGTGTCATCTGGATGACCCAGTCTC;<br>(SEQ ID NO: 20) |
| 5Age1 VK1-22 | CTCAC<u>ACCGGT</u>GTCCACTGTGACATCCAGATGACTCAGYCTC;<br>(SEQ ID NO: 21) |
| 5Age1 VK2-24 | CTCAC<u>ACCGGT</u>GTCCACTGTGATATTGTGATGACCCAGACTC;<br>(SEQ ID NO: 22) |
| 5Age1 VK2-28/30 | CTCAC<u>ACCGGT</u>GTCCACTGTGATRTTGTGATGACTCAGTCTC;<br>(SEQ ID NO: 23) |
| 5Age1 VK3-7 | CTCAC<u>ACCGGT</u>GTCCACTGTGAAATTGTAATGACACAGTCTC;<br>(SEQ ID NO: 24) |
| 5Age1 VK3-11/20 | CTCAC<u>ACCGGT</u>GTCCACTGTGAAATTGTGTTGACRCAGTCTC;<br>(SEQ ID NO: 25) |
| 5Age1 VK3-15 | CTCAC<u>ACCGGT</u>GTCCACTGTGAAATAGTGATGAYGCAGTCTC;<br>(SEQ ID NO: 26) |
| 5Age1 VK3-34 | CTCACACCGGTGTCCACTGTGAAGTTGTGCTGACATGGTC;<br>(SEQ ID NO: 27) |
| 5Age1 VK4-1 | CTCACACCGGTGTCCACTGTGACATCGTGATGACCCAGTCTC;<br>(SEQ ID NO: 28) |
| 5Age1 VK5-2 | CTCACACCGGTGTCCACTGTGAAACGACACTCACGCAGTCTC;<br>(SEQ ID NO: 29) |
| 5Age1 VK6-21 | CTCACACCGGTGTCCACTGTGAAATTGTGCTGACTCAGTCTC;<br>(SEQ ID NO: 30) |
| 5Age1 VK6D-41 | CTCAC<u>ACCGGT</u>GTCCACTGTGATGTTGTGATGACACAGTCTC;<br>(SEQ ID NO: 31) |
| 5Age1 VK7-3 | CTCAC<u>ACCGGT</u>GTCCACTGTGACATTGTGCTGACCCAGTCTC.<br>(SEQ ID NO: 32) |
| 3'VK primers | |
| 3BsiWI JK1/4 | GCCAC<u>CGTACG</u>TTTGATYTCCACCTTGGTCCC;<br>(SEQ ID NO: 33) |
| 3BsiWI JK2 | GCCAC<u>CGTACG</u>TTTGATCTCCAGCTTGGTCCC;<br>(SEQ ID NO: 34) |

List of Primer Sequences (restriction sites are underlined)

| | |
|---|---|
| 3BsiWI JK3 | GCCAC<u>CGTACG</u>TTTGATATCCACTTTGGTCCC;<br>(SEQ ID NO: 35) |
| 3BsiWI JK5 | GCCAC<u>CGTACG</u>TTTAATCTCCAGTCGTGTCCC.<br>(SEQ ID NO: 36) |

5'VL primers

| | |
|---|---|
| 5Age1 VL1a | GACTC<u>ACCGGT</u>GTCCTCTCCCAGTCTGTGCTGACTCAGCC;<br>(SEQ ID NO: 37) |
| 5Age1 VL1b | GACTC<u>ACCGGT</u>GTCCTCTCCCAGTCTGTGYTGACGCAGCC;<br>(SEQ ID NO: 38) |
| 5Age1 VL1c | GACTC<u>ACCGGT</u>GTCCTCTCCCAGTCTGTCGTGACGCAGCC;<br>(SEQ ID NO: 39) |
| 5Age1 VL2 | GACTC<u>ACCGGT</u>GTCCTCTCCCARTCTGCCCTGACTCAGCC;<br>(SEQ ID NO: 40 |
| 5Age1 VL2-34 | GACTC<u>ACCGGT</u>GTCCTCTCCCAGTCTGTTCTGACTCAGCC;<br>(SEQ ID NO: 41) |
| 5Age1 VL2-5 | GACTC<u>ACCGGT</u>GTCCTCTCCCAGTCTGCCCTGATTCAGCC;<br>(SEQ ID NO: 42 |
| 5Age1 VL3a | GACTC<u>ACCGGT</u>GTCCTCTCCTCCTATGWGCTGACTCAGCC;<br>(SEQ ID NO: 43 |
| 5Age1 VL3b | GACTC<u>ACCGGT</u>GTCCTCTCCTCCTATGAGCTGACACAGCC;<br>(SEQ ID NO: 44) |
| 5Age1 VL3c | GACTC<u>ACCGGT</u>GTCCTCTCCTCTTCTGAGCTGACTCAGGA;<br>(SEQ ID NO: 45) |
| 5Age1 VL3d | GACTC<u>ACCGGT</u>GTCCTCTCCTCCTATGAGCTGATGCAGCC;<br>(SEQ ID NO: 46) |
| 5Age1 VL3e | GACTC<u>ACCGGT</u>GTCCTCTCCTCCTCTGGGCCAACTCAGGT;<br>(SEQ ID NO: 47) |
| 5Age1 VL4 | GACTC<u>ACCGGT</u>GTCCTCTCCCAGCYTGTGCTGACTCAATC;<br>(SEQ ID NO: 48) |
| 5Age1 VL5 | GACTC<u>ACCGGT</u>GTCCTCTCCCAGSCTGTGCTGACTCAGCC;<br>(SEQ ID NO: 49) |
| 5Age1 VL4/9 | GACTC<u>ACCGGT</u>GTCCTCTCCCTGCCTGTGCTGACTCAGCC;<br>(SEQ ID NO: 50) |
| 5Age1 VL6 | GACTC<u>ACCGGT</u>GTCCTCTCCAATTTTATGCTGACTCAGCC;<br>(SEQ ID NO: 51) |
| 5Age1 VL7 | GACTC<u>ACCGGT</u>GTCCTCTCCCAGRCTGTGGTGACTCAGGA;<br>(SEQ ID NO: 52) |
| 5Age1 VL8 | GACTC<u>ACCGGT</u>GTCCTCTCCCAGACTGTGGTGACCCAGGA;<br>(SEQ ID NO: 53) |
| 5Age1 VL10 | GACTC<u>ACCGGT</u>GTCCTCTCCCAGGCAGGGCTGACTCAGCCA;<br>(SEQ ID NO: 54) |
| 5Age1 VL11 | GACTC<u>ACCGGT</u>GTCCTCTCCCGGCCCGTGCTGACTCAGCC.<br>(SEQ ID NO: 55) |

3'VL primers:

| | |
|---|---|
| 3'Xho1-CL | CTCTA<u>CTCGAG</u>GGYGGGAACAGAGTGAC.<br>(SEQ ID NO: 56) |

Alternative 3' primers:

| | |
|---|---|
| 3'IgG-VH-NheI | GGAGGGT<u>GCTAGC</u>GGGAAGACSGATGGGCCCTTG;<br>(SEQ ID NO: 57) |

| List of Primer Sequences (restriction sites are underlined) | |
|---|---|
| 3'Ig-CKstop | GTGTGCGGCCGCTCAACACTCTCCCCTGTTGAAGCTC;<br>(SEQ ID NO: 58) |
| 3'Ig-CLstop1 | GTGTGCGGCCGCTCATGAACATTCTGYAGGGGCCACTGTC;<br>(SEQ ID NO: 59) |
| 3'Ig-CLstop2 | GTGTGCGGCCGCTCATGAACATTCCGTAGGGGCMACTGTC;<br>(SEQ ID NO: 60) |
| 3'IgG-Cstop | GTGTGCGGCCGCTCATTTACCCRGAGACAGGGAGAGGCT;<br>(SEQ ID NO: 61) |
| 3'IgA-Cstop | GTGTGCGGCCGCTCAGTAGCAGGTGCCGTCCACCTCCGCCATG.<br>(SEQ ID NO: 62) |

B) Procedures
1. Set up RT-PCR reaction for VH, VK, or VL chain genes; per reaction (25 ul volume):
    2× reaction mix: 12.5 ul
    1st 5' primer mix: 0.5 ul
    1st 3' primer mix: 0.5 ul
    RNase inhibitor 0.1 ul (or 4 units)
    ddH2O: 6 ul
    enzyme mix: 0.5 ul
    RNA sample: 5 ul
(Can make master mix of the first 6 reagents and aliquot 20 ul for each reaction plus the 5 ul RNA sample.)
2. PCR Conditions:
    1) pre-heat PCR block to 50° C.
    2) 50° C. for 30 min
    3) 94° C. for 2 min
    4) 40 cycles of: 94° C. 15 sec, 55° C. 30 sec, 68° C. 45 sec (2 min for CH, CK, or CL).
    5) 68° C. 5 min
    6) 4° C. hold until End
3. Isolation of VH and VK or VL DNA from RT-PCR
    1) Run 1.2% Argrose Gel
    2) Cut DNA Band (around 400 bp size)
    3) Purify DNA from Gel by QIAEX II® Gel Extraction Kit
    4) Run 1 ul of purified DNA to confirm.
    Part II: Expression Cloning of Human mAb VH and VK/VL Genes.
    A) Reagents
    1. Vector Plasmids (Vector Sequences Shown Below):
    1). p19EH-AS6 for Cloning VH Genes:
pBR322 derived vector with CMV promoter, mouse IgK signal peptide sequence upstream of VH gene of mAb 19e that is linked to human IgG1 heavy chain constant region (CH1 to CH3) and hBGH polyA site. Cloning sites were introduced into signal sequence (AgeI/SgrAI), J-CH1 junction (SalI), CH1 sequence (NheI) and the end of CH3 (NotI/HindIII) to facilitate the cloning of heavy chain genes.
    2). p14B7K-SN1 for Cloning VK Genes:
pBR322 derived vector with CMV promoter, mouse IgK signal peptide sequence upstream of VK gene of mAb 14B7 that is linked to human Ig kappa chain constant region (CK) and hBGH polyA site. Cloning sites were introduced into signal sequence (AgeI/SgrAI), J-CK junction (BsiWI), and the end of CK (NotI/HindIII) to facilitate the cloning of Ig kappa chain genes.
    3). pA32L-SN5 for Cloning VL Genes:
pBR322 derived vector with CMV promoter, mouse IgK signal peptide sequence upstream of VL gene of mAb A32 that is linked to human Ig lambda chain constant region (CL) and hBGH polyA site. Cloning sites were introduced into signal sequence (AgeI/SgrAI), 5' CL (XhoI), and the end of CL (NotI/HindIII) to facilitate the cloning of Ig lambda chain genes.
    Vector Sequences
    1) Vector p19EH-AS6:
VH gene of mAb 19 was inserted into cloning sites of AgeI/SalI to make 19eVH plasmids, then point mutation from A to C at 5'end of AgeI site were generated by PCR to introduce SgrAI site into AgeI site (at the mouse IgK signal sequence). A site of NheI was introduced near the 5'end of CH1 by overlap PCR using primers (5'IgG-CH1-NheI: cttcccgctagcaccctcctccaagagcac (SEQ ID NO: 63) and 3'IgG-CH1-NheI: ggagggtgctagcgggaagacsgatgggcccttg (SEQ ID NO: 64)) site of NotI was introduced to the end of CH3 sequence by PCR using primers 5'IgG-CH1-NheI and 3'IgG-Cstop-NotI (gtggaagcttgcggccgctcatttacccrgagacagggacaggct; SEQ ID NO: 65).

| FEATURES | Location/Qualifiers |
|---|---|
| misc_feature | 36..36<br>/gene="SpeI"<br>/note="SECDrawAs=Marker" |
| CDS | 937..2367<br>/gene="19e-H"<br>/product="19e Ab Heavy Chain"<br>/note="SECDrawAs=Gene" |
| misc_feature | 1383..1669<br>/gene="CH1"<br>/product="IgG1-CH1"<br>/note="SECDrawAs=Region" |

```
misc_feature    1670..1714
                /gene="Hinge"
                /product="IgG1-Hinge"
                /note="SECDrawAs=Region"
misc_feature    1715..2044
                /gene="CH2"
                /product="IgG1-CH2"
                /note="SECDrawAs=Region"
misc_feature    2045..2367
                /gene="CH3"
                /product="IgG1-CH3"
                /note="SECDrawAs=Region"
misc_feature    2382..2520
                /gene="PolyA"
                /product="SV40-PolyA"
                /note="SECDrawAs=Region"
misc_feature    3206..3666
                /gene="f1-origin"
                /product="F1-origin"
                /note="SECDrawAs=Region"
CDS             4046..4906
                /gene="Amp-r"
                /product="beta-lactamase"
                /note="SECDrawAs=Gene"
misc_feature    4951..5758
                /gene="ColE1 Ori"
                /note="SECDrawAs=Region"
promoter        1..675
                /note="hCMV promoter"
```

| BASE COUNT | | | | | |
|---|---|---|---|---|---|
| ORIGIN | - 1485 A | 1642 C | 1499 G | 1449 T | 0 OTHER |

(SEQ ID NO: 66)

```
   1   CGAATTAATT CGAGCTCGCC CGACATTGAT TATTGACTAG TTATTAATAG TAATCAATTA
  61   CGGGGTCATT AGTTCATAGC CCATATATGG AGTTCCGCGT TACATAACTT ACGGTAAATG
 121   GCCCGCCTGG CTGACCGCCC AACGACCCCC GCCCATTGAC GTCAATAATG ACGTATGTTC
 181   CCATAGTAAC GCCAATAGGG ACTTTCCATT GACGTCAATG GGTGGAGTAT TTACGGTAAA
 241   CTGCCCACTT GGCAGTACAT CAAGTGTATC ATATGCCAAG TACGCCCCCT ATTGACGTCA
 301   ATGACGGTAA ATGGCCCGCC TGGCATTATG CCCAGTACAT GACCTTATGG GACTTTCCTA
 361   CTTGGCAGTA CATCTACGTA TTAGTCATCG CTATTACCAT GGTGATGCGG TTTTGGCAGT
 421   ACATCAATGG GCGTGGATAG CGGTTTGACT CACGGGGATT TCCAAGTCTC CACCCCATTG
 481   ACGTCAATGG GAGTTTGTTT TGGCACCAAA ATCAACGGGA CTTTCCAAAA TGTCGTAACA
 541   ACTCCGCCCC ATTGACGCAA ATGGGCGGTA GGCGTGTACG GTGGGAGGTC TATATAAGCA
 601   GAGCTCGTTT AGTGAACCGT CAGATCGCCT GGAGACGCCA TCCACGCTGT TTTGACCTCC
 661   ATAGAAGACA CCGGGACCGA TCCAGCCTCC GCGGCCGGGA ACGGTGCATT GGAACGCGGA
 721   TTCCCCGTGC CAAGAGTGAC GTAAGTACCG CCTATAGAGT CTATAGGCCC ACCCCCTTGG
 781   CTTCGTTAGA ACGCGGCTAC AATTAATACA TAACCTTATG TATCATACAC ATACGATTTA
 841   GGTGACACTA TAGAATAACA TCCACTTTGC CTTTCTCTCC ACAGGTGTCC ACTCCCAGGT
 901   CCAACTGCAC CTCGGTTCTA TCGATTGAAT TCCACCATGG GATGGTCATG TATCATCCTT
 961   TTTCTAGTAG CAACTGCCAC CGGTGTACAT TCCCAGGTGC AGCTGGTGCA GTCTGGGCCT
1021   GACATGAAGA AGCCTGGGGC CTCAGTGAAG GTCTCCTGCA AGGTTTCCGG ATACACCCTC
1081   ACTGAAGTAA CCATGCACTG GGTGCGACAG GCTCCTGGAA AAGGGCTTGA GTGGATGGGA
1141   GGTTTTGATC TTGAAGATGG TGAAACAATC TACGCACAGA AGTTCCAGGG CAGAGTCACC
1201   ATGACCGAGG ACACATCCAC AGACACAGCC TACATGGAGC TCAGCAGCCT GAGATCTGAG
1261   GACACGGCCG TGTATTACTG TGCAACAAAA CCCCTACGAA ATTTTGACTG GTCCCGGCGG
1321   GGTGACTACG GTATGGACGT CTGGGGCCAA GGGACAATGG TCACCGTCTC TTCAGCGTCG
```

```
1381  ACCAAGGGCC CATCGGTCTT CCCGCTAGCA CCCTCCTCCA AGAGCACCTC TGGGGGCACA
1441  GCGGCCCTGG GCTGCCTGGT CAAGGACTAC TTCCCCGAAC CTGTGACGGT CTCGTGGAAC
1501  TCAGGCGCCC TGACCAGCGG CGTGCACACC TTCCCGGCTG TCCTACAGTC CTCAGGACTC
1561  TACTCCCTCA GCAGCGTGGT GACCGTGCCC TCCAGCAGCT TGGGCACCCA GACCTACATC
1621  TGCAACGTGA ATCACAAGCC CAGCAACACC AAGGTGGACA AGAGAGTTGA GCCCAAATCT
1681  TGTGACAAAA CTCACACATG CCCACCGTGC CCAGCACCTG AACTCCTGGG GGGACCGTCA
1741  GTCTTCCTCT TCCCCCCAAA ACCCAAGGAC ACCCTCATGA TCTCCCGGAC CCCTGAGGTC
1801  ACATGCGTGG TGGTGGACGT GAGCCACGAA GACCCTGAGG TCAAGTTCAA CTGGTACGTG
1861  GACGGCGTGG AGGTGCATAA TGCCAAGACA AAGCCGCGGG AGGAGCAGTA CAACAGCACG
1921  TACCGTGTGG TCAGCGTCCT CACCGTCCTG CACCAGGACT GGCTGAATGG CAAGGAGTAC
1981  AAGTGCAAGG TCTCCAACAA AGCCCTCCCA GCCCCCATCG AGAAAACCAT CTCCAAAGCC
2041  AAAGGGCAGC CCCGAGAACC ACAGGTGTAC ACCCTGCCCC CATCCCGGGA GGAGATGACC
2101  AAGAACCAGG TCAGCCTGAC CTGCCTGGTC AAAGGCTTCT ATCCCAGCGA CATCGCCGTG
2161  GAGTGGGAGA GCAATGGGCA GCCGGAGAAC AACTACAAGA CCACGCCTCC CGTGCTGGAC
2221  TCCGACGGCT CCTTCTTCCT CTATAGCAAG CTCACCGTGG ACAAGAGCAG GTGGCAGCAG
2281  GGGAACGTCT TCTCATGCTC CGTGATGCAT GAGGCTCTGC ACAACCACTA CACGCAGAAG
2341  AGCCTCTCCC TGTCCCCGGG TAAATGAGCG GCCGCAAGCT TGGCCGCCAT GGCCCAACTT
2401  GTTTATTGCA GCTTATAATG GTTACAAATA AAGCAATAGC ATCACAAATT TCACAAATAA
2461  AGCATTTTTT TCACTGCATT CTAGTTGTGG TTTGTCCAAA CTCATCAATG TATCTTATCA
2521  TGTCTGGATC GGGAATTAAT TCGGCGCAGC ACCATGGCCT GAAATAACCT CTGAAAGAGG
2581  AACTTGGTTA GGTACCTTCT GAGGCGGAAA GAACCATCTG TGGAATGTGT GTCAGTTAGG
2641  GTGTGGAAAG TCCCCAGGCT CCCCAGCAGG CAGAAGTATG CAAAGCATGC ATCTCAATTA
2701  GTCAGCAACC AGGTGTGGAA AGTCCCCAGG CTCCCCAGCA GGCAGAAGTA TGCAAAGCAT
2761  GCATCTCAAT TAGTCAGCAA CCATAGTCCC GCCCCTAACT CCGCCCATCC CGCCCCTAAC
2821  TCCGCCCAGT TCCGCCCATT CTCCGCCCCA TGGCTGACTA ATTTTTTTTA TTTATGCAGA
2881  GGCCGAGGCC GCCTCGGCCT CTGAGCTATT CCAGAAGTAG TGAGGAGGCT TTTTTGGAGG
2941  CCTAGGCTTT TGCAAAAAGC TGTTAACAGC TTGGCACTGG CCGTCGTTTT ACAACGTCGT
3001  GACTGGGAAA ACCCTGGCGT TACCCAACTT AATCGCCTTG CAGCACATCC CCCTTTCGCC
3061  AGTTGGCGTA ATAGCGAAGA GGCCCGCACC GATCGCCCTT CCCAACAGTT GCGCAGCCTG
3121  AATGGCGAAT GGCGCCTGAT GCGGTATTTT CTCCTTACGC ATCTGTGCGG TATTTCACAC
3181  CGCATACGTC AAAGCAACCA TAGTACGCGC CCTGTAGCGG CGCATTAAGC GCGGCGGGTG
3241  TGGTGGTTAC GCGCAGCGTG ACCGCTACAC TTGCCAGCGC CCTAGCGCCC GCTCCTTTCG
3301  CTTTCTTCCC TTCCTTTCTC GCCACGTTCG CCGGCTTTCC CCGTCAAGCT CTAAATCGGG
3361  GGCTCCCTTT AGGGTTCCGA TTTAGTGCTT TACGGCACCT CGACCCCAAA AAACTTGATT
3421  TGGGTGATGG TTCACGTAGT GGGCCATCGC CCTGATAGAC GGTTTTTCGC CCTTTGACGT
3481  TGGAGTCCAC GTTCTTTAAT AGTGGACTCT TGTTCCAAAC TGGAACAACA CTCAACCCTA
3541  TCTCGGGCTA TTCTTTTGAT TTATAAGGGA TTTTGCCGAT TTCGGCCTAT TGGTTAAAAA
3601  ATGAGCTGAT TTAACAAAAA TTTAACGCGA ATTTTAACAA AATATTAACG TTTACAATTT
3661  TATGGTGCAC TCTCAGTACA ATCTGCTCTG ATGCCGCATA GTTAAGCCAG CCCCGACACC
```

```
3721  CGCCAACACC CGCTGACGCG CCCTGACGGG CTTGTCTGCT CCGGCATCCG CTTACAGACA
3781  AGCTGTGACC GTCTCCGGGA GCTGCATGTG TCAGAGGTTT CACCGTCAT CACCGAAACG
3841  CGCGAGACGA AAGGGCCTCG TGATACGCCT ATTTTTATAG GTTAATGTCA TGATAATAAT
3901  GGTTTCTTAG ACGTCAGGTG GCACTTTTCG GGGAAATGTG CGCGGAACCC CTATTTGTTT
3961  ATTTTTCTAA ATACATTCAA ATATGTATCC GCTCATGAGA CAATAACCCT GATAAATGCT
4021  TCAATAATAT TGAAAAAGGA AGAGTATGAG TATTCAACAT TTCCGTGTCG CCCTTATTCC
4081  CTTTTTTGCG GCATTTTGCC TTCCTGTTTT TGCTCACCCA GAAACGCTGG TGAAAGTAAA
4141  AGATGCTGAA GATCAGTTGG GTGCACGAGT GGGTTACATC GAACTGGATC TCAACAGCGG
4201  TAAGATCCTT GAGAGTTTTC GCCCCGAAGA ACGTTTTCCA ATGATGAGCA CTTTTAAAGT
4261  TCTGCTATGT GGCGCGGTAT TATCCCGTAT TGACGCCGGG CAAGAGCAAC TCGGTCGCCG
4321  CATACACTAT TCTCAGAATG ACTTGGTTGA GTACTCACCA GTCACAGAAA AGCATCTTAC
4381  GGATGGCATG ACAGTAAGAG AATTATGCAG TGCTGCCATA ACCATGAGTG ATAACACTGC
4441  GGCCAACTTA CTTCTGACAA CGATCGGAGG ACCGAAGGAG CTAACCGCTT TTTTGCACAA
4501  CATGGGGGAT CATGTAACTC GCCTTGATCG TTGGGAACCG GAGCTGAATG AAGCCATACC
4561  AAACGACGAG CGTGACACCA CGATGCCTGT AGCAATGGCA ACAACGTTGC GCAAACTATT
4621  AACTGGCGAA CTACTTACTC TAGCTTCCCG GCAACAATTA ATAGACTGGA TGGAGGCGGA
4681  TAAAGTTGCA GGACCACTTC TGCGCTCGGC CCTTCCGGCT GGCTGGTTTA TTGCTGATAA
4741  ATCTGGAGCC GGTGAGCGTG GGTCTCGCGG TATCATTGCA GCACTGGGGC CAGATGGTAA
4801  GCCCTCCCGT ATCGTAGTTA TCTACACGAC GGGGAGTCAG GCAACTATGG ATGAACGAAA
4861  TAGACAGATC GCTGAGATAG GTGCCTCACT GATTAAGCAT TGGTAACTGT CAGACCAAGT
4921  TTACTCATAT ATACTTTAGA TTGATTTAAA ACTTCATTTT TAATTTAAAA GGATCTAGGT
4981  GAAGATCCTT TTTGATAATC TCATGACCAA AATCCCTTAA CGTGAGTTTT CGTTCCACTG
5041  AGCGTCAGAC CCCGTAGAAA AGATCAAAGG ATCTTCTTGA GATCCTTTTT TTCTGCGCGT
5101  AATCTGCTGC TTGCAAACAA AAAAACCACC GCTACCAGCG GTGGTTTGTT TGCCGGATCA
5161  AGAGCTACCA ACTCTTTTTC CGAAGGTAAC TGGCTTCAGC AGAGCGCAGA TACCAAATAC
5221  TGTTCTTCTA GTGTAGCCGT AGTTAGGCCA CCACTTCAAG AACTCTGTAG CACCGCCTAC
5281  ATACCTCGCT CTGCTAATCC TGTTACCAGT GGCTGCTGCC AGTGGCGATA AGTCGTGTCT
5341  TACCGGGTTG GACTCAAGAC GATAGTTACC GGATAAGGCG CAGCGGTCGG GCTGAACGGG
5401  GGGTTCGTGC ACACAGCCCA GCTTGGAGCG AACGACCTAC ACCGAACTGA GATACCTACA
5461  GCGTGAGCTA TGAGAAAGCG CCACGCCTTC CCGAAGGGAG AAAGGCGGAC AGGTATCCGG
5521  TAAGCGGCAG GGTCGGAACA GGAGAGCGCA CGAGGGAGCT TCCAGGGGGA AACGCCTGGT
5581  ATCTTTATAG TCCTGTCGGG TTTCGCCACC TCTGACTTGA GCGTCGATTT TTGTGATGCT
5641  CGTCAGGGGG GCGGAGCCTA TGGAAAAACG CCAGCAACGC GGCCTTTTTA CGGTTCCTGG
5701  CCTTTTGCTG GCCTTTTGCT CACATGTTCT TTCCTGCGTT ATCCCCTGAT TCTGTGGATA
5761  ACCGTATTAC CGCCTTTGAG TGAGCTGATA CCGCTCGCCG CAGCCGAACG ACCGAGCGCA
5821  GCGAGTCAGT GAGCGAGGAA GCGGAAGAGC GCCCAATACG CAAACCGCCT CTCCCCGCGC
5881  GTTGGCCGAT TCATTAATCC AACTGGCACG ACAGGTTTCC CGACTGGAAA GCGGGCAGTG
```

```
5941  AGCGCAACGC AATTAATGTG AGTTAGCTCA CTCATTAGGC ACCCCAGGCT TTACACTTTA
6001  TGCTTCCGGC TCGTATGTTG TGTGGAATTG TGAGCGGATA ACAATTTCAC ACAGGAAACA
6061  GCTATGACAT GATTA.
```

2) Vector p14B7K-SN1:

VK gene of mAb 14B7(N5-I1) was inserted into cloning sites of AgeI/BsiWI to make 14B7VK plasmids, then point mutation from A to C at 5'end of AgeI site were generated by PCR to introduce SgrAI site into AgeI site (at the mouse IgK signal sequence). A site of NotI was introduced to the end of CK sequence by PCR using primers 5'IgK-C(GGADA-TYAAACGTACGGTGGCTGCACCATC; SEQ ID NO: 67) and 3'IgK-NotI (GTGGAAGCTTGCGGCCGCCTAA-CACTCTCCCCTGTTGAAG; SEQ ID NO: 68).

| FEATURES | Location/Qualifiers |
|---|---|
| misc_feature | 36..36<br>/gene="SpeI"<br>/note="SECDrawAs=Marker" |
| CDS | 937..993<br>/note="mouse IgK signal peptide" |
| misc_feature | 1657..1795<br>/gene="PolyA"<br>/product="SV40-PolyA"<br>/note="SECDrawAs=Region" |
| misc_feature | 2481..2941<br>/gene="f1-origin"<br>/product="F1-origin"<br>/note="SECDrawAs=Region" |
| CDS | 3321..4181<br>/gene="Amp-r"<br>/product="beta-lactamase"<br>/note="SECDrawAs=Gene" |
| misc_feature | 4226..5033<br>/gene="ColE1 Ori"<br>/note="SECDrawAs=Region" |
| promoter | 1..675<br>/note="hCMV promoter" |
| frag | 979..1650<br>/note="170 to 841 of p14B7K-SBN-1.txt" |

| BASE COUNT ORIGIN | - | 1320 A | 1391 C | 1292 G | 1347 T | 0 OTHER |
|---|---|---|---|---|---|---|

(SEQ ID NO: 69)
```
   1  CGAATTAATT CGAGCTCGCC CGACATTGAT TATTGACTAG TTATTAATAG TAATCAATTA
  61  CGGGGTCATT AGTTCATAGC CCATATATGG AGTTCCGCGT TACATAACTT ACGGTAAATG
 121  GCCCGCCTGG CTGACCGCCC AACGACCCCC GCCCATTGAC GTCAATAATG ACGTATGTTC
 181  CCATAGTAAC GCCAATAGGG ACTTTCCATT GACGTCAATG GGTGGAGTAT TTACGGTAAA
 241  CTGCCCACTT GGCAGTACAT CAAGTGTATC ATATGCCAAG TACGCCCCCT ATTGACGTCA
 301  ATGACGGTAA ATGGCCCGCC TGGCATTATG CCCAGTACAT GACCTTATGG GACTTTCCTA
 361  CTTGGCAGTA CATCTACGTA TTAGTCATCG CTATTACCAT GGTGATGCGG TTTTGGCAGT
 421  ACATCAATGG GCGTGGATAG CGGTTTGACT CACGGGGATT TCCAAGTCTC CACCCCATTG
 481  ACGTCAATGG GAGTTTGTTT TGGCACCAAA ATCAACGGGA CTTTCCAAAA TGTCGTAACA
 541  ACTCCGCCCC ATTGACGCAA ATGGGCGGTA GGCGTGTACG GTGGGAGGTC TATATAAGCA
 601  GAGCTCGTTT AGTGAACCGT CAGATCGCCT GGAGACGCCA TCCACGCTGT TTTGACCTCC
 661  ATAGAAGACA CCGGGACCGA TCCAGCCTCC GCGGCCGGGA ACGGTGCATT GGAACGCGGA
 721  TTCCCCGTGC CAAGAGTGAC GTAAGTACCG CCTATAGAGT CTATAGGCCC ACCCCCTTGG
 781  CTTCGTTAGA ACGCGGCTAC AATTAATACA TAACCTTATG TATCATACAC ATACGATTTA
 841  GGTGACACTA TAGAATAACA TCCACTTTGC CTTTCTCTCC ACAGGTGTCC ACTCCCAGGT
 901  CCAACTGCAC CTCGGTTCTA TCGATTGAAT TCCACCATGG GATGGTCATG TATCATCCTT
```

```
 961  TTTCTAGTAG CAACTGCCAC CGGTGTACAT TCAGAAATTG TGTTGACGCA GTCTCCAGGC
1021  ACCCTGTCTT TGTCTCCAGG GGAAAGAGCC ACTCTCTCCT GCAGGGCCAG TCAGAGTGTT
1081  GGCAACAACT ACTTAGGCTG GTACCAGCAG AAACCTGGCC AGGCTCCCAG GCTGCTCATC
1141  TTTGGTGCAT CCACCAGGGC CACTGACATC CCAGAGAGGT TTAGTGGCAG TCGGTCTGGG
1201  ACAGACTTCA CTCTCACCAT CAGCAGACTG GAACCTGAAG ATTTTGCGGT TTATTATTGT
1261  CAGCAGTATG CCAATTCACC GATCACCTTC GGCCAAGGGA CACGACTGGA GATTAAACGT
1321  ACGGTGGCTG CACCATCTGT CTTCATCTTC CCGCCATCTG ATGAGCAGTT GAAATCTGGA
1381  ACTGCCTCTG TTGTGTGCCT GCTGAATAAC TTCTATCCCA GAGAGGCCAA AGTACAGTGG
1441  AAGGTGGATA ACGCCCTCCA ATCGGGTAAC TCCCAGGAGA GTGTCACAGA GCAGGACAGC
1501  AAGGACAGCA CCTACAGCCT CAGCAGCACC CTGACGCTGA GCAAAGCAGA CTACGAGAAA
1561  CACAAAGTCT ACGCCTGCGA AGTCACCCAT CAGGGCCTGA GCTCGCCCGT CACAAAGAGC
1621  TTCAACAGGG GAGAGTGTTG AGGCGGCCGC AAGCTTGGCC GCCATGGCCC AACTTGTTTA
1681  TTGCAGCTTA TAATGGTTAC AAATAAAGCA ATAGCATCAC AAATTTCACA AATAAAGCAT
1741  TTTTTTCACT GCATTCTAGT TGTGGTTTGT CCAAACTCAT CAATGTATCT TATCATGTCT
1801  GGATCGGGAA TTAATTCGGC GCAGCACCAT GGCCTGAAAT AACCTCTGAA AGAGGAACTT
1861  GGTTAGGTAC CTTCTGAGGC GGAAAGAACC ATCTGTGGAA TGTGTGTCAG TTAGGGTGTG
1921  GAAAGTCCCC AGGCTCCCCA GCAGGCAGAA GTATGCAAAG CATGCATCTC AATTAGTCAG
1981  CAACCAGGTG TGGAAAGTCC CCAGGCTCCC CAGCAGGCAG AAGTATGCAA AGCATGCATC
2041  TCAATTAGTC AGCAACCATA GTCCCGCCCC TAACTCCGCC CATCCCGCCC CTAACTCCGC
2101  CCAGTTCCGC CCATTCTCCG CCCCATGGCT GACTAATTTT TTTTATTTAT GCAGAGGCCG
2161  AGGCCGCCTC GGCCTCTGAG CTATTCCAGA AGTAGTGAGG AGGCTTTTTT GGAGGCCTAG
2221  GCTTTTGCAA AAAGCTGTTA ACAGCTTGGC ACTGGCCGTC GTTTTACAAC GTCGTGACTG
2281  GGAAAACCCT GGCGTTACCC AACTTAATCG CCTTGCAGCA CATCCCCCTT TCGCCAGTTG
2341  GCGTAATAGC GAAGAGGCCC GCACCGATCG CCCTTCCCAA CAGTTGCGCA GCCTGAATGG
2401  CGAATGGCGC CTGATGCGGT ATTTTCTCCT TACGCATCTG TGCGGTATTT CACACCGCAT
2461  ACGTCAAAGC AACCATAGTA CGCGCCCTGT AGCGGCGCAT TAAGCGCGGC GGGTGTGGTG
2521  GTTACGCGCA GCGTGACCGC TACACTTGCC AGCGCCCTAG CGCCCGCTCC TTTCGCTTTC
2581  TTCCCTTCCT TTCTCGCCAC GTTCGCCGGC TTTCCCCGTC AAGCTCTAAA TCGGGGGCTC
2641  CCTTTAGGGT TCCGATTTAG TGCTTTACGG CACCTCGACC CCAAAAAACT TGATTTGGGT
2701  GATGGTTCAC GTAGTGGGCC ATCGCCCTGA TAGACGGTTT TTCGCCCTTT GACGTTGGAG
2761  TCCACGTTCT TTAATAGTGG ACTCTTGTTC CAAACTGGAA CAACACTCAA CCCTATCTCG
2821  GGCTATTCTT TTGATTTATA AGGGATTTTG CCGATTTCGG CCTATTGGTT AAAAAATGAG
2881  CTGATTTAAC AAAAATTTAA CGCGAATTTT AACAAAATAT TAACGTTTAC AATTTTATGG
2941  TGCACTCTCA GTACAATCTG CTCTGATGCC GCATAGTTAA GCCAGCCCCG ACACCCGCCA
3001  ACACCCGCTG ACGCGCCCTG ACGGGCTTGT CTGCTCCCGG CATCCGCTTAC AGACAAGCTG
3061  TGACCGTCTC CGGGAGCTGC ATGTGTCAGA GGTTTTCACC GTCATCACCG AAACGCGCGA
3121  GACGAAAGGG CCTCGTGATA CGCCTATTTT TATAGGTTAA TGTCATGATA ATAATGGTTT
3181  CTTAGACGTC AGGTGGCACT TTTCGGGGAA ATGTGCGCGG AACCCCTATT TGTTTATTTT
3241  TCTAAATACA TTCAAATATG TATCCGCTCA TGAGACAATA ACCCTGATAA ATGCTTCAAT
```

```
3301  AATATTGAAA AAGGAAGAGT ATGAGTATTC AACATTTCCG TGTCGCCCTT ATTCCCTTTT

3361  TTGCGGCATT TTGCCTTCCT GTTTTTGCTC ACCCAGAAAC GCTGGTGAAA GTAAAAGATG

3421  CTGAAGATCA GTTGGGTGCA CGAGTGGGTT ACATCGAACT GGATCTCAAC AGCGGTAAGA

3481  TCCTTGAGAG TTTTCGCCCC GAAGAACGTT TTCCAATGAT GAGCACTTTT AAAGTTCTGC

3541  TATGTGGCGC GGTATTATCC CGTATTGACG CCGGGCAAGA GCAACTCGGT CGCCGCATAC

3601  ACTATTCTCA GAATGACTTG GTTGAGTACT CACCAGTCAC AGAAAAGCAT CTTACGGATG

3661  GCATGACAGT AAGAGAATTA TGCAGTGCTG CCATAACCAT GAGTGATAAC ACTGCGGCCA

3721  ACTTACTTCT GACAACGATC GGAGGACCGA AGGAGCTAAC CGCTTTTTTG CACAACATGG

3781  GGGATCATGT AACTCGCCTT GATCGTTGGG AACCGGAGCT GAATGAAGCC ATACCAAACG

3841  ACGAGCGTGA CACCACGATG CCTGTAGCAA TGGCAACAAC GTTGCGCAAA CTATTAACTG

3901  GCGAACTACT TACTCTAGCT TCCCGGCAAC AATTAATAGA CTGGATGGAG GCGGATAAAG

3961  TTGCAGGACC ACTTCTGCGC TCGGCCCTTC CGGCTGGCTG GTTTATTGCT GATAAATCTG

4021  GAGCCGGTGA GCGTGGGTCT CGCGGTATCA TTGCAGCACT GGGGCCAGAT GGTAAGCCCT

4081  CCCGTATCGT AGTTATCTAC ACGACGGGGA GTCAGGCAAC TATGGATGAA CGAAATAGAC

4141  AGATCGCTGA GATAGGTGCC TCACTGATTA AGCATTGGTA ACTGTCAGAC CAAGTTTACT

4201  CATATATACT TTAGATTGAT TTAAAACTTC ATTTTTAATT TAAAAGGATC TAGGTGAAGA

4261  TCCTTTTTGA TAATCTCATG ACCAAAATCC CTTAACGTGA GTTTTCGTTC CACTGAGCGT

4321  CAGACCCCGT AGAAAAGATC AAAGGATCTT CTTGAGATCC TTTTTTTCTG CGCGTAATCT

4381  GCTGCTTGCA ACAAAAAAA CCACCGCTAC CAGCGGTGGT TTGTTTGCCG GATCAAGAGC

4441  TACCAACTCT TTTTCCGAAG GTAACTGGCT TCAGCAGAGC GCAGATACCA AATACTGTTC

4501  TTCTAGTGTA GCCGTAGTTA GGCCACCACT TCAAGAACTC TGTAGCACCG CCTACATACC

4561  TCGCTCTGCT AATCCTGTTA CCAGTGGCTG CTGCCAGTGG CGATAAGTCG TGTCTTACCG

4621  GGTTGGACTC AAGACGATAG TTACCGGATA AGGCGCAGCG GTCGGGCTGA ACGGGGGGTT

4681  CGTGCACACA GCCCAGCTTG GAGCGAACGA CCTACACCGA ACTGAGATAC CTACAGCGTG

4741  AGCTATGAGA AAGCGCCACG CCTTCCCGAA GGGAGAAAGG CGGACAGGTA TCCGGTAAGC

4801  GGCAGGGTCG GAACAGGAGA GCGCACGAGG GAGCTTCCAG GGGGAAACGC CTGGTATCTT

4861  TATAGTCCTG TCGGGTTTCG CCACCTCTGA CTTGAGCGTC GATTTTTGTG ATGCTCGTCA

4921  GGGGGGCGGA GCCTATGGAA AAACGCCAGC AACGCGGCCT TTTTACGGTT CCTGGCCTTT

4981  TGCTGGCCTT TTGCTCACAT GTTCTTTCCT GCGTTATCCC CTGATTCTGT GGATAACCGT

5041  ATTACCGCCT TTGAGTGAGC TGATACCGCT CGCCGCAGCC GAACGACCGA GCGCAGCGAG

5101  TCAGTGAGCG AGGAAGCGGA AGAGCGCCCA ATACGCAAAC CGCCTCTCCC CGCGCGTTGG

5161  CCGATTCATT AATCCAACTG GCACGACAGG TTTCCCGACT GGAAAGCGGG CAGTGAGCGC

5221  AACGCAATTA ATGTGAGTTA GCTCACTCATTAGGCACCCC AGGCTTTACA CTTTATGCTT

5281  CCGGCTCGTA TGTTGTGTGG AATTGTGAGCGGATAACAAT TTCACACAGG AAACAGCTAT

5341  GACATGATTA.
```

3) Vector pA32L-SN5:

VL gene of mAb A32 was inserted into cloning sites of AgeI/XhoI to make A32VL plasmids, then point mutation from A to C at 5'end of AgeI site was generated by PCR to introduce SgrAI site into AgeI site (at the mouse IgK signal sequence). A site of NotI was introduced to the end of CL sequence by PCR using primers 5'IgL-CH1 GTCACTCTGT-TCCCRCCCTCGAGTGAGGAGCTTCAAGCC (SEQ ID NO: 70) and 3'IgL-NotI (GTGGAAGCTTGCGGCCGCT-CATGAACATTCTGYAGGGGCCACTGTC; SEQ ID NO: 71).

```
FEATURES       Location/Qualifiers
misc_feature   36..36
               /gene="SpeI"
               /note="SECDrawAs=Marker"
CDS            937..>978
               /note="mouse IgK signal peptide"
misc_feature   1659..1797
               /gene="PolyA"
               /product="SV40-PolyA"
               /note="SECDrawAs=Region"
misc_feature   2483..2943
               /gene="f1-origin"
               /product="F1-origin"
               /note="SECDrawAs=Region"
CDS            3323..4183
               /gene="Amp-r"
               /product="beta-lactamase"
               /note="SECDrawAs=Gene"
misc_feature   4228..5035
               /gene="ColE1 Ori"
               /note="SECDrawAs=Region"
promoter       1..675
               /note="hCMV promoter"
frag           979..1652
               /note="166 to 839 of pA32L-SXN-5.txt"

BASE COUNT
    ORIGIN     -     1306 A     1419 C     1292 G     1335 T     0 OTHER
                                                              (SEQ ID NO: 72)
       1    CGAATTAATT CGAGCTCGCC CGACATTGAT TATTGACTAG TTATTAATAG TAATCAATTA
      61    CGGGGTCATT AGTTCATAGC CCATATATGG AGTTCCGCGT TACATAACTT ACGGTAAATG
     121    GCCCGCCTGG CTGACCGCCC AACGACCCCC GCCCATTGAC GTCAATAATG ACGTATGTTC
     181    CCATAGTAAC GCCAATAGGG ACTTTCCATT GACGTCAATG GGTGGAGTAT TTACGGTAAA
     241    CTGCCCACTT GGCAGTACAT CAAGTGTATC ATATGCCAAG TACGCCCCCT ATTGACGTCA
     301    ATGACGGTAA ATGGCCCGCC TGGCATTATG CCCAGTACAT GACCTTATGG GACTTTCCTA
     361    CTTGGCAGTA CATCTACGTA TTAGTCATCG CTATTACCAT GGTGATGCGG TTTTGGCAGT
     421    ACATCAATGG GCGTGGATAG CGGTTTGACT CACGGGGATT TCCAAGTCTC CACCCCATTG
     481    ACGTCAATGG GAGTTTGTTT TGGCACCAAA ATCAACGGGA CTTTCCAAAA TGTCGTAACA
     541    ACTCCGCCCC ATTGACGCAA ATGGGCGGTA GGCGTGTACG GTGGGAGGTC TATATAAGCA
     601    GAGCTCGTTT AGTGAACCGT CAGATCGCCT GGAGACGCCA TCCACGCTGT TTTGACCTCC
     661    ATAGAAGACA CCGGGACCGA TCCAGCCTCC GCGGCCGGGA ACGGTGCATT GGAACGCGGA
     721    TTCCCCGTGC CAAGAGTGAC GTAAGTACCG CCTATAGAGT CTATAGGCCC ACCCCCTTGG
     781    CTTCGTTAGA ACGCGGCTAC AATTAATACA TAACCTTATG TATCATACAC ATACGATTTA
     841    GGTGACACTA TAGAATAACA TCCACTTTGC CTTTCTCTCC ACAGGTGTCC ACTCCCAGGT
     901    CCAACTGCAC CTCGGTTCTA TCGATTGAAT TCCACCATGG GATGGTCATG TATCATCCTT
     961    TTTCTAGTAG CAACTGCCAC CGGTGTCCTC TCCCAGTCTG TGTTGACGCA GCCTCCCTCC
    1021    GCGTCCGGGT CTCCTGGACA GTCAGTCACC ATCTCCTGCA CTGGAACCAG CAGTGACGTT
    1081    GGTGGTTATA ACTATGTTTC CTGGTACCAA CACCACCCAG GCAAAGCCCC CAAACTCATA
    1141    ATTTCTGAGG TCAATAACCG GCCCTCAGGG GTCCCTGATC GTTTCTCTGG CTCCAAGTCT
    1201    GGCAACACGG CCTCCCTGAC CGTCTCTGGG CTCCAGGCTG AGGATGAGGC TGAATATTAC
```

-continued

| | | | | | |
|---|---|---|---|---|---|
| 1261 | TGCAGCTCAT | ACACAGACAT | CCACAATTTC | GTCTTCGGCG | GAGGGACCAA GCTGACCGTC |
| 1321 | CTAGGTCAGC | CCAAGGCTGC | CCCCTCGGTC | ACTCTGTTCC | CACCCTCGAG TGAGGAGCTT |
| 1381 | CAAGCCAACA | AGGCCACACT | GGTGTGTCTC | ATAAGTGACT | TCTACCCGGG AGCCGTGACA |
| 1441 | GTGGCCTGGA | AGGCAGATAG | CAGCCCCGTC | AAGGCGGGAG | TGGAGACCAC CACACCCTCC |
| 1501 | AAACAAAGCA | ACAACAAGTA | CGCGGCCAGC | AGCTACCTGA | GCCTGACGCC TGAGCAGTGG |
| 1561 | AAGTCCCACA | GAAGCTACAG | CTGCCAGGTC | ACGCATGAAG | GGAGCACCGT GGAGAAGACA |
| 1621 | GTGGCCCCTA | CAGAATGTTC | ATGAGCGGCC | GCAAGCTTGG | CCGCCATGGC CCAACTTGTT |
| 1681 | TATTGCAGCT | TATAATGGTT | ACAAATAAAG | CAATAGCATC | ACAAATTTCA CAAATAAAGC |
| 1741 | ATTTTTTTCA | CTGCATTCTA | GTTGTGGTTT | GTCCAAACTC | ATCAATGTAT CTTATCATGT |
| 1801 | CTGGATCGGG | AATTAATTCG | GCGCAGCACC | ATGGCCTGAA | ATAACCTCTG AAAGAGGAAC |
| 1861 | TTGGTTAGGT | ACCTTCTGAG | GCGGAAAGAA | CCATCTGTGG | AATGTGTGTC AGTTAGGGTG |
| 1921 | TGGAAAGTCC | CCAGGCTCCC | CAGCAGGCAG | AAGTATGCAA | AGCATGCATC TCAATTAGTC |
| 1981 | AGCAACCAGG | TGTGGAAAGT | CCCCAGGCTC | CCCAGCAGGC | AGAAGTATGC AAAGCATGCA |
| 2041 | TCTCAATTAG | TCAGCAACCA | TAGTCCCGCC | CCTAACTCCG | CCCATCCCGC CCCTAACTCC |
| 2101 | GCCCAGTTCC | GCCCATTCTC | CGCCCCATGG | CTGACTAATT | TTTTTTATTT ATGCAGAGGC |
| 2161 | CGAGGCCGCC | TCGGCCTCTG | AGCTATTCCA | GAAGTAGTGA | GGAGGCTTTT TTGGAGGCCT |
| 2221 | AGGCTTTTGC | AAAAAGCTGT | TAACAGCTTG | GCACTGGCCG | TCGTTTTACA ACGTCGTGAC |
| 2281 | TGGGAAAACC | CTGGCGTTAC | CCAACTTAAT | CGCCTTGCAG | CACATCCCCC TTTCGCCAGT |
| 2341 | TGGCGTAATA | GCGAAGAGGC | CCGCACCGAT | CGCCCTTCCC | AACAGTTGCG CAGCCTGAAT |
| 2401 | GGCGAATGGC | GCCTGATGCG | GTATTTTCTC | CTTACGCATC | TGTGCGGTAT TCACACCGC |
| 2461 | ATACGTCAAA | GCAACCATAG | TACGCGCCCT | GTAGCGGCGC | ATTAAGCGCG GCGGGTGTGG |
| 2521 | TGGTTACGCG | CAGCGTGACC | GCTACACTTG | CCAGCGCCCT | AGCGCCCGCT CCTTTCGCTT |
| 2581 | TCTTCCCTTC | CTTTCTCGCC | ACGTTCGCCG | GCTTTCCCCG | TCAAGCTCTA AATCGGGGGC |
| 2641 | TCCCTTTAGG | GTTCCGATTT | AGTGCTTTAC | GGCACCTCGA | CCCCAAAAAA CTTGATTTGG |
| 2701 | GTGATGGTTC | ACGTAGTGGG | CCATCGCCCT | GATAGACGGT | TTTTCGCCCT TTGACGTTGG |
| 2761 | AGTCCACGTT | CTTTAATAGT | GGACTCTTGT | TCCAAACTGG | AACAACACTC AACCCTATCT |
| 2821 | CGGGCTATTC | TTTTGATTTA | TAAGGGATTT | TGCCGATTTC | GGCCTATTGG TTAAAAAATG |
| 2881 | AGCTGATTTA | ACAAAAATTT | AACGCGAATT | TTAACAAAAT | ATTAACGTTT ACAATTTTAT |
| 2941 | GGTGCACTCT | CAGTACAATC | TGCTCTGATG | CCGCATAGTT | AAGCCAGCCC CGACACCCGC |
| 3001 | CAACACCCGC | TGACGCGCCC | TGACGGGCTT | GTCTGCTCCG | GCATCCGCTT ACAGACAAGC |
| 3061 | TGTGACCGTC | TCCGGGAGCT | GCATGTGTCA | GAGGTTTTCA | CCGTCATCAC CGAAACGCGC |
| 3121 | GAGACGAAAG | GCCTCGTGA | TACGCCTATT | TTTATAGGTT | AATGTCATGA TAATAATGGT |
| 3181 | TTCTTAGACG | TCAGGTGGCA | CTTTTCGGGG | AAATGTGCGC | GGAACCCCTA TTTGTTTATT |
| 3241 | TTTCTAAATA | CATTCAAATA | TGTATCCGCT | CATGAGACAA | TAACCCTGAT AAATGCTTCA |
| 3301 | ATAATATTGA | AAAAGGAAGA | GTATGAGTAT | TCAACATTTC | CGTGTCGCCC TTATTCCCTT |
| 3361 | TTTTGCGGCA | TTTTGCCTTC | CTGTTTTTGC | TCACCCAGAA | ACGCTGGTGA AAGTAAAAGA |
| 3421 | TGCTGAAGAT | CAGTTGGGTG | CACGAGTGGG | TTACATCGAA | CTGGATCTCA ACAGCGGTAA |
| 3481 | GATCCTTGAG | AGTTTTCGCC | CCGAAGAACG | TTTTCCAATG | ATGAGCACTT TTAAAGTTCT |
| 3541 | GCTATGTGGC | GCGGTATTAT | CCCGTATTGA | CGCCGGGCAA | GAGCAACTCG GTCGCCGCAT |
| 3601 | ACACTATTCT | CAGAATGACT | TGGTTGAGTA | CTCACCAGTC | ACAGAAAAGC ATCTTACGGA |

-continued

```
3661  TGGCATGACA GTAAGAGAAT TATGCAGTGC TGCCATAACC ATGAGTGATA ACACTGCGGC
3721  CAACTTACTT CTGACAACGA TCGGAGGACC GAAGGAGCTA ACCGCTTTTT TGCACAACAT
3781  GGGGGATCAT GTAACTCGCC TTGATCGTTG GGAACCGGAG CTGAATGAAG CCATACCAAA
3841  CGACGAGCGT GACACCACGA TGCCTGTAGC AATGGCAACA ACGTTGCGCA AACTATTAAC
3901  TGGCGAACTA CTTACTCTAG CTTCCCGGCA ACAATTAATA GACTGGATGG AGGCGGATAA
3961  AGTTGCAGGA CCACTTCTGC GCTCGGCCCT TCCGGCTGGC TGGTTTATTG CTGATAAATC
4021  TGGAGCCGGT GAGCGTGGGT CTCGCGGTAT CATTGCAGCA CTGGGGCCAG ATGGTAAGCC
4081  CTCCCGTATC GTAGTTATCT ACACGACGGG GAGTCAGGCA ACTATGGATG AACGAAATAG
4141  ACAGATCGCT GAGATAGGTG CCTCACTGAT TAAGCATTGG TAACTGTCAG ACCAAGTTTA
4201  CTCATATATA CTTTAGATTG ATTTAAAACT TCATTTTTAA TTTAAAAGGA TCTAGGTGAA
4261  GATCCTTTTT GATAATCTCA TGACCAAAAT CCCTTAACGT GAGTTTTCGT TCCACTGAGC
4321  GTCAGACCCC GTAGAAAAGA TCAAAGGATC TTCTTGAGAT CCTTTTTTTC TGCGCGTAAT
4381  CTGCTGCTTG CAAACAAAAA AACCACCGCT ACCAGCGGTG GTTTGTTTGC CGGATCAAGA
4441  GCTACCAACT CTTTTTCCGA AGGTAACTGG CTTCAGCAGA GCGCAGATAC CAAATACTGT
4501  TCTTCTAGTG TAGCCGTAGT TAGGCCACCA CTTCAAGAAC TCTGTAGCAC CGCCTACATA
4561  CCTCGCTCTG CTAATCCTGT TACCAGTGGC TGCTGCCAGT GGCGATAAGT CGTGTCTTAC
4621  CGGGTTGGAC TCAAGACGAT AGTTACCGGA TAAGGCGCAG CGGTCGGGCT GAACGGGGGG
4681  TTCGTGCACA CAGCCCAGCT TGGAGCGAAC GACCTACACC GAACTGAGAT ACCTACAGCG
4741  TGAGCTATGA GAAAGCGCCA CGCCTTCCCG AAGGGAGAAA GGCGGACAGG TATCCGGTAA
4801  GCGGCAGGGT CGGAACAGGA GAGCGCACGA GGGAGCTTCC AGGGGGAAAC GCCTGGTATC
4861  TTTATAGTCC TGTCGGGTTT CGCCACCTCT GACTTGAGCG TCGATTTTTG TGATGCTCGT
4921  CAGGGGGGCG GAGCCTATGG AAAAACGCCA GCAACGCGGC CTTTTTACGG TTCCTGGCCT
4981  TTTGCTGGCC TTTTGCTCAC ATGTTCTTTC CTGCGTTATC CCCTGATTCT GTGGATAACC
5041  GTATTACCGC CTTTGAGTGA GCTGATACCG CTCGCCGCAG CCGAACGACC GAGCGCAGCG
5101  AGTCAGTGAG CGAGGAAGCG GAAGAGCGCC AATACGCAA ACCGCCTCTC CCCGCGCGTT
5161  GGCCGATTCA TTAATCCAAC TGGCACGACA GGTTTCCCGA CTGGAAAGCG GGCAGTGAGC
5221  GCAACGCAAT TAATGTGAGT TAGCTCACTC ATTAGGCACC CCAGGCTTTA CACTTTATGC
5281  TTCCGGCTCG TATGTTGTGT GGAATTGTGA GCGGATAACA ATTTCACACA GGAAACAGCT
5341  ATGACATGAT TA.
```

2. Enzymes: AgeI, SalI, BsiWI, XhoI, SgrAI, NheI, NotI, T4 DNA Ligase
    3. DH5-alpha competent cells
    4. QIAGEN QIAEX II® Gel Extraction Kit, QIAGEN MinElute® Reaction Cleanup Kit, QIAGEN QIAprep® Spin Miniprep Kit
    5. VH and VK/VL DNA from RT-PCR
    1) VH DNA from RT-PCR (1st 5'VH Mix paired with 1st 3'VH Mix)
    2) VK DNA from RT-PCR (1st 5'VK Mix paired with 1st 3'VK Mix)
    Or VL DNA from RT-PCR (1st 5'VL Mix paired with 1st 3'VL Mix)
    3) IgG-VH DNA from RT-PCR (1st 5'VH Mix paired with 3'IgG-CH1 Mix)
    4) IgG-CH DNA from RT-PCR (1st 5'VH Mix paired with 3'IgG-HCstop Mix)
    5) IgCK DNA from RT-PCR (1st 5'VK Mix paired with 3'IgCKstop Mix)
    6) Or IgCL DNA from RT-PCR (1st 5'VL Mix paired with 3'IgCLstop Mix).
    B) Procedures: Cloning of Human mAb VH and VK/VL Genes
    1. Preparation of Vectors:
    1) VH Vector:
    p19EH-AS6 digested with AgeI and SalI, then isolate the vector DNA (larger band, ~5.7 Kb) after Argrose Gel electrophoresis.
    2) VK Vector:
    p14B7K-SN1 digested with AgeI and BsiWI, then isolate the vector DNA (larger band, ~5.0 Kb) after Agarose Gel electrophoresis.

3) VL Vector:

pA32L-SN5 digested with AgeI and XhoI, then isolate the vector DNA (larger band, ~4.9 Kb) after Argrose Gel electrophoresis.

4) IgG-VH Vector:

p19EH-AS6 digested with AgeI and NheI, then isolate the vector DNA (larger band, ~5.7 Kb) after Argrose Gel electrophoresis.

5) IgC Vector:

p19EH-AS6 digested with AgeI and NotI, then isolate the vector DNA (larger band, ~4.5 Kb) after Argrose Gel electrophoresis.

*Note: make sure all vectors are completely double-digested fragments. This can be tested by a self-ligation and transformation of DH5-alpha competent cells, No or rare colonies are an indication of good vector preparation.

2. Preparation of Inserts:

1) VH Gene Insert:

VH gene RT-PCR DNA digested with AgeI and SalI, then purified with QIAGEN MinElute® Reaction Cleanup Kit.

2) VK Gene Insert:

VK gene RT-PCR DNA digested with AgeI and BsiWI, then purified with QIAGEN MinElute® Reaction Cleanup Kit.

3) VL Gene Insert:

VL gene RT-PCR DNA digested with AgeI and XhoI, then purified with QIAGEN MinElute® Reaction Cleanup Kit.

4) IgG-VH Gene Insert:

IgG-VH DNA from RT-PCR DNA digested with AgeI and NheI, then purified with QIAGEN MinElute® Reaction Cleanup Kit.

5) IgG-CH, Ig-CK and Ig-CL Insert:

IgG-CH, Ig-CK and Ig-CL gene RT-PCR DNA digested with AgeI and NotI, then purified with QIAGEN MinElute® Reaction Cleanup Kit.

3. Ligation and Transformation

1) Run 1 ul of each vectors and VH, VK/VL inserts DNA on 1.2% Agarose Gel to check purity and to estimate relative DNA concentration.

*Note: make sure that PCR DNA bands are not cut into two or more bands. If the PCR DNA were cut into pieces, alternative enzymes should be used to cut the PCR DNA (Use SgrAI instead of AgeI, or clone IgG-VH instead of VH, or clone IgG-CH, Ig-CK and Ig-CL instead of VH, VK and VL, respectively)

2) Set up DNA ligations for each of the VH, VK/VL vector and insert pairs, using vector/insert ratio of 1:4.

3) Transform the ligated DNA into DH5-alpha competent cells. Each spread into two LB-Amp+ plates.

*Note: make sure that vector self-ligations do not have colonies (a few are acceptable) and that insert transformations have at least 50 colonies per plate.

Part III: Expression Cloning of Human mAb VH and VK/VL Genes (Continued).

A) Reagents

1. QIAGEN QIAprep® Spin Miniprep Kit, QIAGEN Plasmid Maxi Prep Kit
2. Invitrogen Lipofectamine® 2000 and Roche's FuGENE® 6
3. 293T cell and its culture Medium
4. Sequencing primer:

```
Ig-F864:
GTCCAACTGCACCTCGGTTC      (SEQ ID NO: 164)
```

B) Procedures: Screening for Desired VH and VK/VL Gene Pair Clones

1. Preparation of Plasmid Mini-Libraries:

1) VH Gene Clones Mini-Libraries (VHm)

Combine all colonies from one of the two plates for VH clones as VH mini-libraries. Grow up and then isolate plasmid DNA with QIAprep Spin Miniprep Kit to obtain VHm. Test concentration and purity (OD260/280)

2) VK Gene Clones Mini-Libraries (VKm) for mAb Using Kappa Light Chain.

Combine all colonies from one of the two plates for VK clones as VK mini-libraries. Grow up and then isolate plasmid DNA with QIAprep Spin Miniprep Kit to obtain VKm. Test concentration and purity (OD260/280)

3) VL Gene Clones Mini-Libraries (VLm) for mAb Using Lambda Light Chain.

Combine all colonies from one of the two plates for VL clones as VL mini-libraries. Grow up and then isolate plasmid DNA with QIAprep Spin Miniprep Kit to obtain VLm. Test concentration and purity (OD260/280)

2. Screening Mini-Libraries by Transfection in 96 Well Plate Format:

1) Refresh 293T cells one day before transfection.

2) Mix 0.15 ug VHm DNA with 0.15 ug VKm or VLm DNA in total 25 ul/well plain medium.

3) Dilute 0.5 ul Lipofectamine 2000 in 25 ul/well plain medium, RT for 5 min. (Can make master mixture).

4) Add 25 ul/well diluted Lipofectamine 2000 to DNA mixture wells, RT 15 min.

5) Add 150 ul/well of 293T cells (0.4 million/ml in complete medium), culture for 2-3 days 6) Take supernatant (100 ul/well) and diluted into 150 ul/well blotto buffer, then tested for Ab activity and total IgG concentration by ELISAs.

7) If Ab reactivity ELISA results show positive (even weak), then go to step 3. If total IgG concentration is low (<0.5 ug/ml), then repeat DNA preparation and/or the transfection to get a good yield of IgG. If Ab reactivity ELISA results show negative and total IgG concentration is normal (>1 ug/ml), then stop at this point (may have to optimize RT-PCR by using individual or subfamily specific 5' primers to repeat the RT-PCR.).

3. Screening for Desired VH and VK or VL Gene Clones:

1) Isolate VH and VK or VL plasmid DNAs from individual colonies from the other plate of transformations. Obtain VHn (1, 2 ... n) and VKn or VLn DNA. Generally, 24 VH colonies and 24 Vk or VL colonies are good start.

2) Refresh 293T cells one day before transfection.

3) For VH clones, mix 0.15 ug VHn DNA with 0.15 ug VKm or VLm DNA in total 25 ul/well plain medium. For VK or VL clones, mix 0.15 ug VHm DNA with 0.15 ug VKn or VLn DNA in total 25 ul/well plain medium 4) Dilute 0.5 ul Lipofectamine 2000 in 25 ul/well plain medium, RT for 5 min. (Can make master mixture).

5) add 25 ul/well diluted Lipofectamine 2000 to DNA mixture wells, RT 15 min.

6) Add 150 ul/well of 293T cells (0.4 million/ml in complete medium), culture for 2-3 days 7) Take supernatant (100 ul/well) and diluted into 150 ul/well blotto buffer, then tested for Ab activity by ELISA.

8) If Ab reactivity ELISA results for VHn, VKn or VLn show positive (usually obvious), then go to step 4. If negative for any of VHn or VKn or VLn, then isolate more colonies and repeat until at least one positive clone for each of VH and VK or VL genes are identified.

4. Confirmation of Identified VH and VK or VL Gene Clones:

1) Sequencing the identified VH and VK or VL gene clones, make sure they are functional VH, VK or VL genes and there is no contamination from vectors.

2) Refresh 293T cells one day before transfection.

3) Mix 0.15 ug of the identified VHn DNA with 0.15 ug of the identified VKn or VLn DNA in total 25 ul/well plain medium.

4) Dilute 0.5 ul Lipofectamine 2000 in 25 ul/well plain medium, RT for 5 min. (Can make master mixture).

5) Add 25 ul/well diluted Lipofectamine 2000 to DNA mixture wells, RT 15 min.

6) Add 150 ul/well of 293T cells (0.4 million/ml in complete medium), culture for 2-3 days 7) Take supernatant (100 ul/well) and diluted into 150 ul/well blotto buffer, then tested for Ab activity and total IgG concentration by ELISAs.

8) If Ab reactivity ELISA results for the identified VHn, VKn or VLn pairs show positive (usually obvious, strong positive), then go to Step 5. If negative, check any mistakes in step 3.

5. Production of Human mAbs:

1) Maxiprep the identified VHn and VKn or VLn clones

2) Produce mAbs by transfection of 293T cells following instruction of FuGENE® 6 reagent 3) Purify mAbs by Protein A or Protein G methods.

Example 6

Anti-HIV-1 gp120 Antibodies Cloned from Human $B_{Mem}$ Cells

Tables 3 and 4 provide examples of human antibodies that specifically bind to HIV gp120. These antibodies were cloned from human $B_{Mem}$ cells using the methods described herein. Table 3 shows the characteristics of the heavy chain gene and Table 4 shows the characteristics of the light chain gene for each antibody cloned.

Shown for each antibody listed is the mAb binding specificity for HIV gp120 (CD4i, CD4bs, or "other" for another region of gp120), the mAb identification number, and the genes that recombined to form the heavy chain or light chain. Also shown is the amino acid sequence of the third complementarity determining region (CDR-3) for the heavy chain (CDR-H3) or light chain (CDR-L3). Also shown is the length of the CDR-H3 for the heavy chain of each antibody listed, as well as the length of each of the three CDRs for the light chain of each antibody listed. The complementarity determining regions are the hypervariable regions of each antibody chain, and are involved in determining the binding specificity of an antibody. While not wishing to be bound by theory, it is thought that CDR-3 is the most crucial of the three CDRs in terms of determining the binding specificity of an antibody.

TABLE 3

Gene Profile of New mAbs against HIV-1 gp120: Heavy Chain Gene

| mAb Specificity | mAb ID | V-gene | D-gene | J-gene | CDR-H3 Amino Acid Sequence | CDR3 Length |
|---|---|---|---|---|---|---|
| CD4i | N26-I1 | HV1-69*08 | D3-9*01 | J4*02 | AGTVYYDILTGLYTNFHY (SEQ ID NO: 73) | 18 |
| CD4i | N5-I1 | HV1-69*01/05 | D3-22*01 | J3*01 | ARDSGLDYFDSAGYNEPFDV (SEQ ID NO: 74) | 20 |
| CD4i | N5-I2 | HV4-31*03 | D4-23*01 | J5*02 | ARVHGNSGLNWFDP (SEQ ID NO: 75) | 14 |
| CD4i | N5-I3 | HV1-69*01/05 | D3-22*01 | J6*02 | ATEGDDNTYYYDSSGYYYYGMDV (SEQ ID NO: 76) | 23 |
| CD4i | N5-I4 | HV1-69*05 | D4-17*01 | J6*02 | ASGIRGADYGDDVGHYYYGVDV (SEQ ID NO: 77) | 22 |
| CD4i | N5-I5 | HV3-23*04 | D3-10*01 | J4*02 | AKDLRLGGGSDY (SEQ ID NO: 78) | 12 |
| CD4i | N5-I6 | HV1-69*01 | D4-17*01 | J2*01 | ARAELEPNDYGDSPHVRWYFDL (SEQ ID NO: 79) | 22 |
| CD4i | N5-I7 | HV1-69*01 | D4-17*01 | J6*03 | ASAEENDYGESEGPPYFYYYMDV (SEQ ID NO: 80) | 23 |
| CD4i | N5-I8 | HV1-69*01 | D4-17*01 | J6*03/04 | AGTGPPNDYGDDVVHEGYYYNYLDV (SEQ ID NO: 81) | 25 |
| CD4i | N5-I9 | HV1-69*01 | D3-22*01 | J4*02 | AKEADWDYYDTSVYPFAY (SEQ ID NO: 82) | 18 |
| CD4i | N5-I10 | HV1-69*10 | D5-5*01 | J4*02 | ARDHPDSEGGGY (SEQ ID NO: 83) | 12 |
| CD4i | N5-I11 | HV5-51*01 | D6-19*01 | J3*02 | ARIAVAGVGAFDI (SEQ ID NO: 84) | 13 |
| CD4i | N5-I12 | HV1-69*12 | D3-22*01 | J4*02 | ATVIFGGPDYYHSGDVGETGAVYYFDN (SEQ ID NO: 85) | 27 |

TABLE 3-continued

Gene Profile of New mAbs against HIV-1 gp120: Heavy Chain Gene

| mAb Specificity | mAb ID | V-gene | D-gene | J-gene | CDR-H3 Amino Acid Sequence | CDR3 Length |
|---|---|---|---|---|---|---|
| CD4i | N5-I13 | HV1-69*02 | D3-22*01 | J4*02 | ASGTEPDYADSSGYYWFDC (SEQ ID NO: 86) | 19 |
| CD4i | N5-I14 | HV1-69*12 | D3-22*01 | J3*02 | ATDGARDTDYYDSSGYLLFIAFDI (SEQ ID NO: 87) | 24 |
| CD4i | N5-I15 | HV1-69*01 | D4-17*01 | J6*03/04 | AGTGPPNDYGDDVVHEGYYYNYLDV (SEQ ID NO: 88) | 25 |
| CD4i | N12-I1 | HV1-69*02 | D3-22*01 | J3*02 | ASWAGYYDSSSYPLSAFDI (SEQ ID NO: 89) | 19 |
| CD4i | N12-I2 | HV1-69*05 | D4-17*01 | J6*02 | ASDSRDFSYYEPGTSYSHYYNIMDV (SEQ ID NO: 90) | 25 |
| CD4i | N12-I3 | HV1-69*02 | D2-2*01 | J1*01 | ASRQHHEYFQE (SEQ ID NO: 91) | 11 |
| CD4i | N12-I4 | HV1-69*05 | D5-5*01 | J3*02/6*02 | ARAPLGRNSYGPDGTGDAFDM (SEQ ID NO: 92) | 21 |
| CD4i | N12-I5 | HV1-69*02 | D5-12*01 | J3*01 | ASWAGYYDSPSYPLSAFDV (SEQ ID NO: 93) | 19 |
| CD4i | N12-I6 | HV1-69*02 | D3-22*01 | J3*02 | ASWAGYYDSSSYPLSAFDI (SEQ ID NO: 89) | 19 |
| CD4i | N12-I7 | HV1-69*05 | D2-21*02 | J6*02 | ASGGDSDYYEIGRTYHYYYAMDV (SEQ ID NO: 94) | 23 |
| CD4i | N12-I8 | HV5-51*03 | D6-6*01 | J5*02 | VRRNLSGDRGGWFDP (SEQ ID NO: 95) | 15 |
| CD4i | N12-I9 | HV1-69*05 | D3-16*02 | J6*02/3*01 | AGSPEGPNDYVWGTYRPGAFLYYGLDV (SEQ ID NO: 96) | 27 |
| CD4i | N12-I10 | HV1-69*02 | D3-22*01 | J3*02 | ASWAGYYDSSSYPLSAFDI (SEQ ID NO: 89) | 19 |
| CD4i | N12-I11 | HV1-69*02 | D3-22*01 | J3*02 | ASWAGYYDSSSYPLSAFDI (SEQ ID NO: 89) | 19 |
| CD4i | N12-I12 | HV1-69*05 | D4-17*01 | J6*02 | AAIDYGDFAYYYGMDV (SEQ ID NO: 97) | 16 |
| CD4i | N12-I13 | HV1-69*02 | D3-22*01 | J3*02 | ASWAGYYDSSSYPLSAFDI (SEQ ID NO: 89) | 19 |
| CD4i | N12-I14 | HV1-69*10 | D3-22*01 | J3*01 | ASDHGADDYDSGAFLSAFGF (SEQ ID NO: 98) | 21 |
| CD4i | N12-I15 | HV1-46*01 | D5-24*01 | J4*02 | ARDLEMRDGNNHGSHLEF (SEQ ID NO: 99) | 18 |
| CD4i | N12-I16 | HV1-69*10 | D3-22*01 | J3*01 | ASDHGADDYDSGAFLSAFGF (SEQ ID NO: 100) | 21 |
| CD4i | N12-I17 | HV1-69*02 | D5-12*01 | J3*01 | ASWAGYYDSPSYPLSAFDV (SEQ ID NO: 101) | 19 |
| CD4i | N12-I18 | HV1-69*02 | D3-22*01 | J3*02 | ASWAGYYDSSSYPLSAFDI (SEQ ID NO: 89) | 19 |
| CD4i | N12-I19 | HV1-69*02 | D3-22*01 | J3*02 | ASWAGYYDSSSYPLSAFDI (SEQ ID NO: 89) | 19 |
| CD4i | L9-I1 | HV3-23*01 | D3-10*01 | J3*01 | AKDLSVGQWPPINAFDV (SEQ ID NO: 102) | 17 |
| CD4i | L9-I2 | HV1-69*02 | D5-24*01 | J4*01 | VRDRSNLAFEY (SEQ ID NO: 103) | 11 |

TABLE 3-continued

Gene Profile of New mAbs against HIV-1 gp120: Heavy Chain Gene

| | | Heavy Chain Gene | | | | |
|---|---|---|---|---|---|---|
| mAb Specificity | mAb ID | V-gene | D-gene | J-gene | CDR-H3 Amino Acid Sequence | CDR3 Length |
| CD4i | L9-I3 | HV1-24*01 | D3-16*01 | J5*01 | ATSVTYETNAYYCFDS (SEQ ID NO: 104) | 16 |
| CD4i | L9-I4 | HV2-70*04 | D3-10*01 | J5*01 | ARSSGSYYHNFDY (SEQ ID NO: 105) | 13 |
| CD4bs | N12-B1 | HV3-48*03 | D3-10*01 | J4*02 | ARNPNDRFPFTVVRGVSFDY (SEQ ID NO: 106) | 20 |
| CD4bs | N12-B2 | HV4-b*01 | D3-3*01 | J5*02 | ARHDAEYDFWGSGRLRGWFGP (SEQ ID NO: 107) | 21 |
| CD4bs | N12-B3 | HV4-b*01 | D3-3*01 | J5*03 | AKHDAQYDFVWNSGRVRGWFDP (SEQ ID NO: 108) | 22 |
| CD4bs | N12-B4 | HV4-b*01 | D3-3*01 | J5*03 | AKHDAQYDFVWNSGRVRGWFDP (SEQ ID NO: 108) | 22 |
| CD4bs | Ni2-B5 | HV4-b*01 | D3-3*01 | J5*03 | AKHDAQYDFVWNSGRVRGWFDP (SEQ ID NO: 108) | 22 |
| CD4bs | L9-B1 | HV1-18*01 | D3-22*01 | J3*02 | ARTFTYYFDEVDWAQSFDI (SEQ ID NO: 109) | 19 |
| CD4bs | L9-B2 | HV1-18-*01 | D3-16*01 | j3*01 | ARTFTYYFDDVDWAQSFDV (SEQ ID NO: 110) | 19 |
| CD4bs | L9-B3 | HV1-18-*01 | D4-17*01 | J6*03 | ARRSYDYGDDDVDLVTDYYYYMDV (SEQ ID NO: 111) | 24 |
| Other | N5-O1 | HV5-51*01 | D4-23*01 | J3*01 | ARFDAGYSETTDSNALDV (SEQ ID NO: 112) | 18 |
| Other | N12-O1 | HV1-1*01 | D3-22*01 | J3*02 | ATGRMGYYDSSGYHYVGLFQM (SEQ ID NO: 113) | 21 |
| Other | N12-O2 | HV1-69*05 | D5-12*01 | J4*02 | VRDGDDGDY (SEQ ID NO: 114) | 9 |
| Other | O3.1 | HV1-46*01/2/3 | D3-3*01 | J3*01 | AREWNRDSDWSPYYHAFDV (SEQ ID NO: 115) | 20 |

TABLE 4

Gene Profile of New mAbs against HIV-1 gp120: Light Chain Gene

| | | Light Chain Gene | | | |
|---|---|---|---|---|---|
| mAb specificity | mAb ID | V-gene | J-gene | CDR-L3 | CDR length |
| CD4i | N26-I1 | LV3-1*01 | J2*01/3*01 | QAWASTTVI (SEQ ID NO: 116) | 6, 3, 9 |
| CD4i | N5-I1 | KV3-20*1 | J5*01 | QQYANSPIT (SEQ ID NO: 117) | 7, 3, 9 |
| CD4i | N5-I2 | LV3-25*03 | J2*01/3*01 | QAADSTGIYPT (SEQ ID NO: 118) | 6, 3, 11 |
| CD4i | N5-I3 | LV3-25*01 | J2*01/3*01 | QAADSTGIYPT (SEQ ID NO: 118) | 6, 3, 11 |
| CD4i | N5-I4 | KV1-16*02 | J2*01 | QQYKSFPYT (SEQ ID NO: 119) | 6, 3, 9 |
| CD4i | N5-I5 | LV2-23*02 | J3*02 | SSYAGSTTFRV (SEQ ID NO: 120) | 9, 3, 11 |

TABLE 4-continued

Gene Profile of New mAbs against HIV-1 gp120: Light Chain Gene

| mAb specificity | mAb ID | V-gene | J-gene | CDR-L3 | CDR length |
|---|---|---|---|---|---|
| | | | Light Chain Gene | | |
| CD4i | N5-I6 | KV3-11*01 | J4*01 | LHHSNWPPSLT (SEQ ID NO: 121) | 6, 3, 11 |
| CD4i | N5-I7 | KV1-16*02 | J4*01 | QQYNSLPLT (SEQ ID NO: 122) | 6, 3, 9 |
| CD4i | N5-I8 | KV1-5*03 | J2*03 | QQYNSYPYS (SEQ ID NO: 123) | 6, 3, 9 |
| CD4i | N5-I9 | KV3-20*01 | J4*01 | QQYGSTPLT (SEQ ID NO: 124) | 7, 3, 9 |
| CD4i | N5-I10 | KV1-5*03 | J2*01 | QQYNTYPYT (SEQ ID NO: 125) | 6, 3, 9 |
| CD4i | N5-I11 | LV1-44*01 | J3*02 | AAWDDSLNGWV (SEQ ID NO: 126) | 8, 3, 11 |
| CD4i | N5-I12 | KV1-8*01 | J4*01 | QQYYSSPLT (SEQ ID NO: 127) | 6, 3, 9 |
| CD4i | N5-I13 | KV3-15*01 | J2*01 | QQYNNWPYT (SEQ ID NO: 128) | 6, 3, 9 |
| CD4i | N5-I14 | KV3-20*01 | J1*01 | QQYSSSPIT (SEQ ID NO: 129) | 7, 3, 9 |
| CD4i | N5-I15 | KV3-20*01 | J2*04/4*01 | QQYGGSVSS (SEQ ID NO: 130) | 7, 3, 9 |
| CD4i | N12-I1 | KV1-5*03 | J3*01 | QQYSSDWVT (SEQ ID NO: 131) | 6, 3, 9 |
| CD4i | N12-I2 | KV3-20*01 | J1*01 | QQYGSSPET (SEQ ID NO: 132) | 7, 3, 9 |
| CD4i | N12-I3 | KV3-20*01 | J4*01 | QQYGTSPLT (SEQ ID NO: 133) | 7, 3, 9 |
| CD4i | N12-I4 | KV1-5*03 | J2*03/2*04 | QQYNSYSSS (SEQ ID NO: 134) | 6, 3, 9 |
| CD4i | N12-I5 | KV1-5*03 | J2*03 | QQYNSYPYS (SEQ ID NO: 135) | 6, 3, 9 |
| CD4i | N12-I6 | KV1-5*03 | J3*01 | QQYSSDWVT (SEQ ID NO: 136) | 6, 3, 9 |
| CD4i | N12-I7 | KV1-5*03 | J1*01 | QQYNTWT (SEQ ID NO: 137) | 6, 3, 7 |
| CD4i | N12-I8 | KV1-5*03 | J2*03/2*04 | QQYNSYSSS (SEQ ID NO: 138) | 6, 3, 9 |
| CD4i | N12-I9 | KV2D-29*02 | J4*01 | MQSIQPPLT (SEQ ID NO: 139) | 11, 3, 9 |
| CD4i | N12-I10 | KV1-9*01 | J4*01 | QQYDTLPPT (SEQ ID NO: 140) | 6, 3, 9 |
| CD4i | N12-I11 | KV1-5*03 | J1*01 | QQYNSYSWT (SEQ ID NO: 141) | 6, 3, 9 |
| CD4i | N12-I12 | KV1-5*03 | J4*01 | QQYSTYPLT (SEQ ID NO: 142) | 6, 3, 9 |
| CD4i | N12-I13 | KV1-5*03 | J3*01 | QQYSSDWVT (SEQ ID NO: 143) | 6, 3, 9 |
| CD4i | N12-I14 | KV1-9*01 | J4*01 | QQLNTYPLT (SEQ ID NO: 144) | 6, 3, 9 |

TABLE 4-continued

Gene Profile of New mAbs against HIV-1 gp120: Light Chain Gene

| mAb specificity | mAb ID | V-gene | J-gene | CDR-L3 | CDR length |
|---|---|---|---|---|---|
| CD4i | N12-I15 | KV2-28*01 | J2*01/2*02 | MQAKESPT (SEQ ID NO: 145) | 11, 3, 8 |
| CD4i | N12-I16 | LV1-40*01 | J3*02 | QSYDYRLSGSGV (SEQ ID NO: 146) | 9, 3, 12 |
| CD4i | N12-I17 | KV1-5*03 | J2*01/3*01 | QHYNSYSIT (SEQ ID NO: 147) | 6, 3, 9 |
| CD4i | N12-I18 | KV1-5*03 | J1*01 | QQYNTYSQT (SEQ ID NO: 148) | 6, 3, 9 |
| CD4i | N12-I19 | KV1-5*03 | J2*03 | QQYNSLPYS (SEQ ID NO: 149) | 6, 3, 9 |
| CD4i | L9-I1 | KV3-20*01, | J2*01 | QYYGRSPPYT (SEQ ID NO: 150) | 7, 3, 10 |
| CD4i | L9-I2 | KV1-8*01/9*01 | J1*01 | QQLNSYPPT (SEQ ID NO: 151) | 6, 3, 9 |
| CD4i | L9-I3 | KV3-11*01 | J2*01 | QQRTNWPPYMYT (SEQ ID NO: 152) | 6, 3, 12 |
| CD4i | L9-I4 | kv1-39*01 | J1*01 | QQSYTTPPT (SEQ ID NO: 153) | 6, 3, 9 |
| CD4bs | N12-B1 | KV1-5*01 | J3*01 | QQYYVYPFT (SEQ ID NO: 154) | 6, 3, 9 |
| CD4bs | N12-B2 | KV3-20*01 | J4*01 | QQYAHSPLT (SEQ ID NO: 155) | 7, 3, 9 |
| CD4bs | N12-B3 | KV3-20*01 | J4*01 | QQYGSSPLT (SEQ ID NO: 156) | 6, 3, 9 |
| CD4bs | N12-B4 | KV3-20*01 | J4*01 | QQYGSSPLT (SEQ ID NO: 156) | 7, 3, 9 |
| CD4bs | N12-B5 | KV3-20*01 | J4*01 | QQYGSSLPLT (SEQ ID NO: 157) | 7, 3, 10 |
| CD4bs | L9-B1 | KV3-20*01 | J3*01 | QLYDSSPLFT (SEQ ID NO: 158) | 7, 3, 10 |
| CD4bs | L9-B2 | KV3-15*01 | J1*01 | QHYNNWPPWT (SEQ ID NO: 159) | 6, 3, 10 |
| CD4bs | L9-B3 | KV3-15*01 | J2*01 | QHYNNWPPWT (SEQ ID NO: 159) | 6, 3, 10 |
| Other | N5-O1 | LV1-47*01 | J3*02 | ATWDDTLSGPL (SEQ ID NO: 160) | 8, 3, 11 |
| Other | N12-O1 | KV1-55*03 | J1*01 | QQYDTYPWT (SEQ ID NO: 161) | 6, 3, 9 |
| Other | N12-O2 | LV2-14*01 | J2*01 | NSYTTSNTLV (SEQ ID NO: 162) | 9, 3, 10 |
| Other | N12-O3.1 | KV4-1*01 | J2*01 | QQYYSTPYT (SEQ ID NO: 163) | 12, 3, 9 |

Example 7

Neutralization of HIV-1 Pseudovirus Using Anti-HIV-1 gp120 Antibodies Cloned from Human $B_{Mem}$ Cells Table 5 shows neutralization assays of HIV-1 pseudovirus using anti-HIV-1 gp120 antibodies cloned from human $B_{Mem}$ cells as described herein. Neutralization assays were performed by standard methods (Montefiori, D. C. (2004) Evaluating neutralizing antibodies against HIV, SIV and SHIV in luciferase reporter gene assays. Current Protocols in Immunology, (Coligan, J. E., et al., W. Strober, and R. Coico, eds.), John Wiley & Sons, 12.11.1-12.11.15. The $IC_{50}$ of each antibody is shown below.

Example 8

Figure 11A:
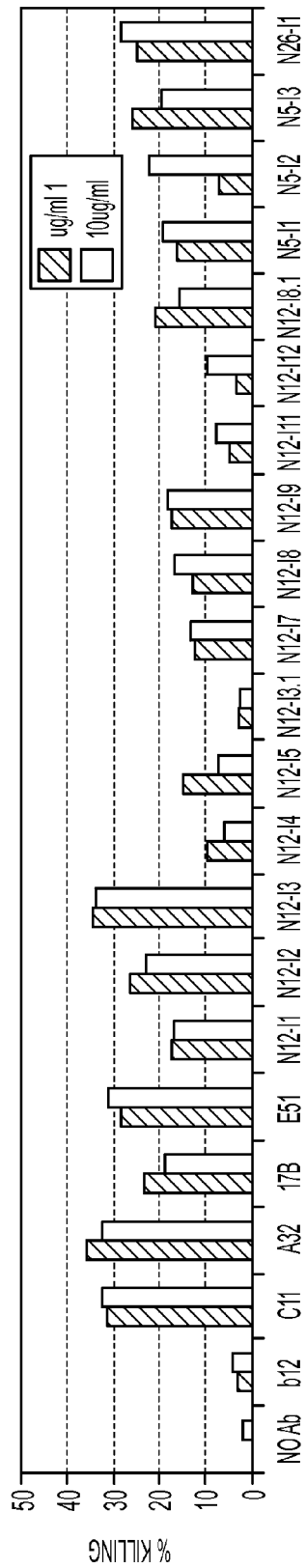
FIG. 11A-C. Graphs showing antibody-dependent cell-mediated cytotoxicity (ADCC) assays using anti-HIV-1 gp120 antibodies cloned from human B$_{Mem}$ cells using the methods described herein.
Figure 11B:
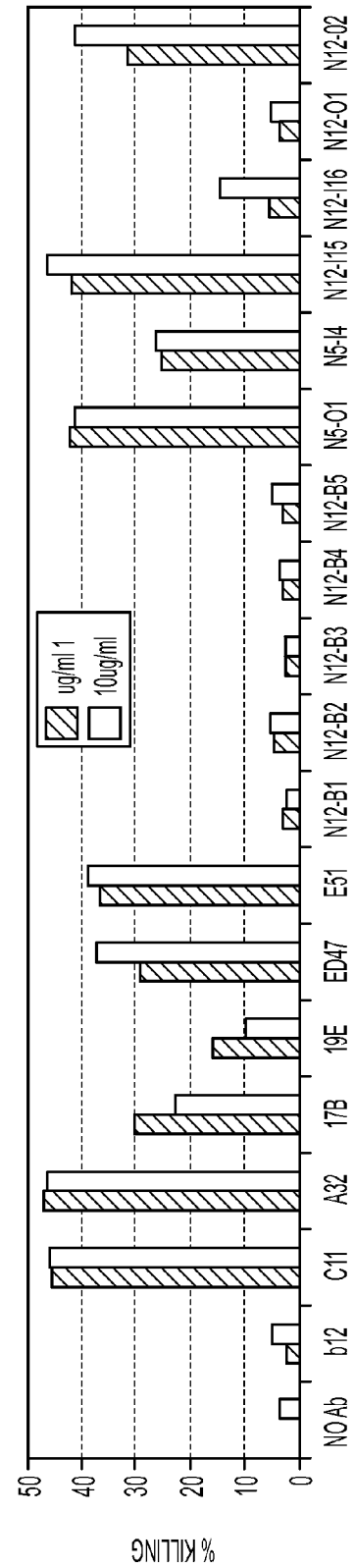
Figures 1, 11C:
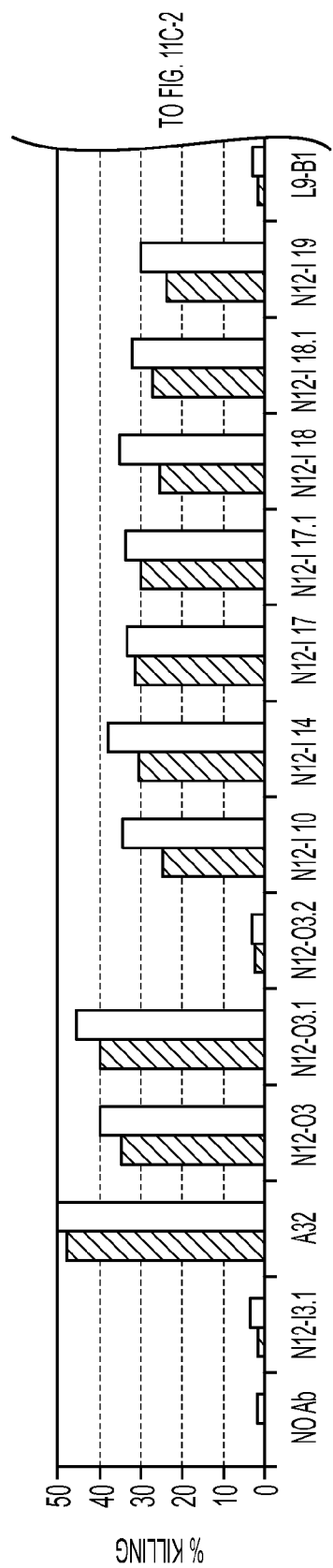
Figures 2, 11C:
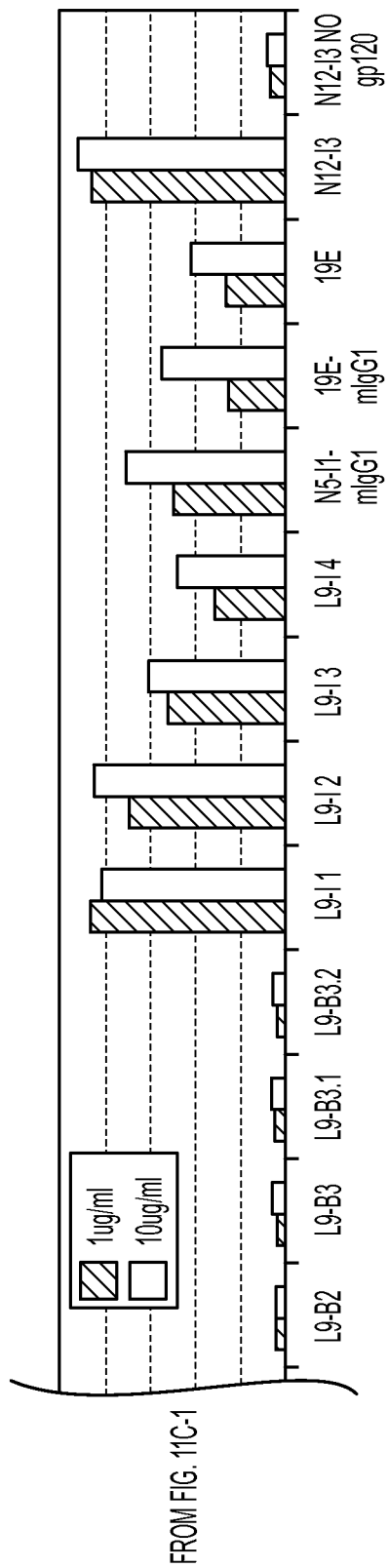
FIG. 2. Identification of HIV-1 Env specific B$_{Mem}$. One hundred B$_{Mem}$ per well were stimulated for 2 weeks and supernatants were screened for total CD4i, CD4bs, and 'Other' HIV-1 Env protein specific B$_{Mem}$ by ELISA using a mixture of anti-k and anti-l Abs. A) Representative ELSIA data for supernantants of NVS10. B) HIV-1 Env specific B$_{Mem}$ in three NVS donors are shown as frequency per million total B$_{Mem}$. The detection limit is 10 precursors per million B$_{Mem}$. C) Percentages of B$_{Mem}$ of CD4i (blue), CD4bs (red) and 'Other' specificities (yellow) in each of NVS5, NVS9 and NVS10 donors are shown in a pie chart.

ADCC Assays Using Anti-HIV-1 gp120 Antibodies Cloned from Human $B_{Mem}$ Cells FIG. 11A-C are graphs showing antibody-dependent cell-mediated cytotoxicity (ADCC) assays using the exemplary anti-HIV-1 gp120 antibodies cloned from human $B_{Mem}$ cells as described herein. ADCC assays were performed as described (Gómez-Román V R, et al., A simplified method for the rapid fluorometric assessment of antibody-dependent cell-mediated cytotoxicity. *J Immunol Methods*. 2006 Jan. 20; 308(1-2):53-67. Epub 2005 Nov. 28).

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

TABLE 5

Neutralization of HIV-1 pseudovirus in TZM-BL indicator cell line

| IC50 (ug/ml) | SF162 | JRFL | BaL.01 | ADA | SVPB5 | SVPB12 | SVPB14 | SVPB16 | SVPB17 | MuLV | HIV2 | HIV2 + sCD4 |
|---|---|---|---|---|---|---|---|---|---|---|---|---|
| N12-I1 | 30 | >30 | >30 | >30 | >30 | >30 | >30 | >30 | >30 | >30 | >30 | >30 |
| N12-I2 | 10 | >30 | >30 | >30 | >30 | >30 | >30 | 30 | >30 | >30 | >30 | 9 |
| N12-I3 | >30 | >30 | >30 | >30 | >30 | >30 | >30 | >30 | >30 | >30 | >30 | >30 |
| N12-I4 | 30 | >30 | >30 | >30 | >30 | >30 | >30 | >30 | >30 | >30 | >30 | <0.1 |
| N12-I5 | >30 | >30 | >30 | >30 | >30 | >30 | >30 | >30 | >30 | >30 | >30 | >30 |
| N12-I7 | 15 | >30 | >30 | >30 | >30 | >30 | >30 | >30 | >30 | >30 | >30 | >30 |
| N12-I8 | 20 | >30 | >30 | >30 | >30 | >30 | >30 | >30 | >30 | >30 | >30 | >30 |
| N12-I8.1 | 25 | >30 | >30 | >30 | >30 | >30 | >30 | >30 | >30 | >30 | >30 | >30 |
| N12-I9 | 25 | >30 | >30 | >30 | >30 | >30 | >30 | >30 | >30 | >30 | >30 | >30 |
| N12-I10 | 25 | >50 | >50 | >50 | >50 | >50 | >50 | >50 | >50 | >50 | >50 | >50 |
| N12-I11 | >30 | >30 | >30 | >30 | >30 | >30 | >30 | >30 | >30 | >30 | >30 | >30 |
| N12-I12 | >30 | >30 | >30 | >30 | >30 | >30 | >30 | >30 | >30 | >30 | >30 | >30 |
| N12-I14 | 12 | >50 | >50 | >50 | >50 | >50 | >50 | >50 | >50 | >50 | >50 | >50 |
| N12-I15 | >30 | >30 | >30 | >30 | >30 | >30 | >30 | >30 | >30 | >30 | >30 | >30 |
| N12-I16 | >30 | >30 | >30 | >30 | >30 | >30 | >30 | >30 | >30 | >30 | >30 | >30 |
| N12-I17 | 25 | >50 | >50 | >50 | >50 | >50 | >50 | >50 | >50 | >50 | >50 | >50 |
| N12-I17.1 | 9 | >50 | >50 | >50 | >50 | >50 | >50 | >50 | >50 | >50 | >50 | 6 |
| N12-I18 | 50 | >50 | >50 | >50 | >50 | >50 | >50 | >50 | >50 | >50 | >50 | >50 |
| N12-I18.1 | 25 | >50 | >50 | >50 | >50 | >50 | >50 | >50 | >50 | >50 | >50 | >50 |
| N12-I19 | 12 | >50 | >50 | >50 | >50 | >50 | >50 | >50 | >50 | >50 | >50 | >50 |
| N5-I1 | 30 | >30 | >30 | >30 | >30 | >30 | >30 | >30 | >30 | >30 | >30 | >30 |
| N5-I2 | 90 | >30 | >30 | >30 | >30 | >30 | >30 | >30 | >30 | >30 | >30 | >30 |
| N5-I3 | 30 | >30 | >30 | >30 | >30 | >30 | >30 | >30 | >30 | >30 | >30 | >30 |
| N5-I4 | 30 | >30 | >30 | >30 | >30 | >30 | >30 | >30 | >30 | >30 | >30 | >30 |
| N26-I1 | >30 | >30 | >30 | >30 | >30 | >30 | >30 | >30 | >30 | >30 | >30 | >30 |
| L9-I1 | >50 | >50 | >50 | >50 | >50 | >50 | >50 | >50 | >50 | >50 | >50 | >50 |
| L9-I2 | >50 | >50 | >50 | >50 | >50 | >50 | >50 | >50 | >50 | >50 | >50 | >50 |
| L9-I3 | 18 | >50 | 50 | >50 | >50 | >50 | >50 | >50 | >50 | >50 | >50 | >50 |
| L9-I4 | >50 | >50 | >50 | >50 | >50 | >50 | >50 | >50 | >50 | >50 | >50 | >50 |
| 17b | 30 | >30 | >30 | >30 | >30 | >30 | >30 | >30 | >30 | >30 | 10 | <0.1 |
| E51 | 45 | >30 | >30 | >30 | >30 | >30 | >30 | >30 | >30 | >30 | >30 | >30 |
| 19e | >30 | >30 | >30 | >30 | >30 | >30 | >30 | >30 | >30 | >30 | >30 | <0.1 |
| N12-B1 | >90 | >90 | >90 | >90 | 90 | >90 | >90 | >90 | >90 | >90 | >90 | >90 |
| N12-B2 | 90 | 90 | >90 | >90 | 30 | >90 | >90 | >90 | >90 | >90 | >90 | >90 |
| N12-B3 | 80 | >90 | >90 | >90 | 45 | >90 | >90 | >90 | >90 | >90 | >90 | >90 |
| N12-B4 | 30 | >90 | >90 | >90 | 60 | >90 | >90 | >90 | >90 | >90 | >90 | >90 |
| N12-B5 | 90 | >90 | >90 | >90 | 90 | >90 | >90 | >90 | >90 | >90 | >90 | >90 |
| L9-B1 | 2 | >50 | 40 | >50 | 25 | >50 | >50 | 2 | >50 | >50 | >50 | >50 |
| L9-B2 | 20 | >50 | >50 | >50 | >50 | >50 | >50 | 50 | >50 | >50 | >50 | >50 |
| L9-B3.1 | 10 | >50 | >50 | >50 | >50 | >50 | >50 | 40 | >50 | >50 | >50 | >50 |
| b12 | <0.1 | <0.1 | 0.2 | 1.2 | 18 | >30 | 0.3 | 12 | >30 | >30 | >30 | >30 |
| N12-O1 | >50 | >50 | >50 | >50 | >50 | >50 | >50 | >50 | >50 | >50 | >50 | >50 |
| N12-O2 | 0.5 | 50 | 4 | >50 | 20 | >50 | >50 | >50 | >50 | >50 | >50 | >50 |
| N12-O3.1 | <0.5 | 50 | 2 | 50 | 15 | >50 | >50 | 40 | >50 | >50 | >50 | >50 |
| N5-O1.1 | <0.5 | 50 | 0.5 | 50 | 5 | >50 | >50 | 40 | >50 | >50 | >50 | >50 |
| 2G12 | 0.5 | 0.3 | 1 | 12 | 8 | 0.3 | >25 | >25 | >25 | >25 | >25 | >25 |

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Gallo, R. C., *The end or the beginning of the drive to an HIV-preventive vaccine: a view from over 20 years.* Lancet, 2005. 366(9500): p. 1894-8.
2. Fauci, A. S., et al., *HIV vaccine research: the way forward.* Science, 2008. 321(5888): p. 530-2.
3. Braibant, M., et al., *Antibodies to conserved epitopes of the HIV-1 envelope in sera from long-term non-progressors: prevalence and association with neutralizing activity.* AIDS, 2006. 20(15): p. 1923-30.
4. Walker, B. D., *Elite control of HIV Infection: implications for vaccines and treatment.* Top HIV Med, 2007. 15(4): p. 134-6.
5. Sajadi, M. M., et al., *HIV-1 natural viral suppressors: control of viral replication in the absence of therapy.* AIDS, 2007. 21(4): p. 517-9.
6. Li, Y., et al., *Broad HIV-1 neutralization mediated by CD4-binding site antibodies.* Nat Med, 2007. 13(9): p. 1032-4.
7. Dhillon, A. K., et al., *Dissecting the neutralizing antibody specificities of broadly neutralizing sera from human immunodeficiency virus type 1-infected donors.* J Virol, 2007. 81(12): p. 6548-62.
8. Wei, X., et al., *Antibody neutralization and escape by HIV-1.* Nature, 2003. 422(6929): p. 307-12.
9. Bailey, J. R., et al., *Neutralizing antibodies do not mediate suppression of human immunodeficiency virus type 1 in elite suppressors or selection of plasma virus variants in patients on highly active antiretroviral therapy.* J Virol, 2006. 80(10): p. 4758-70.
10. Pereyra, F., et al., *Genetic and immunologic heterogeneity among persons who control HIV infection in the absence of therapy.* J Infect Dis, 2008. 197(4): p. 563-71.
11. Bernasconi, N. L., E. Traggiai, and A. Lanzavecchia, *Maintenance of serological memory by polyclonal activation of human memory B cells.* Science, 2002. 298(5601): p. 2199-202.
12. Crotty, S., et al., *Cutting edge: long-term B cell memory in humans after smallpox vaccination.* J Immunol, 2003. 171 (10): p. 4969-73.
13. Jilg, W., M. Schmidt, and F. Deinhardt, *Decline of anti-HBs after hepatitis B vaccination and timing of revaccination.* Lancet, 1990. 335(8682): p. 173-4.
14. Banatvala, J., P. Van Damme, and S. Oehen, *Lifelong protection against hepatitis B: the role of vaccine immunogenicity in immune memory.* Vaccine, 2000. 19(7-8): p. 877-85.
15. Bauer, T. and W. Jilg, *Hepatitis B surface antigen-specific T and B cell memory in individuals who had lost protective antibodies after hepatitis B vaccination.* Vaccine, 2006. 24(5): p. 572-7.
16. Wainwright, R. B., et al., *Protection provided by hepatitis B vaccine in a Yupik Eskimo population-results of a 10-year study.* J Infect Dis, 1997. 175(3): p. 674-7.
17. West, D. J. and G. B. Calandra, *Vaccine induced immunologic memory for hepatitis B surface antigen: implications for policy on booster vaccination.* Vaccine, 1996. 14(11): p. 1019-27.
18. Moir, S., et al., *Evidence for HIV-associated B cell exhaustion in a dysfunctional memory B cell compartment in HIV-infected viremic individuals.* J Exp Med, 2008. 205(8): p. 1797-805.
19. Titanji, K., et al., *Loss of memory B cells impairs maintenance of long-term serologic memory during HIV-1 infection.* Blood, 2006. 108(5): p. 1580-7.
20. Decker, J. M., et al., *Antigenic conservation and immunogenicity of the HIV coreceptor binding site.* J Exp Med, 2005. 201(9): p. 1407-19.
21. Kwong, P. D., et al., *Structure of an HIV gp120 envelope glycoprotein in complex with the CD4 receptor and a neutralizing human antibody.* Nature, 1998. 393(6686): p. 648-59.
22. Rizzuto, C. D., et al., *A conserved HIV gp120 glycoprotein structure involved in chemokine receptor binding.* Science, 1998. 280(5371): p. 1949-53.
23. Wyatt, R., et al., *The antigenic structure of the HIV gp120 envelope glycoprotein.* Nature, 1998. 393(6686): p. 705-11.
24. Robinson, J. E., et al., *High frequencies of antibody responses to CD4 induced epitopes in HIV infected patients started on HAART during acute infection.* Hum Antibodies, 2005. 14(3-4): p. 115-21.
25. Burton, D. R., et al., *Efficient neutralization of primary isolates of HIV-1 by a recombinant human monoclonal antibody.* Science, 1994. 266(5187): p. 1024-7.
26. Traggiai, E., et al., *An efficient method to make human monoclonal antibodies from memory B cells: potent neutralization of SARS coronavirus.* Nat Med, 2004. 10(8): p. 871-5.
27. Huang, C. C., et al., *Structural basis of tyrosine sulfation and VH-gene usage in antibodies that recognize the HIV type 1 coreceptor-binding site on gp120.* Proc Natl Acad Sci USA, 2004. 101(9): p. 2706-11.
28. DeVico, A., et al., *Antibodies to CD4-induced sites in HIV gp120 correlate with the control of SHIV challenge in macaques vaccinated with subunit immunogens.* Proc Natl Acad Sci USA, 2007. 104(44): p. 17477-82.
29. Gray, E. S., et al., *Neutralizing antibody responses in acute human immunodeficiency virus type 1 subtype C infection.* J Virol, 2007. 81(12): p. 6187-96.
30. Fouts, T. R., et al., *Expression and characterization of a single-chain polypeptide analogue of the human immunodeficiency virus type 1 gp120-CD4 receptor complex.* J Virol, 2000. 74(24): p. 11427-36.
31. Center, R. J., et al., *Promoting trimerization of soluble human immunodeficiency virus type 1 (HIV-1) Env through the use of HIV-1/simian immunodeficiency virus chimeras.* J Virol, 2004. 78(5): p. 2265-76.
32. Vu, J. R., et al., *An immunoglobulin fusion protein based on the gp120-CD4 receptor complex potently inhibits human immunodeficiency virus type 1 in vitro.* AIDS Res Hum Retroviruses, 2006. 22(6): p. 477-90.
33. Zhang, M. Y., et al., *Identification and characterization of a new cross-reactive human immunodeficiency virus type 1-neutralizing human monoclonal antibody.* J Virol, 2004. 78(17): p. 9233-42.
34. Moore, J. P., et al., *An enzyme-linked immunosorbent assay for antibodies to the envelope glycoproteins of divergent strains of HIV-1.* AIDS, 1989. 3(3): p. 155-63.
35. Turbica, I., et al., *Simple enzyme immunoassay for titration of antibodies to the CD4-binding site of human immunodeficiency virus type 1 gp120.* J Clin Microbiol, 1995. 33(12): p. 3319-23.

36. Fouts, T., et al., *Crosslinked HIV-1 envelope-CD4 receptor complexes elicit broadly cross-reactive neutralizing antibodies in rhesus macaques*. Proc Natl Acad Sci USA, 2002. 99(18): p. 11842-7.
37. Li, M., et al., *Human immunodeficiency virus type 1 env clones from acute and early subtype B infections for standardized assessments of vaccine-elicited neutralizing antibodies*. J Virol, 2005. 79(16): p. 10108-25.
38. Amanna, I. J., N. E. Carlson, and M K Slifka, *Duration of humoral immunity to common viral and vaccine antigens*. N Engl J Med, 2007. 357(19): p. 1903-15.
39. Tiller, T., et al., *Efficient generation of monoclonal antibodies from single human B cells by single cell RT-PCR and expression vector cloning*. J Immunol Methods, 2008. 329(1-2): p. 112-24.
40. Teng N N, Lam K S, Calvo Riera F, & Kaplan H S (1983) Construction and testing of mouse-human heteromyelomas for human monoclonal antibody production. *Proceedings of the National Academy of Sciences of the United States of America* 80, 7308-7312.
41. Steinitz M, Koskimies S, Klein G, & Makela O (1978) Establishment of specific antibody producing human lines by antigen preselection and EBV-transformation. *Current topics in microbiology and immunology* 81, 156-163.
42. Clackson T, Hoogenboom H R, Griffiths A D, & Winter G (1991) Making antibody fragments using phage display libraries. *Nature* 352, 624-628.
43. Feldhaus M J, Siegel R W, Opresko L K, Coleman J R, Feldhaus J M, Yeung Y A, Cochran J R, Heinzelman P, Colby D, Swers J, et al. (2003) Flow-cytometric isolation of human antibodies from a nonimmune *Saccharomyces cerevisiae* surface display library. *Nature biotechnology* 21, 163-170.
44. Queen C, Schneider W P, Selick H E, Payne P W, Landolfi N F, Duncan J F, Avdalovic N M, Levitt M, Junghans R P, & Waldmann T A (1989) A humanized antibody that binds to the interleukin 2 receptor. *Proceedings of the National Academy of Sciences of the United States of America* 86, 10029-10033.
45. Yu X, Tsibane T, McGraw P A, House F S, Keefer C J, Hicar M D, Tumpey T M, Pappas C, Perrone L A, Martinez O, et al. (2008) Neutralizing antibodies derived from the B cells of 1918 influenza pandemic survivors. *Nature* 455, 532-536.
46. Bowley D R, Labrijn A F, Zwick M B, & Burton D R (2007) Antigen selection from an HIV-1 immune antibody library displayed on yeast yields many novel antibodies compared to selection from the same library displayed on phage. *Protein Eng Des Sel* 20, 81-90.
47. Hemmi H, Takeuchi O, Kawai T, Kaisho T, Sato S, Sanjo H, Matsumoto M, Hoshino K, Wagner H, Takeda K, et al. (2000) A Toll-like receptor recognizes bacterial DNA. *Nature* 408, 740-745.
48. Bernasconi N L, Onai N, & Lanzavecchia A (2003) A role for Toll-like receptors in acquired immunity: up-regulation of TLR9 by BCR triggering in naive B cells and constitutive expression in memory B cells. *Blood* 101, 4500-4504.
49. Askonas B A & Williamson A R (1966) Biosynthesis of immunoglobulins on polyribosomes and assembly of the IgG molecule. *Proceedings of the Royal Society of London. Series B, Containing papers of a Biological character* 166, 232-243.
50. Aruffo A & Seed B (1987) Molecular cloning of a CD28 cDNA by a high-efficiency COS cell expression system. *Proceedings of the National Academy of Sciences of the United States of America* 84, 8573-8577.
51. Aruffo A & Seed B (1987) Molecular cloning of two CD7 (T-cell leukemia antigen) cDNAs by a COS cell expression system. *The EMBO journal* 6, 3313-3316.
52. Amanna I J, Slifka M K, & Crotty S (2006) Immunity and immunological memory following smallpox vaccination. *Immunological reviews* 211, 320-337.

We claim:

1. A method for producing a monoclonal antibody that specifically binds to a particular known antigen, comprising the steps of:
   (a) obtaining a blood sample from an animal that has been exposed to the particular known antigen;
   (b) isolating a plurality of memory B cells from the blood sample;
   (c) culturing the plurality of the isolated memory B cells under conditions and for a sufficient time to permit the memory B cells to differentiate into plasma cells that stably produce monoclonal antibodies;
   (d) determining whether the plasma cells produce the monoclonal antibody that specifically binds to the particular known antigen;
   (e) if the plasma cells produce the monoclonal antibody that specifically binds to the particular known antigen, then isolating total RNA from the plasma cells, and if the plasma cells do not produce the monoclonal antibody, then repeating steps (b) through (d) until a plurality of isolated memory B cells is identified that differentiates into plasma cells that stably produce the monoclonal antibody;
   (f) using the isolated total RNA of step (e) to produce cDNA encoding variable-heavy (VH) antibody chains and cDNA encoding variable-light (VL) antibody chains encoded by mRNA molecules within the total RNA;
   (g) cloning VH chain cDNA into a eukaryotic expression vector and cloning VL chain cDNA into a eukaryotic expression vector,
   (h) selecting expression vectors comprising VH chain cDNA to produce a VH chain mini-library and selecting expression vectors comprising VL chain cDNA to make a VL chain mini-library;
   (i) co-transfecting an appropriate host cell with a mixture comprising VH chain cDNA expression vectors from the VH chain mini-library and with a mixture comprising VL chain cDNA expression vectors from the VL chain mini-library, and growing the co-transfected cells under conditions and for a sufficient time to permit the cells to stably produce antibodies;
   (j) determining that the co-transfected cells produce the monoclonal antibody that specifically binds to the particular known antigen;
   (k) identifying the VH chain cDNA that encodes the VH chain of the monoclonal antibody of step (j), comprising the steps of:
      (i) co-transfecting an appropriate host cell with a particular VH chain cDNA expression vector obtained from the VH chain cDNA mini-library and with a mixture comprising VL chain cDNA expression vectors from the VL chain mini-library, and growing co-transfected cells under conditions and for a sufficient time to permit the co-transfected cells to form a clone that stably produces an antibody;
      (ii) determining whether the clone produces the monoclonal antibody that specifically binds to the particular known antigen;
      (iii) if the co-transfected cells produce the monoclonal antibody that specifically binds to the particular known antigen, then proceeding to step (k)(iv), and if the co-transfected cells do not produce the monoclonal antibody, then repeating steps (k)(i) and (k)(ii) using a different particular VH chain cDNA expression vector until a particular VH chain cDNA expression vector is identified that produces the monoclonal antibody;
      (iv) identifying the VH chain cDNA that produced the monoclonal antibody, and selecting the VH chain cDNA expression vector that was used to make the clone that produces the monoclonal antibody that specifically binds to the particular known antigen;
   (l) identifying the VL chain cDNA that encodes the VL chain of the monoclonal antibody of step (k), comprising the steps of:
      (i) co-transfecting an appropriate host cell with the VH chain cDNA expression vector identified in step (k)(iv) and with a particular VL chain cDNA expression vector selected from the VL chain mini-library, and growing co-transfected cells under conditions and for a sufficient time to permit the co-transfected cells to form a clone that stably produces an antibody;
      (ii) determining whether the clone produces the monoclonal antibody that specifically binds to the particular known antigen;
      (iii) if the clone produces the monoclonal antibody that specifically binds to the particular known antigen then proceeding to step (1)(iv), and if the co-transfected cells do not produce the monoclonal antibody, then repeating steps (1)(i) and (1)(ii) with a different particular VL chain cDNA expression vector until a particular VL chain cDNA expression vector is identified that produces the monoclonal antibody;
      (iv) identifying the VL chain cDNA that encodes the VL chain of the monoclonal antibody, and selecting the VL chain cDNA expression vector that was used to make the clone that produces the monoclonal antibody; and
   (m) co-transfecting an appropriate host cell with the identified VH chain cDNA expression vector of step (k)(iv) and the identified VL chain cDNA expression vector of step (1)(iv) to produce a host cell that produces the monoclonal antibody that specifically bind to the particular known antigen, thereby producing a monoclonal antibody that binds to a particular known antigen.

2. The method of claim 1, wherein the particular known antigen is an antigen from a pathogen.

3. The method of claim 2, wherein the pathogen is human immunodeficiency virus (HIV).

4. The method of claim 3, wherein the animal is infected with human immunodeficiency virus (HIV) and is able to spontaneously control viremia.

5. The method of claim 1, wherein the animal is a human and the monoclonal antibodies are fully human monoclonal antibodies.

* * * * *